(12) United States Patent
Renzi et al.

(10) Patent No.: US 7,982,028 B2
(45) Date of Patent: Jul. 19, 2011

(54) OLIGONUCLEOTIDES AFFECTING EXPRESSION OF PHOSPHODIESTERASES

(75) Inventors: Paolo Renzi, Westmount (CA); Luc Paquet, Sherbrooke (CA); Helene D'Anjou, Boucherville (CA)

(73) Assignee: Topigen Pharmaceuticals, Inc., Montreal, Quebec (CA)

( * ) Notice: Subject to any disclaimer, the term of this patent is extended or adjusted under 35 U.S.C. 154(b) by 0 days.

(21) Appl. No.: 12/301,442

(22) PCT Filed: May 18, 2007

(86) PCT No.: PCT/CA2007/000902
§ 371 (c)(1),
(2), (4) Date: Oct. 23, 2009

(87) PCT Pub. No.: WO2007/134451
PCT Pub. Date: Nov. 29, 2007

(65) Prior Publication Data
US 2011/0086901 A9    Apr. 14, 2011

Related U.S. Application Data

(60) Provisional application No. 60/801,384, filed on May 19, 2006.

(51) Int. Cl.
*C07H 21/04* (2006.01)
*A61K 31/70* (2006.01)

(52) U.S. Cl. .......................................... 536/24.5; 514/44

(58) Field of Classification Search ........................ None
See application file for complete search history.

(56) References Cited

U.S. PATENT DOCUMENTS

| 4,880,635 | A  | 11/1989 | Janoff et al. |
| 4,906,477 | A  | 3/1990  | Kurono et al. |
| 4,911,928 | A  | 3/1990  | Wallach |
| 4,917,951 | A  | 4/1990  | Wallach |
| 4,920,016 | A  | 4/1990  | Allen et al. |
| 4,921,757 | A  | 5/1990  | Wheatley et al. |
| 5,734,039 | A  | 3/1998  | Calabretta et al. |
| 5,885,834 | A  | 3/1999  | Epstein |
| 6,025,339 | A  | 2/2000  | Nyce et al. |
| 6,165,789 | A  | 12/2000 | Monia et al. |
| 6,348,450 | B1 | 2/2002  | Tang et al. |
| 7,022,849 | B2 | 4/2006  | Pitts et al. |
| 2003/0087845 | A1 | 5/2003 | Nyce et al. |
| 2003/0220273 | A1 | 11/2003 | Bennett et al. |
| 2005/0244851 | A1 | 11/2005 | Blume et al. |

FOREIGN PATENT DOCUMENTS

| WO | WO97/35989 | 10/1997 |
| WO | WO99/66037 | 12/1999 |
| WO | WO99/67378 | 12/1999 |
| WO | WO00/40714 | 11/2000 |
| WO | WO02/20773 | 3/2002 |
| WO | WO02/22661 | 3/2002 |
| WO | WO03/012030 | 2/2003 |
| WO | WO03/037909 | 5/2003 |
| WO | WO03/064441 | 8/2003 |
| WO | WO2004/016613 | 2/2004 |
| WO | 2004044235 | 5/2004 |
| WO | WO2005/030787 | 4/2005 |

OTHER PUBLICATIONS

Essayan, D.M., "Cyclic nucleotide phosphodiesterase (PDE) inhibitors and immunomodulation", Biochem. Pharmacol., 1999, 57:965-973.
Perry M.J. et al., "Chemotherapeutic potential of phosphodiesterase inhibitors", Curr Opin Chem Biol, 1998, 4:472-481.
Bundschuch, D.D. et al., J. Pharmacol. Exp. Ther., 2001, 297:280-290.
Li, L. et al., "CD3- and CD28-dependent induction of PDE7 required for T cell activation", Science, 1999, 283:848-851.
Burnouf, C. et al., "Recent advances in PDE4 inhibitors as immunoregulators and anti-inflammatory drugs", Current Pharmaceutical Design, 2002, 8:1255-1296.
Giembycz, M.A., "Cilomilast: a second generation phosphodiesterase 4 inhibitor for asthma and chronic obstructive pulmonary disease", Expert Opin Invest Drugs, 2001, 10:1361-1379.
Muller et al., TiPS Aug. 1996, 17:294-298.
Szilasi, M. et al., "Pathology of chronic obstructive pulmonary disease", Pathology Oncology Research, 2006, 12:52-60.
Keatings et al., "Differences in interleukin-8 and tumor necrosis factor-alpha in induced sputum from patients with chronic obstructive pulmonary disease or asthma", Am. J. Respir. Crit. Care Med., 1996, 153:530-534.
DeGodoy et al., "Elevated TNF-alpha production by peripheral blood monocytes of weight-losing COPD patients", Am. J. Respir. Crit. Care Med., 1996, 153:633-637.
Torphy, "Phosphodiesterase isozymes: molecular targets for novel antiasthma agents", Am. J. Respir. Crit. Care Med., 1998, 157:351-370.
Au et al., "Effect of PDE4 inhibitors on zymosan-induced IL-8 release from human neutrophils: synergism with prostanoids and salbutamol", Br. J. Pharmacol., 1998, 123:1260-1266.
Compton et al., "Cilomilast, a selective phosphodiesterase-4 inhibitor for treatment of patients with chronic obstructive pulmonary disease: a randomised, dose-ranging study", Lancet., 2001, 358:265-270.
Kurreck, J., "Antisense technologies: Improvement through novel chemical modifications", Eur. J. Biochem., 2003, 270:1628-1644.
Wilds, C.J. et al., "2'-Deoxy-2'-fluoro-b-D-arabinonucleosides and oligonucleotides (2'F-ANA): synthesis and physiochemical studies", Nucl. Acids Res., 2000, 28:3625-3635.

(Continued)

*Primary Examiner* — Tracy Vivlemore
(74) *Attorney, Agent, or Firm* — Pepper Hamilton LLP

(57) ABSTRACT

The invention relates to therapeutic antisense oligonucleotides directed against genes encoding phosphodiesterases (PDE) and the use of these antisense oligonucleotides in combination. These antisense oligonucleotides may be used as analytical tools and/or as therapeutic agents in the treatment of disease associated with reduced cellular cAMP in a patient, such as inflammatory diseases of the respiratory tract including, for example, asthma, chronic obstructive pulmonary disease (COPD), acute respiratory distress syndrome, bronchitis, chronic bronchitis, silicosis, pulmonary fibrosis, lung allograft rejection, allergic rhinitis and chronic sinusitis as well as other conditions in which an increase in cyclic AMP or a decrease in PDE levels is beneficial.

32 Claims, 15 Drawing Sheets

OTHER PUBLICATIONS

Ma et al. Mol. Pharmacol., 1999, 55, 50-57.
Wang et al., Molec. Pharmocol., 1999, 56:170-174.
Churg et al., Am J Respir Crit. Care Med., 2000, 166:849-854.
Churg, et al. AM J Respir Crit. Mol. Biol., 2002, 27:368-374.
Gaede, K.I. et al. (1999) J. Mol. Med. 77:847-852.
Kebelmann-Betzing, C. et al. (2001) Cytokine. 13:39-50.
Ishii, Y et al. (2003) Int. J. Cancer. 103:161-168.
Weintraub et al., Scientific American, Jan. 1990: 40-46.
Nemoz et al., FEBS Letters 1996, 384:97-102.
Wang et al., Biochemical and Biophysical Research Communications 2000, 276:1271-1277.
MacKenzie et al., Proc. Natl. Acad. Sci. USA, Mar. 1999, vol. 95, No. 7, pp. 3549-3554.
Soderling et al., Curr. Opin. Cell. Bio., Apr. 2000, vol. 12, No. 2, pp. 174-179.
Epstein, Methods: A companion to methods in enzymology. Jan. 1998, vol. 14, No. 1, pp. 21-33.
Clayton et al., Respiratory Research, 2004, 5.
McCluskie et al., American Society for Pharmacology and Experimental Therapeutics, JPET #105080, 2006.
Smith et al., Molecular Pharmacology 2004, vol. 66, No. 6, 1679.
Robichaud et al., J. Clinical Investigation 2002, 110 (7) : 1045.
Robichaud et al., Brit. J. Pharmacology 2002, 135: 113.
Calverley et al., Am. J. Respir. Cult. Care. Med. 2007, 176:154.
Dietsch et al., Toxicologic Phatology 2006, 34:39.
Supplementary European Search Report dated Jul. 20, 2010 from European Patent Application No. 07719824.
Chung, F.F. et al. "Phosphodiesterase inhibitors in airways disease", European Journal of Pharmacology, 2006, 533:110-117.
Fortin, M. et al., "A multi-target antisense approach against PDE4 and PDE7 reduces smoke-induced lung inflammation in mice", Respiratory Research, 2009, 10:39.

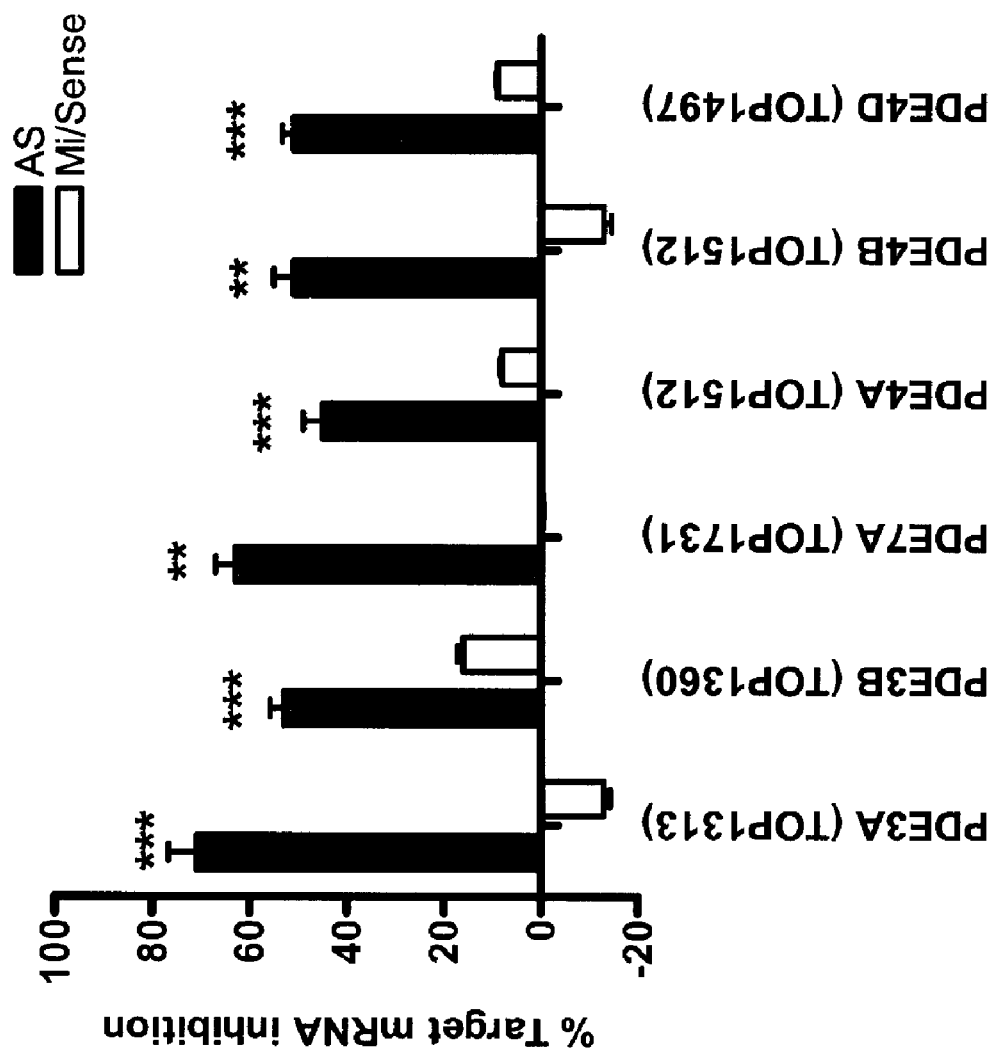

Figure 4
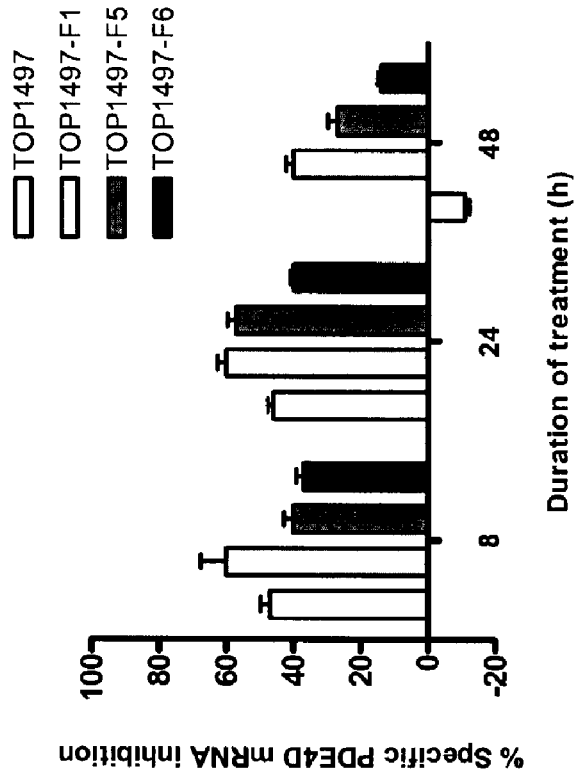
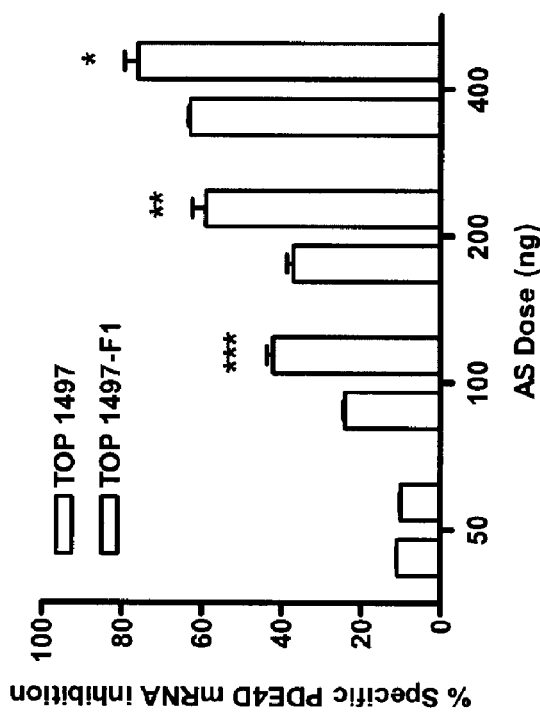
| TOP1497 | ctgcctccttcaacctg |
| TOP1497-F1 | CTGCCTccttcaACCTG |
| TOP1497-F5 | CTgcctccttcaACCTG |
| TOP1497-F6 | ctgcctccttcaACCTG |
Lower case=PS-DNA
UPPER CASE=PS-FANA

Figure 9
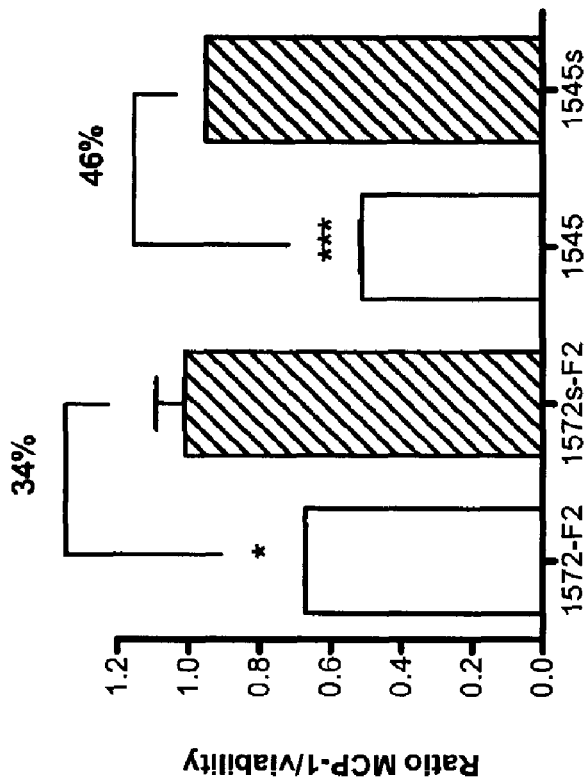
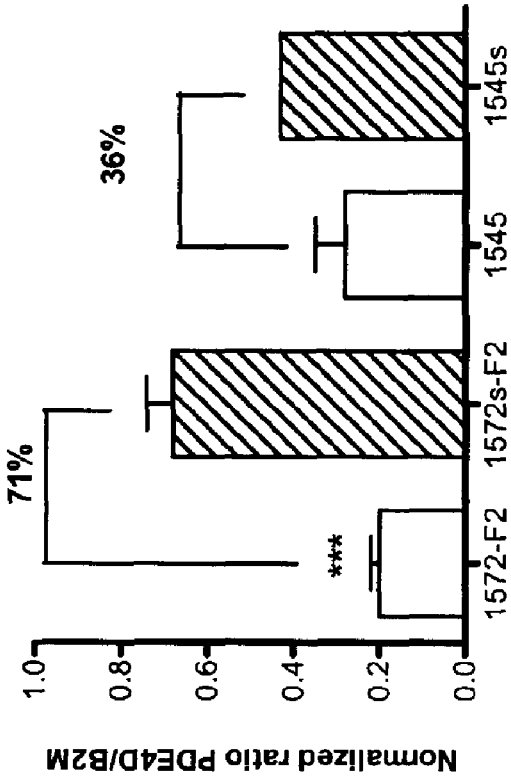

Figure 13
A)
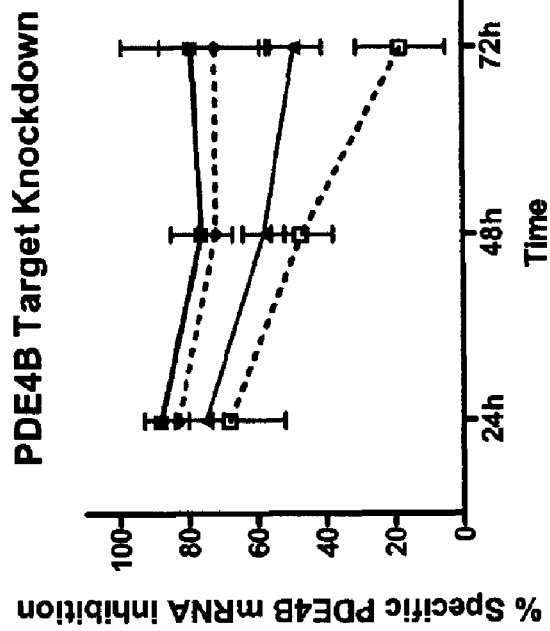
B)
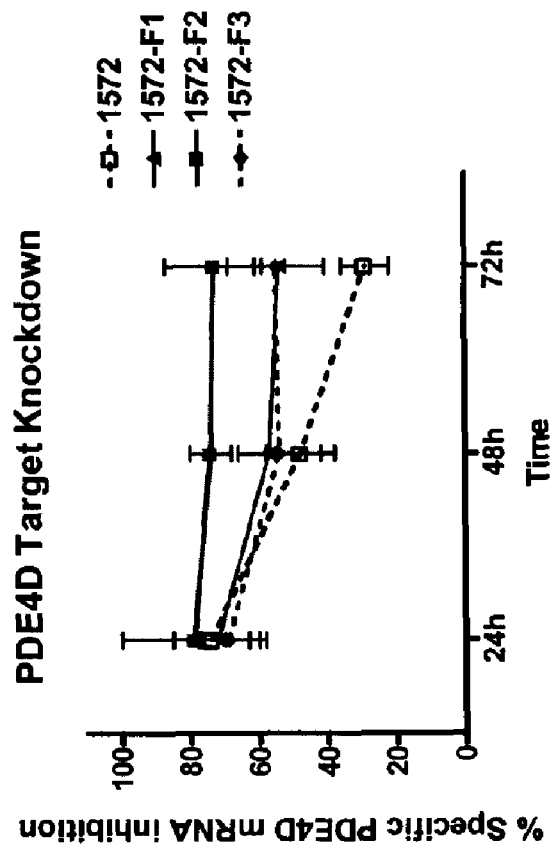

SEQUENCE LISTING

```
<160> NUMBER OF SEQ ID NOS: 126

<210> SEQ ID NO 1
<211> LENGTH: 19
<212> TYPE: DNA
<213> ORGANISM: Human

<400> SEQUENCE: 1
tcatgagtgg cagctgcaa                                                19

<210> SEQ ID NO 2
<211> LENGTH: 21
<212> TYPE: DNA
<213> ORGANISM: Human

<400> SEQUENCE: 2
tcatgagtgg cagctgcaat t                                             21

<210> SEQ ID NO 3
<211> LENGTH: 22
<212> TYPE: DNA
<213> ORGANISM: Human

<400> SEQUENCE: 3
catgagtggc agctgcaatt aa                                            22

<210> SEQ ID NO 4
<211> LENGTH: 21
<212> TYPE: DNA
<213> ORGANISM: Human

<400> SEQUENCE: 4
gagtggcagc tgcaattaag c                                             21

<210> SEQ ID NO 5
<211> LENGTH: 21
<212> TYPE: DNA
<213> ORGANISM: Human

<400> SEQUENCE: 5
atgagtggca gctgcaatta a                                             21

<210> SEQ ID NO 6
<211> LENGTH: 21
<212> TYPE: DNA
<213> ORGANISM: Human

<400> SEQUENCE: 6
agatcatgag tggcagctgc a                                             21

<210> SEQ ID NO 7
<211> LENGTH: 19
<212> TYPE: DNA
```

<213> ORGANISM: Human

<400> SEQUENCE: 7
gagtggcagc tgcaattaa                                                    19

<210> SEQ ID NO 8
<211> LENGTH: 21
<212> TYPE: DNA
<213> ORGANISM: Human

<400> SEQUENCE: 8
gatcatgagt ggcagctgca a                                                 21

<210> SEQ ID NO 9
<211> LENGTH: 20
<212> TYPE: DNA
<213> ORGANISM: Human

<400> SEQUENCE: 9
cctcagcacc agccatgtcg                                                   20

<210> SEQ ID NO 10
<211> LENGTH: 17
<212> TYPE: DNA
<213> ORGANISM: Homo sapiens

<400> SEQUENCE: 10
gtgcttgtca cacatgg                                                      17

<210> SEQ ID NO 11
<211> LENGTH: 16
<212> TYPE: DNA
<213> ORGANISM: Homo sapiens

<400> SEQUENCE: 11
gtcctccaaa gtgtcc                                                       16

<210> SEQ ID NO 12
<211> LENGTH: 15
<212> TYPE: DNA
<213> ORGANISM: Homo sapiens

<400> SEQUENCE: 12
ggtctctagc tggtc                                                        15

<210> SEQ ID NO 13
<211> LENGTH: 15
<212> TYPE: DNA
<213> ORGANISM: Homo sapiens

<400> SEQUENCE: 13
atggtaatgg tcttc                                                        15

<210> SEQ ID NO 14
<211> LENGTH: 17
<212> TYPE: DNA
<213> ORGANISM: Homo sapiens

<400> SEQUENCE: 14
tctgcccatg tctccca                                                      17

<210> SEQ ID NO 15
<211> LENGTH: 17
<212> TYPE: DNA

```
<213> ORGANISM: Homo sapiens

<400> SEQUENCE: 15
aagaccccat tgttca                                                   17

<210> SEQ ID NO 16
<211> LENGTH: 17
<212> TYPE: DNA
<213> ORGANISM: Homo sapiens

<400> SEQUENCE: 16
tctgcccagg tctccca                                                  17

<210> SEQ ID NO 17
<211> LENGTH: 17
<212> TYPE: DNA
<213> ORGANISM: Homo sapiens

<400> SEQUENCE: 17
gaggcccatg tctcccg                                                  17

<210> SEQ ID NO 18
<211> LENGTH: 19
<212> TYPE: DNA
<213> ORGANISM: Homo sapiens

<400> SEQUENCE: 18
tctgcccatg tctcccaga                                                19

<210> SEQ ID NO 19
<211> LENGTH: 19
<212> TYPE: DNA
<213> ORGANISM: Homo sapiens

<400> SEQUENCE: 19
tctgcccatg tctcccaca                                                19

<210> SEQ ID NO 20
<211> LENGTH: 20
<212> TYPE: DNA
<213> ORGANISM: Homo sapiens

<400> SEQUENCE: 20
tctgcccatg tctcccagag                                               20

<210> SEQ ID NO 21
<211> LENGTH: 20
<212> TYPE: DNA
<213> ORGANISM: Homo sapiens

<400> SEQUENCE: 21
tctgcccatg tctcccacaa                                               20

<210> SEQ ID NO 22
<211> LENGTH: 21
<212> TYPE: DNA
<213> ORGANISM: Homo sapiens

<400> SEQUENCE: 22
ggttgctcag gtctgcacag t                                             21

<210> SEQ ID NO 23
<211> LENGTH: 21
<212> TYPE: DNA
```

<213> ORGANISM: Homo sapiens

<400> SEQUENCE: 23
ggttgctcag atctgcacag t                                              21

<210> SEQ ID NO 24
<211> LENGTH: 21
<212> TYPE: DNA
<213> ORGANISM: Homo sapiens
<220> FEATURE:
<221> NAME/KEY: misc_feature
<222> LOCATION: (11)..(11)
<223> OTHER INFORMATION: Inosine

<400> SEQUENCE: 24
ggttgctcag ntctgcacag t                                              21

<210> SEQ ID NO 25
<211> LENGTH: 19
<212> TYPE: DNA
<213> ORGANISM: Homo sapiens

<400> SEQUENCE: 25
tcagcatggt aatggtctt                                                 19

<210> SEQ ID NO 26
<211> LENGTH: 19
<212> TYPE: DNA
<213> ORGANISM: Homo sapiens
<220> FEATURE:
<221> NAME/KEY: misc_feature
<222> LOCATION: (6)..(6)
<223> OTHER INFORMATION: Inosine

<400> SEQUENCE: 26
gccacntcag catggtaat                                                 19

<210> SEQ ID NO 27
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: Inosine

<400> SEQUENCE: 27
tacatcaang caagttc                                                   17

<210> SEQ ID NO 28
<211> LENGTH: 17
<212> TYPE: DNA
<213> ORGANISM: Homo sapiens
<220> FEATURE:
<221> NAME/KEY: misc_feature
<222> LOCATION: (11)..(11)
<223> OTHER INFORMATION: Inosine

<400> SEQUENCE: 28
atgtcacagt nttcttc                                                   17

<210> SEQ ID NO 29
<211> LENGTH: 19
<212> TYPE: DNA
<213> ORGANISM: Homo sapiens
<220> FEATURE:
<221> NAME/KEY: misc_feature
<222> LOCATION: (8)..(8)

```
<223> OTHER INFORMATION: Inosine

<400> SEQUENCE: 29
tgtcaatnac cattttcct                                                19

<210> SEQ ID NO 30
<211> LENGTH: 19
<212> TYPE: DNA
<213> ORGANISM: Homo sapiens
<220> FEATURE:
<221> NAME/KEY: misc_feature
<222> LOCATION: (6)..(6)
<223> OTHER INFORMATION: Inosine
<220> FEATURE:
<221> NAME/KEY: misc_feature
<222> LOCATION: (12)..(12)
<223> OTHER INFORMATION: Inosine

<400> SEQUENCE: 30
gtttcnacca tngtcttca                                                19

<210> SEQ ID NO 31
<211> LENGTH: 19
<212> TYPE: DNA
<213> ORGANISM: Homo sapiens
<220> FEATURE:
<221> NAME/KEY: misc_feature
<222> LOCATION: (14)..(14)
<223> OTHER INFORMATION: Inosine

<400> SEQUENCE: 31
ctttcttagt ttcnaccat                                                19

<210> SEQ ID NO 32
<211> LENGTH: 17
<212> TYPE: DNA
<213> ORGANISM: Homo sapiens

<400> SEQUENCE: 32
tctgcacagt gcaccat                                                  17

<210> SEQ ID NO 33
<211> LENGTH: 19
<212> TYPE: DNA
<213> ORGANISM: Homo sapiens
<220> FEATURE:
<221> NAME/KEY: misc_feature
<222> LOCATION: (8)..(8)
<223> OTHER INFORMATION: Inosine

<400> SEQUENCE: 33
gtctgtangg tctctagct                                                19

<210> SEQ ID NO 34
<211> LENGTH: 19
<212> TYPE: DNA
<213> ORGANISM: Homo sapiens
<220> FEATURE:
<221> NAME/KEY: misc_feature
<222> LOCATION: (5)..(5)
<223> OTHER INFORMATION: Inosine

<400> SEQUENCE: 34
tgtanggtct ctagctggt                                                19

<210> SEQ ID NO 35
<211> LENGTH: 19
<212> TYPE: DNA
```

```
<213> ORGANISM: Homo sapiens
<220> FEATURE:
<221> NAME/KEY: misc_feature
<222> LOCATION: (15)..(15)
<223> OTHER INFORMATION: Inosine

<400> SEQUENCE: 35
ttcttgactc cactnatct                                                    19

<210> SEQ ID NO 36
<211> LENGTH: 19
<212> TYPE: DNA
<213> ORGANISM: Homo sapiens
<220> FEATURE:
<221> NAME/KEY: misc_feature
<222> LOCATION: (13)..(13)
<223> OTHER INFORMATION: Inosine

<400> SEQUENCE: 36
aatcaagtca tcnccgtgt                                                    19

<210> SEQ ID NO 37
<211> LENGTH: 19
<212> TYPE: DNA
<213> ORGANISM: Homo sapiens
<220> FEATURE:
<221> NAME/KEY: misc_feature
<222> LOCATION: (10)..(10)
<223> OTHER INFORMATION: Inosine
<220> FEATURE:
<221> NAME/KEY: misc_feature
<222> LOCATION: (16)..(16)
<223> OTHER INFORMATION: Inosine

<400> SEQUENCE: 37
gttgtgatan gccacntca                                                    19

<210> SEQ ID NO 38
<211> LENGTH: 19
<212> TYPE: DNA
<213> ORGANISM: Homo sapiens
<220> FEATURE:
<221> NAME/KEY: misc_feature
<222> LOCATION: (4)..(4)
<223> OTHER INFORMATION: Inosine
<220> FEATURE:
<221> NAME/KEY: misc_feature
<222> LOCATION: (13)..(13)
<223> OTHER INFORMATION: Inosine

<400> SEQUENCE: 38
attntacatc aangcaagt                                                    19

<210> SEQ ID NO 39
<211> LENGTH: 18
<212> TYPE: DNA
<213> ORGANISM: Homo sapiens
<220> FEATURE:
<221> NAME/KEY: misc_feature
<222> LOCATION: (6)..(6)
<223> OTHER INFORMATION: Inosine
<220> FEATURE:
<221> NAME/KEY: misc_feature
<222> LOCATION: (15)..(15)
<223> OTHER INFORMATION: Inosine

<400> SEQUENCE: 39
tgtttngaca tatcngtt                                                     18

<210> SEQ ID NO 40
```

```
<211> LENGTH: 19
<212> TYPE: DNA
<213> ORGANISM: Homo sapiens
<220> FEATURE:
<221> NAME/KEY: misc_feature
<222> LOCATION: (11)..(11)
<223> OTHER INFORMATION: Inosine

<400> SEQUENCE: 40
ggttgctcag ntctgcaca                                                19

<210> SEQ ID NO 41
<211> LENGTH: 17
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 6, 13,
      14, 15, 16, 17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 41
tcatgagtgg cagctgc                                                  17

<210> SEQ ID NO 42
<211> LENGTH: 17
<212> TYPE: DNA
<213> ORGANISM: Human
<220> FEATURE:
<221> NAME/KEY: misc_feature
<223> OTHER INFORMATION: Nucleotides at positions 1, 2, 3, 6, 7, 8, 11,
      12, 15, 16, 17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 42
tcatgagtgg cagctgc                                                  17

<210> SEQ ID NO 43
<211> LENGTH: 17
<212> TYPE: DNA
<213> ORGANISM: Human
<220> FEATURE:
<221> NAME/KEY: misc_feature
<223> OTHER INFORMATION: Nucleotides at positions 2, 4, 6, 8, 10, 12,
      14, 17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 43
tcatgagtgg cagctgc                                                  17

<210> SEQ ID NO 44
<211> LENGTH: 17
<212> TYPE: DNA
<213> ORGANISM: Human
<220> FEATURE:
<221> NAME/KEY: misc_feature
<223> OTHER INFORMATION: Nucleotides at positions 1, 2, 3, 5, 6, 13, 14,
      15, 16, 17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.
```

-continued

```
<400> SEQUENCE: 44
tcatgagtgg cagctgc                                                  17

<210> SEQ ID NO 45
<211> LENGTH: 17
<212> TYPE: DNA
<213> ORGANISM: Human
<220> FEATURE:
<221> NAME/KEY: misc_feature
<223> OTHER INFORMATION: Nucleotides at positions 1, 2, 3, 13, 14, 15,
      16, 17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 45
tcatgagtgg cagctgc                                                  17

<210> SEQ ID NO 46
<211> LENGTH: 18
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 13, 14,
      15, 16, 17, 18 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 46
gcttaggttc ctttaagt                                                 18

<210> SEQ ID NO 47
<211> LENGTH: 20
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 15, 16,
      17, 18, 19, 20 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 47
cagatcatga gtcccagctg                                               20

<210> SEQ ID NO 48
<211> LENGTH: 19
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 14, 15,
      16, 17, 18, 19 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 48
tcatgagtgg cagctgcaa                                                19

<210> SEQ ID NO 49
<211> LENGTH: 19
<212> TYPE: DNA
```

```
<213> ORGANISM: Human
<220> FEATURE:
<221> NAME/KEY: misc_feature
<223> OTHER INFORMATION: Nucleotides at positions 1, 2, 3, 4, 16, 17,
      18, 19 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 49
tcatgagtgg cagctgcaa                                                19

<210> SEQ ID NO 50
<211> LENGTH: 19
<212> TYPE: DNA
<213> ORGANISM: Human
<220> FEATURE:
<221> NAME/KEY: misc_feature
<223> OTHER INFORMATION: Nucleotides at positions 1, 2, 16, 17, 18, 19
      are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 50
tcatgagtgg cagctgcaa                                                19

<210> SEQ ID NO 51
<211> LENGTH: 19
<212> TYPE: DNA
<213> ORGANISM: Human
<220> FEATURE:
<221> NAME/KEY: misc_feature
<223> OTHER INFORMATION: Nucleotides at positions 1, 2, 12, 13, 14, 15,
      16, 17, 18, 19 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 51
tcatgagtgg cagctgcaa                                                19

<210> SEQ ID NO 52
<211> LENGTH: 21
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 16, 17,
      18, 19, 20, 21 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 52
tcatgagtgg cagctgcaat t                                             21

<210> SEQ ID NO 53
<211> LENGTH: 21
<212> TYPE: DNA
<213> ORGANISM: Human
<220> FEATURE:
<221> NAME/KEY: misc_feature
<223> OTHER INFORMATION: Nucleotides at positions 1, 2, 3, 4, 18, 19,
      20, 21 are 2'-deoxy-2'-fluoroarabinonucleotides.
<220> FEATURE:
<221> NAME/KEY: misc_feature
<223> OTHER INFORMATION: All nucleotides are linked by phosphorothioate
``` bonds.

<400> SEQUENCE: 53
tcatgagtgg cagctgcaat t                                            21

<210> SEQ ID NO 54
<211> LENGTH: 21
<212> TYPE: DNA
<213> ORGANISM: Human
<220> FEATURE:
<221> NAME/KEY: misc_feature
<223> OTHER INFORMATION: Nucleotides at positions 1, 2, 18, 19, 20, 21
      are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 54
tcatgagtgg cagctgcaat t                                            21

<210> SEQ ID NO 55
<211> LENGTH: 21
<212> TYPE: DNA
<213> ORGANISM: Human
<220> FEATURE:
<221> NAME/KEY: misc_feature
<223> OTHER INFORMATION: Nucleotides at positions 1, 2, 12, 13, 14, 15,
      16, 17, 18, 19, 20, 21 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 55
tcatgagtgg cagctgcaat t                                            21

<210> SEQ ID NO 56
<211> LENGTH: 21
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 16, 17,
      18, 19, 20, 21 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 56
gagtggcagc tgcaattaag c                                            21

<210> SEQ ID NO 57
<211> LENGTH: 21
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 16, 17,
      18, 19, 20, 21 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 57
atgagtggca gctgcaatta a                                            21

<210> SEQ ID NO 58

```
<211> LENGTH: 19
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 14, 15,
      16, 17, 18, 19 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 58
gagtggcagc tgcaattaa                                                 19

<210> SEQ ID NO 59
<211> LENGTH: 21
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 16, 17,
      18, 19, 20, 21 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 59
gatcatgagt ggcagctgca a                                              21

<210> SEQ ID NO 60
<211> LENGTH: 20
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 6, 7,
      8, 9, 17, 18, 19, 20 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 60
cggccaagca gctgagcacc                                                20

<210> SEQ ID NO 61
<211> LENGTH: 20
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 6, 7,
      15, 16, 17, 18, 19, 20 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 61
cggccaagca gctgagcacc                                                20

<210> SEQ ID NO 62
<211> LENGTH: 20
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 6, 13,
      14, 15, 16, 17, 18, 19, 20 are 2'-deoxy-2'-
      fluoroarabinonucleotides.
```

```
<220> FEATURE:
<221> NAME/KEY: misc_feature
<223> OTHER INFORMATION: All nucleotides are linked by phosphorothioate
      bonds.

<400> SEQUENCE: 62
cggccaagca gctgagcacc                                                     20

<210> SEQ ID NO 63
<211> LENGTH: 20
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 6, 7,
      14, 15, 16, 17, 18, 19, 20 are 2'-deoxy-2'-
      fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 63
tcagcagcgt ccgcagccag                                                     20

<210> SEQ ID NO 64
<211> LENGTH: 20
<212> TYPE: DNA
<213> ORGANISM: Human
<220> FEATURE:
<221> NAME/KEY: misc_feature
<223> OTHER INFORMATION: Nucleotides at positions 1, 2, 3, 8, 9, 10, 14,
      15, 19, 20 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 64
tcagcagcgt ccgcagccag                                                     20

<210> SEQ ID NO 65
<211> LENGTH: 20
<212> TYPE: DNA
<213> ORGANISM: Human
<220> FEATURE:
<221> NAME/KEY: misc_feature
<223> OTHER INFORMATION: Nucleotides at positions 1, 2, 3, 5, 8, 10, 11,
      12, 14, 17, 18 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 65
tcagcagcgt ccgcagccag                                                     20

<210> SEQ ID NO 66
<211> LENGTH: 17
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 6, 13,
      14, 15, 16, 17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 66
```

-continued gccacgctcg cgctctc                                                17

<210> SEQ ID NO 67
<211> LENGTH: 17
<212> TYPE: DNA
<213> ORGANISM: Human
<220> FEATURE:
<221> NAME/KEY: misc_feature
<223> OTHER INFORMATION: Nucleotides at positions 1, 2, 3, 7, 8, 9, 15,
      16, 17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 67
gccacgctcg cgctctc                                                17

<210> SEQ ID NO 68
<211> LENGTH: 17
<212> TYPE: DNA
<213> ORGANISM: Human
<220> FEATURE:
<221> NAME/KEY: misc_feature
<223> OTHER INFORMATION: Nucleotides at positions 4, 5, 6, 10, 11, 12,
      13, 14 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 68
gccacgctcg cgctctc                                                17

<210> SEQ ID NO 69
<211> LENGTH: 19
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 12, 13,
      14, 15, 16, 17, 18, 19 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 69
cttcaggctg gctttcctc                                              19

<210> SEQ ID NO 70
<211> LENGTH: 19
<212> TYPE: DNA
<213> ORGANISM: Human
<220> FEATURE:
<221> NAME/KEY: misc_feature
<223> OTHER INFORMATION: Nucleotides at positions 3, 4, 8, 9, 12, 13,
      16, 17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 70
cttcaggctg gctttcctc                                              19

<210> SEQ ID NO 71
<211> LENGTH: 19
<212> TYPE: DNA
<213> ORGANISM: Human
<220> FEATURE:

```
<221> NAME/KEY: misc_feature
<223> OTHER INFORMATION: Nucleotides at positions 11, 12, 13, 14, 15,
      16, 17, 18, 19 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 71
cttcaggctg gctttcctc                                                    19

<210> SEQ ID NO 72
<211> LENGTH: 19
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 6, 15,
      16, 17, 18, 19 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 72
ctgcctcctc ttcaacctg                                                    19

<210> SEQ ID NO 73
<211> LENGTH: 19
<212> TYPE: DNA
<213> ORGANISM: Human
<220> FEATURE:
<221> NAME/KEY: misc_feature
<223> OTHER INFORMATION: Nucleotides at positions 5, 6, 7, 8, 12, 13,
      14, 15 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 73
ctgcctcctc ttcaacctg                                                    19

<210> SEQ ID NO 74
<211> LENGTH: 19
<212> TYPE: DNA
<213> ORGANISM: Human
<220> FEATURE:
<221> NAME/KEY: misc_feature
<223> OTHER INFORMATION: Nucleotides at positions 5, 6, 7, 8, 12, 13,
      14, 15 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.
<220> FEATURE:
<221> NAME/KEY: misc_feature
<222> LOCATION: (10)..(10)
<223> OTHER INFORMATION: Butanediol linker

<400> SEQUENCE: 74
ctgcctcctn ttcaacctg                                                    19

<210> SEQ ID NO 75
<211> LENGTH: 19
<212> TYPE: DNA
<213> ORGANISM: Human
<220> FEATURE:
<221> NAME/KEY: misc_feature
<223> OTHER INFORMATION: Nucleotides at positions 1, 2, 5, 6, 15, 16,
      17, 18, 19 are 2'-deoxy-2'-fluoroarabinonucleotides.
<220> FEATURE:
```

```
<221> NAME/KEY: misc_feature
<223> OTHER INFORMATION: All nucleotides are linked by phosphorothioate
      bonds.

<400> SEQUENCE: 75
ctgcctcctc ttcaacctg                                                    19

<210> SEQ ID NO 76
<211> LENGTH: 19
<212> TYPE: DNA
<213> ORGANISM: Human
<220> FEATURE:
<221> NAME/KEY: misc_feature
<223> OTHER INFORMATION: Nucleotides at positions 1, 2, 15, 16, 17, 18,
      19 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 76
ctgcctcctc ttcaacctg                                                    19

<210> SEQ ID NO 77
<211> LENGTH: 19
<212> TYPE: DNA
<213> ORGANISM: Human
<220> FEATURE:
<221> NAME/KEY: misc_feature
<223> OTHER INFORMATION: Nucleotides at positions 15, 16, 17, 18, 19 are
      2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 77
ctgcctcctc ttcaacctg                                                    19

<210> SEQ ID NO 78
<211> LENGTH: 20
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 6, 7,
      15, 16, 17, 18, 19, 20 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 78
gaccggtagg tctgtatggt                                                   20

<210> SEQ ID NO 79
<211> LENGTH: 20
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 6, 7,
      15, 16, 17, 18, 19, 20 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.
<220> FEATURE:
<221> NAME/KEY: misc_feature
<222> LOCATION: (16)..(16)
<223> OTHER INFORMATION: Butanediol linker
```

```
<400> SEQUENCE: 79
gaccggtagg tctgtntggt                                                    20

<210> SEQ ID NO 80
<211> LENGTH: 20
<212> TYPE: DNA
<213> ORGANISM: Human
<220> FEATURE:
<221> NAME/KEY: misc_feature
<223> OTHER INFORMATION: Nucleotides at positions 1, 2, 3, 4, 12, 13,
      14, 15, 16, 17, 18, 19, 20 are 2'-deoxy-2'-
      fluoroarabinonucleotides.
<220> FEATURE:
<221> NAME/KEY: misc_feature
<223> OTHER INFORMATION: All nucleotides are linked by phosphorothioate
      bonds.
<220> FEATURE:
<221> NAME/KEY: misc_feature
<222> LOCATION: (16)..(16)
<223> OTHER INFORMATION: Butanediol linker

<400> SEQUENCE: 80
gaccggtagg tctgtntggt                                                    20

<210> SEQ ID NO 81
<211> LENGTH: 17
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 6, 12,
      13, 14, 15, 16, 17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 81
gtccactggc ggtacag                                                       17

<210> SEQ ID NO 82
<211> LENGTH: 19
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 6, 14,
      15, 16, 17, 18, 19 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 82
ccatgatgcg gtctgtcca                                                     19

<210> SEQ ID NO 83
<211> LENGTH: 17
<212> TYPE: DNA
<213> ORGANISM: Human
<220> FEATURE:
<221> NAME/KEY: misc_feature
<223> OTHER INFORMATION: Nucleotides at positions 1, 2, 3, 4, 5, 12, 13,
      14, 15, 16, 17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 83
tctgcccatg tctccca                                                       17
```

```
<210> SEQ ID NO 84
<211> LENGTH: 17
<212> TYPE: DNA
<213> ORGANISM: Human
<220> FEATURE:
<221> NAME/KEY: misc_feature
<223> OTHER INFORMATION: Nucleotides at positions 1, 2, 13, 14, 15, 16,
      17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 84
tctgcccatg tctccca                                                 17

<210> SEQ ID NO 85
<211> LENGTH: 17
<212> TYPE: DNA
<213> ORGANISM: Human
<220> FEATURE:
<221> NAME/KEY: misc_feature
<223> OTHER INFORMATION: Nucleotides at positions 1, 2, 14, 15, 16, 17
      are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 85
tctgcccatg tctccca                                                 17

<210> SEQ ID NO 86
<211> LENGTH: 17
<212> TYPE: DNA
<213> ORGANISM: Human
<220> FEATURE:
<221> NAME/KEY: misc_feature
<223> OTHER INFORMATION: Nucleotides at positions 1, 2, 11, 12, 15, 16,
      17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 86
tctgcccatg tctccca                                                 17

<210> SEQ ID NO 87
<211> LENGTH: 17
<212> TYPE: DNA
<213> ORGANISM: Human
<220> FEATURE:
<221> NAME/KEY: misc_feature
<223> OTHER INFORMATION: Nucleotides at positions 1, 3, 5, 7, 9, 11, 13,
      15, 17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 87
tctgcccatg tctccca                                                 17

<210> SEQ ID NO 88
<211> LENGTH: 17
<212> TYPE: DNA
<213> ORGANISM: Human
<220> FEATURE:
<221> NAME/KEY: misc_feature
```

```
<223> OTHER INFORMATION: Nucleotides at positions 1, 2, 7, 8, 9, 14, 15,
      16, 17 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 88
tctgcccatg tctccca                                                  17

<210> SEQ ID NO 89
<211> LENGTH: 20
<212> TYPE: DNA
<213> ORGANISM: Homo sapiens

<400> SEQUENCE: 89
tcagcagcgt ccgcagccag                                               20

<210> SEQ ID NO 90
<211> LENGTH: 19
<212> TYPE: DNA
<213> ORGANISM: Homo sapiens

<400> SEQUENCE: 90
ctgcctcctc ttcaacctg                                                19

<210> SEQ ID NO 91
<211> LENGTH: 19
<212> TYPE: DNA
<213> ORGANISM: Homo sapiens

<400> SEQUENCE: 91
ccatgatgcg gtctgtcca                                                19

<210> SEQ ID NO 92
<211> LENGTH: 17
<212> TYPE: DNA
<213> ORGANISM: Homo sapiens

<400> SEQUENCE: 92
tcatgagtgg cagctgc                                                  17

<210> SEQ ID NO 93
<211> LENGTH: 20
<212> TYPE: DNA
<213> ORGANISM: Human

<400> SEQUENCE: 93
tcaggccatg cactgttact                                               20

<210> SEQ ID NO 94
<211> LENGTH: 21
<212> TYPE: DNA
<213> ORGANISM: Human

<400> SEQUENCE: 94
cctgattctc tcaataagcc c                                             21

<210> SEQ ID NO 95
<211> LENGTH: 22
<212> TYPE: DNA
<213> ORGANISM: Human

<400> SEQUENCE: 95
caacagtgac agcagtgaca tt                                            22
```

```
<210> SEQ ID NO 96
<211> LENGTH: 22
<212> TYPE: DNA
<213> ORGANISM: Human

<400> SEQUENCE: 96
ttgagtccag gttatccatg ac                                          22

<210> SEQ ID NO 97
<211> LENGTH: 20
<212> TYPE: DNA
<213> ORGANISM: Human

<400> SEQUENCE: 97
gattctttgg gattgggact                                             20

<210> SEQ ID NO 98
<211> LENGTH: 20
<212> TYPE: DNA
<213> ORGANISM: Human

<400> SEQUENCE: 98
atctttggcc tacaggaacc                                             20

<210> SEQ ID NO 99
<211> LENGTH: 20
<212> TYPE: DNA
<213> ORGANISM: Human

<400> SEQUENCE: 99
atcaacacca attcggagct                                             20

<210> SEQ ID NO 100
<211> LENGTH: 19
<212> TYPE: DNA
<213> ORGANISM: Human

<400> SEQUENCE: 100
ccagcaccat gtcgatgac                                              19

<210> SEQ ID NO 101
<211> LENGTH: 20
<212> TYPE: DNA
<213> ORGANISM: Human

<400> SEQUENCE: 101
tggcagacct gaagacaatg                                             20

<210> SEQ ID NO 102
<211> LENGTH: 19
<212> TYPE: DNA
<213> ORGANISM: Human

<400> SEQUENCE: 102
aaattcctcc atgatgcgg                                              19

<210> SEQ ID NO 103
<211> LENGTH: 20
<212> TYPE: DNA
<213> ORGANISM: Human

<400> SEQUENCE: 103
cagaatatgg tgcactgtgc                                             20
```

<210> SEQ ID NO 104
<211> LENGTH: 21
<212> TYPE: DNA
<213> ORGANISM: Human

<400> SEQUENCE: 104
agtctatgaa gcccacctgt g                                              21

<210> SEQ ID NO 105
<211> LENGTH: 28
<212> TYPE: DNA
<213> ORGANISM: Human

<400> SEQUENCE: 105
atcagactga agagctttgt aatgacca                                        28

<210> SEQ ID NO 106
<211> LENGTH: 23
<212> TYPE: DNA
<213> ORGANISM: Human

<400> SEQUENCE: 106
tggcttatat ccaacacttc gtg                                            23

<210> SEQ ID NO 107
<211> LENGTH: 26
<212> TYPE: DNA
<213> ORGANISM: Human

<400> SEQUENCE: 107
caaggactgg tctttctatc tcttgt                                         26

<210> SEQ ID NO 108
<211> LENGTH: 22
<212> TYPE: DNA
<213> ORGANISM: Human

<400> SEQUENCE: 108
gtggagcaac ctgctcagat ac                                             22

<210> SEQ ID NO 109
<211> LENGTH: 19
<212> TYPE: DNA
<213> ORGANISM: Human

<400> SEQUENCE: 109
agagcatcta cggtgagcg                                                 19

<210> SEQ ID NO 110
<211> LENGTH: 17
<212> TYPE: DNA
<213> ORGANISM: Human

<400> SEQUENCE: 110
cttccgcacc acctcca                                                   17

<210> SEQ ID NO 111
<211> LENGTH: 20
<212> TYPE: DNA
<213> ORGANISM: Human

<400> SEQUENCE: 111
aagaatcatc atgtgcgctt                                                20

<210> SEQ ID NO 112
<211> LENGTH: 23
<212> TYPE: DNA
<213> ORGANISM: Human

<400> SEQUENCE: 112
gtgtgtataa agtcacctgg ctt                                          23

<210> SEQ ID NO 113
<211> LENGTH: 19
<212> TYPE: DNA
<213> ORGANISM: Homo sapiens

<400> SEQUENCE: 113
ggttgctcag atctgcaca                                               19

<210> SEQ ID NO 114
<211> LENGTH: 15
<212> TYPE: DNA
<213> ORGANISM: Homo sapiens

<400> SEQUENCE: 114
ttgctcagat ctgca                                                   15

<210> SEQ ID NO 115
<211> LENGTH: 21
<212> TYPE: DNA
<213> ORGANISM: Human
<220> FEATURE:
<221> NAME/KEY: misc_feature
<223> OTHER INFORMATION: Nucleotides at positions 1, 2, 3, 4, 10, 11,
      18, 19, 20, 21 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 115
tcatgagtgg cagctgcaat t                                            21

<210> SEQ ID NO 116
<211> LENGTH: 21
<212> TYPE: DNA
<213> ORGANISM: Human
<220> FEATURE:
<221> NAME/KEY: misc_feature
<223> OTHER INFORMATION: Nucleotides at positions 1, 2, 5, 6, 10, 11,
      12, 18, 19, 20, 21 are 2'-deoxy-2'-fluoroarabinonucleotides.
<220> FEATURE:
<221> NAME/KEY: misc_feature
<223> OTHER INFORMATION: All nucleotides are linked by phosphorothioate
      bonds.

<400> SEQUENCE: 116
tcatgagtgg cagctgcaat t                                            21

<210> SEQ ID NO 117
<211> LENGTH: 21
<212> TYPE: DNA
<213> ORGANISM: Human
<220> FEATURE:
<221> NAME/KEY: misc_feature
<223> OTHER INFORMATION: All nucleotides are linked by phosphorothioate
      bonds.
<220> FEATURE:
<221> NAME/KEY: misc_feature
<223> OTHER INFORMATION: Nucleotides at positions 1, 2, 3, 4, 5, 16, 17,
      18, 19, 20, 21 are 2'-deoxy-2'-fluoroarabinonucleotides.

```
<220> FEATURE:
<221> NAME/KEY: misc_feature
<222> LOCATION: (11)..(11)
<223> OTHER INFORMATION: Inosine

<400> SEQUENCE: 117
ggttgctcag ntctgcacag t                                              21

<210> SEQ ID NO 118
<211> LENGTH: 21
<212> TYPE: DNA
<213> ORGANISM: Human
<220> FEATURE:
<221> NAME/KEY: misc_feature
<223> OTHER INFORMATION: All nucleotides are linked by phosphorothioate
      bonds.
<220> FEATURE:
<221> NAME/KEY: misc_feature
<223> OTHER INFORMATION: Nucleotides at positions 1, 2, 17, 18, 19, 20,
      21 are 2'-deoxy-2'-fluoroarabinonucleotides.
<220> FEATURE:
<221> NAME/KEY: misc_feature
<222> LOCATION: (11)..(11)
<223> OTHER INFORMATION: Inosine

<400> SEQUENCE: 118
ggttgctcag ntctgcacag t                                              21

<210> SEQ ID NO 119
<211> LENGTH: 19
<212> TYPE: DNA
<213> ORGANISM: Human
<220> FEATURE:
<221> NAME/KEY: misc_feature
<223> OTHER INFORMATION: All nucleotides are linked by phosphorothioate
      bonds.
<220> FEATURE:
<221> NAME/KEY: misc_feature
<223> OTHER INFORMATION: Nucleotides at positions 1, 2, 15, 16, 17, 18,
      19 are 2'-deoxy-2'-fluoroarabinonucleotides.
<220> FEATURE:
<221> NAME/KEY: misc_feature
<222> LOCATION: (4)..(4)
<223> OTHER INFORMATION: Inosine
<220> FEATURE:
<221> NAME/KEY: misc_feature
<222> LOCATION: (13)..(13)
<223> OTHER INFORMATION: Inosine

<400> SEQUENCE: 119
attntacatc aangcaagt                                                 19

<210> SEQ ID NO 120
<211> LENGTH: 19
<212> TYPE: DNA
<213> ORGANISM: Human
<220> FEATURE:
<221> NAME/KEY: misc_feature
<223> OTHER INFORMATION: All nucleotides are linked by phosphorothioate
      bonds.
<220> FEATURE:
<221> NAME/KEY: misc_feature
<223> OTHER INFORMATION: Nucleotides at positions 1, 2, 7, 8, 9, 15, 16,
      17, 18, 19 are 2'-deoxy-2'-fluoroarabinonucleotides.
<220> FEATURE:
<221> NAME/KEY: misc_feature
<222> LOCATION: (4)..(4)
<223> OTHER INFORMATION: Inosine
<220> FEATURE:
<221> NAME/KEY: misc_feature
<222> LOCATION: (13)..(13)
<223> OTHER INFORMATION: Inosine

<400> SEQUENCE: 120
```
attntacatc aangcaagt                                                19

<210> SEQ ID NO 121
<211> LENGTH: 19
<212> TYPE: DNA
<213> ORGANISM: Human
<220> FEATURE:
<221> NAME/KEY: misc_feature
<223> OTHER INFORMATION: All nucleotides are linked by phosphorothioate
      bonds.
<220> FEATURE:
<221> NAME/KEY: misc_feature
<223> OTHER INFORMATION: Nucleotides at positions 1, 2, 3, 4, 5, 14, 15,
      16, 17, 18, 19 are 2'-deoxy-2'-fluoroarabinonucleotides.
<220> FEATURE:
<221> NAME/KEY: misc_feature
<222> LOCATION: (11)..(11)
<223> OTHER INFORMATION: Inosine

<400> SEQUENCE: 121
ggttgctcag ntctgcaca                                                19

<210> SEQ ID NO 122
<211> LENGTH: 19
<212> TYPE: DNA
<213> ORGANISM: Human
<220> FEATURE:
<221> NAME/KEY: misc_feature
<223> OTHER INFORMATION: All nucleotides are linked by phosphorothioate
      bonds.
<220> FEATURE:
<221> NAME/KEY: misc_feature
<223> OTHER INFORMATION: Nucleotides at positions 1, 2, 15, 16, 17, 18,
      19 are 2'-deoxy-2'-fluoroarabinonucleotides.
<220> FEATURE:
<221> NAME/KEY: misc_feature
<222> LOCATION: (11)..(11)
<223> OTHER INFORMATION: Inosine

<400> SEQUENCE: 122
ggttgctcag ntctgcaca                                                19

<210> SEQ ID NO 123
<211> LENGTH: 19
<212> TYPE: DNA
<213> ORGANISM: Human
<220> FEATURE:
<221> NAME/KEY: misc_feature
<223> OTHER INFORMATION: All nucleotides are linked by phosphorothioate
      bonds.
<220> FEATURE:
<221> NAME/KEY: misc_feature
<223> OTHER INFORMATION: Nucleotides at positions 1, 2, 7, 8, 9, 15, 16,
      17, 18, 19 are 2'-deoxy-2'-fluoroarabinonucleotides.
<220> FEATURE:
<221> NAME/KEY: misc_feature
<222> LOCATION: (11)..(11)
<223> OTHER INFORMATION: Inosine

<400> SEQUENCE: 123
ggttgctcag ntctgcaca                                                19

<210> SEQ ID NO 124
<211> LENGTH: 19
<212> TYPE: DNA
<213> ORGANISM: Human
<220> FEATURE:
<221> NAME/KEY: misc_feature
<223> OTHER INFORMATION: All nucleotides are linked by phosphorothioate
      bonds.
<220> FEATURE:
<221> NAME/KEY: misc_feature -continued

```
<223> OTHER INFORMATION: Nucleotides at positions 1, 2, 16, 17, 18, 19
      are 2'-deoxy-2'-fluoroarabinonucleotides.
<220> FEATURE:
<221> NAME/KEY: misc_feature
<222> LOCATION: (11)..(11)
<223> OTHER INFORMATION: Inosine

<400> SEQUENCE: 124
ggttgctcag ntctgcaca                                              19

<210> SEQ ID NO 125
<211> LENGTH: 19
<212> TYPE: DNA
<213> ORGANISM: Human
<220> FEATURE:
<221> NAME/KEY: misc_feature
<223> OTHER INFORMATION: All nucleotides are linked by phosphorothioate
      bonds.
<220> FEATURE:
<221> NAME/KEY: misc_feature
<223> OTHER INFORMATION: Nucleotides at positions 1, 2, 16, 17, 18, 19
      are 2'-deoxy-2'-fluoroarabinonucleotides.

<400> SEQUENCE: 125
ggttgctcag atctgcaca                                              19

<210> SEQ ID NO 126
<211> LENGTH: 15
<212> TYPE: DNA
<213> ORGANISM: Human
<220> FEATURE:
<221> NAME/KEY: misc_feature
<223> OTHER INFORMATION: All nucleotides are linked by phosphorothioate
      bonds.
<220> FEATURE:
<221> NAME/KEY: misc_feature
<223> OTHER INFORMATION: Nucleotides at positions 1, 2, 3, 13, 14, 15
      are 2'-deoxy-2'-fluoroarabinonucleotides.

<400> SEQUENCE: 126
ttgctcagat ctgca                                                  15
```

OLIGONUCLEOTIDES AFFECTING EXPRESSION OF PHOSPHODIESTERASES

CROSS REFERENCE TO RELATED APPLICATIONS

This application is the U.S. National Stage filing of International Application Serial No. PCT/CA2007/000902 filed May 18, 2007, which claims priority to U.S. Provisional Application No. 60/801,384 filed on May 19, 2006, each of which is incorporated herein by reference in its entirety.

FIELD OF THE INVENTION

The invention relates to methods, reagents and compositions of use for antisense oligonucleotide-based therapy. In particular, the invention relates the application of antisense oligonucleotide-based therapy in the treatment of diseases associated with reduced cAMP in a patient including, for example, PDE-related disease such as inflammatory conditions and cancer. The invention also relates to gene therapy methods and methods for identifying novel antisense-based strategy wherein cyclic AMP phosphodiesterases are involved.

BACKGROUND OF THE INVENTION

The alveolar and airway epithelium is recognized as a dynamic barrier that plays an important role in regulating inflammatory and metabolic responses to oxidative stress, sepsis, endotoxemia, and other critical illnesses in the lung. The respiratory epithelium, in particular, is a primary target of inflammatory conditions/infections at the epithelial-blood interface, and is itself capable of amplifying an inflammatory signal by recruiting inflammatory cells and producing inflammatory mediators.

Chronic Obstructive Pulmonary Disease (COPD) is one example of an inflammatory airway and alveolar disease where persistent upregulation of inflammation is thought to play a role. Inflammation in COPD is characterized by increased infiltration of neutrophils, CD8 positive lymphocytes, and macrophages into the airways. Neutrophils and macrophages play an important role in the pathogenesis of airway inflammation in COPD because of their ability to release a number of mediators including elastase, metalloproteases, and oxygen radicals that promote tissue inflammation and damage. It has been suggested that inflammatory cell accumulation in the airways of patients with COPD is driven by increased release of pro-inflammatory cytokines and of chemokines that attract the inflammatory cells into the airways, activate them and maintain their presence. The cells that are present also release enzymes (like metalloproteases) and oxygen radicals which have a negative effect on tissue and perpetuate the disease. A vast array of pro-inflammatory cytokines and chemokines have been shown to be increased within the lungs of patients with COPD. Among them, an important role is played by tumor necrosis factor alpha (TNF-alpha), granulocyte-macrophage colony stimulating factor (GM-CSF) and interleukin 8 (IL-8), which are increased in the airways of patients with COPD.

Other examples of respiratory diseases where inflammation seems to play a role include: asthma, eosinophilic cough, bronchitis, acute and chronic rejection of lung allograft, sarcoidosis, pulmonary fibrosis, rhinitis and sinusitis. Asthma is defined by airway inflammation, reversible obstruction and airway hyperresponsiveness. In this disease the inflammatory cells that are involved are predominantly eosinophils, T lymphocytes and mast cells, although neutrophils and macrophages may also be important. A vast array of cytokines and chemokines have been shown to be increased in the airways and play a role in the pathophysiology of this disease by promoting inflammation, obstruction and hyperresponsiveness.

Eosinophilic cough is characterized by chronic cough and the presence of inflammatory cells, mostly eosinophils, within the airways of patients in the absence of airway obstruction or hyperresponsiveness. Several cytokines and chemokines are increased in this disease, although they are mostly eosinophil directed. Eosinophils are recruited and activated within the airways and potentially release enzymes and oxygen radicals that play a role in the perpetuation of inflammation and cough.

Acute bronchitis is an acute disease that occurs during an infection or irritating event for example by pollution, dust, gas or chemicals, of the lower airways. Chronic bronchitis is defined by the presence of cough and phlegm production on most days for at least 3 months of the year, for 2 years. One can also find during acute or chronic bronchitis within the airways inflammatory cells, mostly neutrophils, with a broad array of chemokines and cytokines. These mediators are thought to play a role in the inflammation, symptoms and mucus production that occur during these diseases.

Lung transplantation is performed in patients with end stage lung disease. Acute and more importantly chronic allograft rejection occur when the inflammatory cells of our body, lymphocytes, do not recognize the donor organ as "self". Inflammatory cells are recruited by chemokines and cytokines and release a vast array of enzymes that lead to tissue destruction and in the case of chronic rejection a disease called bronchiolitis obliterans.

Sarcoidosis is a disease of unknown cause where chronic non-caseating granulomas occur within tissue. The lung is the organ most commonly affected. Lung bronchoalveolar lavage shows an increase in mostly lymphocytes, macrophages and sometimes neutrophils and eosinophils. These cells are also recruited and activated by cytokines and chemokines and are thought to be involved in the pathogenesis of the disease.

Pulmonary fibrosis is a disease of lung tissue characterized by progressive and chronic fibrosis (scarring) which will lead to chronic respiratory insufficiency. Different types and causes of pulmonary fibrosis exist but all are characterized by inflammatory cell influx and persistence, activation and proliferation of fibroblasts with collagen deposition in lung tissue. These events seem related to the release of cytokines and chemokines within lung tissue.

Acute rhinitis is an acute disease that occurs during an infection or irritating event, for example, by pollution, dust, gas or chemicals, of the nose or upper airways. Chronic rhinitis is defined by the presence of a constant chronic runny nose, nasal congestion, sneezing and pruritis. One can also find within the upper airways during acute or chronic rhinitis inflammatory cells with a broad array of chemokines and cytokines. These mediators are thought to play a role in the inflammation, symptoms and mucus production that occur during these diseases.

Acute sinusitis is an acute, usually infectious disease of the sinuses characterized by nasal congestion, runny, purulent phlegm, headache or sinus pain, with or without fever. Chronic sinusitis is defined by the persistence for more than 6 months of the symptoms of acute sinusitis. One can also find during acute or chronic sinusitis within the upper airways and sinuses inflammatory cells with a broad array of chemokines and cytokines. These mediators are thought to play a role in the inflammation, symptoms and phlegm production that occur during these diseases.

There is a growing body of evidence suggesting an intimate link between inflammation and neoplastic diseases. The tumor microenvironment is shaped by cells entering it, and their functions reflect the local conditions. Successive changes occurring at the tumor site during tumor progression resemble chronic inflammation. This chronic inflammatory reaction seems to be largely orchestrated by the tumor, and it seems to promote tumor survival. It has become evident that early and persistent inflammatory responses observed in or around developing neoplasms regulates many aspects of tumour development (matrix remodelling, angiogenesis, malignant potential) by providing diverse mediators implicated in maintaining tissue homeostasis, e.g., soluble growth and survival factors, matrix remodelling enzymes, reactive oxygen species and other bioactive molecules.

As described above, these inflammatory respiratory diseases or diseases in which inflammation plays a critical role are all characterized by the presence of mediators that recruit and activate different inflammatory cells which release enzymes or oxygen radicals causing symptoms, the persistence of inflammation and when chronic, destruction or disruption of normal tissue.

A logical therapeutic approach would be to downregulate cytokine and chemokine production and the inflammatory cell response. This has been performed in all the diseases described above by employing either topical or systemic corticosteroids with different levels of success. Corticosteroids are immune suppressive and have effects not only on inflammatory cells but also on other cells of the body that lead to toxicity when administered chronically.

Despite the availability of medications for COPD, asthma and other inflammatory respiratory diseases, the prevalence and morbidity of these diseases has remained stable or increased. It is obvious that there is an unmet medical need for the therapy of inflammatory respiratory diseases, and innovative therapeutic agents are urgently required. Antisense oligonucleotide-based therapy offers a new alternative approach to selectively decrease the expression of specific genes without the undesirable toxic effects of traditional therapeutic strategies. Antisense therapies are being investigated for the treatment of several diseases. It has been previously shown that antisense oligonucleotides directed against receptors for inflammatory mediators can be administered to the lungs and down-regulate their targets as described in WO9966037.

A therapeutic approach that would decrease pro-inflammatory cytokine and chemokine release by a vast array of cells while having a reduced effect on the release of anti-inflammatory mediators or enzymes may have an advantage over current therapies for inflammatory respiratory diseases or any other systemic inflammatory disease.

The cyclic nucleotides cAMP and cGMP are ubiquitous second messengers participating in signaling transduction pathways and mechanisms. Mammalian cells have evolved a complex and highly conserved complement of enzymes that regulate the generation and inactivation of cyclic nucleotides through multiple and complex feedforward and feedback mechanisms. Both cAMP and cGMP are formed from their respective triphosphates (ATP and GTP) by the catalytic activity of adenylyl (adenylate) or guanylyl (guanylate) cyclase, respectively as described in Essayan D. M. *Cyclic nucleotide phosphodiesterase (PDE) inhibitors and immunomodulation.* Biochem. Pharmacol., 1999, 57, 965-973. Inactivation of cAMP/cGMP is achieved by hydrolytic cleavage of the 3'-phosphodiester bond catalyzed by the cyclic-nucleotide-dependent phosphodiesterases (PDEs), resulting in the formation of the corresponding, inactive 5'-monophosphate as described in Essayan, 1999 and Perry M. J. and Higgs G. A. *Chemotherapeutic potential of phosphodiesterase inhibitors.* 1998, Curr Opin Chem Biol. 4:472-81.

It has been shown that the inflammatory response and its progression is exquisitely sensitive to modulations in the steady-state levels of cyclic nucleotides, where target cells for their effects extend beyond immune cells to include accessory cells, such as airway smooth muscle, epithelial and endothelial cells, and neurons as described in Perry and Higgs, 1998; Essayan, 1999. In this respect, the emerging concept that modulation of intracellular cyclic nucleotides plays a major role in regulating the inflammatory milieu has recently evolved into targeting and improving inflammatory/autoimmune responses. The cyclic nucleotide PDEs are a large, growing multigene family, comprising at least 11 families of PDE enzymes. The profile of selective and nonselective PDE inhibitors in vitro and in vivo, therefore, suggests a potential therapeutic utility as antidepressants, antiproliferative, immunomodulatory, tocolytics, inotropes/chronotropes, and cytoprotective agents.

Intracellular cAMP seems to have a fundamental role, not only in smooth muscle relaxation, activation and proliferation but also in the modulation of the release of mediators by inflammatory cells. Decreased cAMP levels can lead to increased production of inflammatory mediators such as TNF-alpha, GM-CSF, and IL-8 in airway epithelial cells.

Insight into the molecular mechanisms of the regulatory role of cytokines in cellular homeostasis as well as inflammatory/autoimmune/infectious diseases has begun to provide new approaches to design therapeutic strategies for pharmacological interventions. One such novel approach is the chemotherapeutic potential of PDE enzyme blockade, which revealed a phenomenal diversity and complexity scheme for promising therapeutics across a broad spectrum of disease states. One mechanistic understanding of PDE inhibition is centered on the immunomodulatory properties of cyclic nucleotides (cAMP/cGMP), thereby paving a channel through which anti-inflammatory, therapeutic applications could be clearly demonstrated.

The inflammatory response and its progression is exquisitely sensitive to modulations in the steady-state levels of cyclic nucleotides, where target cells for their effects extend beyond immune cells to include structural cells, such as epithelial, smooth muscle and endothelial cells, and neurons (Perry and Higgs, 1998; Essayan, 1999). Modulation of intracellular cyclic nucleotides plays a major role in regulating the inflammatory response. The cyclic nucleotide PDEs are a large, growing multigene family, comprising at least 11 families of PDE isoenzymes. PDEs differ in their tissue and cellular distribution as well as in their molecular and physicochemical characteristics including nucleotides and protein sequences, substrate specificity, inhibitor sensitivity, and cofactor requirements. Within different families, tissue specific isoforms are generated from the same gene by alternative mRNA splicing and differential promoter usage.

The cAMP-specific PDE4 enzyme family is one of the most extensively studied PDEs. Enzymes within this family are found in most pro-inflammatory and immune cells, where they play a key role in the regulation of cAMP metabolism. PDE4 enzymes are expressed in macrophages, neutrophils, cytotoxic CD8+ T cells, bronchial epithelial cells, and airway smooth muscle cells. Moreover, PDE4 inhibitors modulate inflammation in animal models of respiratory diseases, suggesting that PDE4 may represent a suitable target in a therapeutic based strategy for intervention with small molecule inhibitors. Anti-PDE4 drugs inhibit the hydrolysis of intracellular cAMP, which in turn provides bronchodilation and suppression of the inflammatory response. Selective PDE4 inhibitors such as cilomilast and roflumilast are active in animal models of neutrophil inflammation (Bundschuch D S et al. J. Pharmacol. Exp. Ther. 2001, 297: 280-290). Although the use of PDE4 inhibitors for the treatment of airway inflammation is under intensive clinical investigations, several inhibitors have been dropped because of their toxicity, dose-limiting side effects, of which nausea and vomiting are the most common physiological manifestations. Consequently, improving the therapeutic ratio of PDE4 inhibitors raised a major challenge that is still an important field of investigation.

Considering the distribution of enzymes in target tissues, with high activity of PDE3 and PDE4 in airway smooth muscle and inflammatory cells, selective inhibitors of these enzymes may add to the therapy of chronic airflow obstruction. Generally small molecule inhibitors have been focused on one or several PDE without assessing the potential detrimental effects of inhibiting all the isoenzymes of a PDE. For example it has been suggested that most of the toxicity attributed to the PDE4 antagonists will occur through inhibition of the PDE4 isotype D. In addition, as shown herein, inhibition of certain isoenzymes of PDEs does not decrease all pro-inflammatory mediators however, a combination of isotype specific oligonucleotides can lead to an effect that is much broader when the right combination of antisense oligonucleotides is employed.

The PDE3 family contains two different genes, PDE3A and PDE3B, which are cGMP-inhibited and display a high affinity towards cAMP. Each PDE3 gene codes for at least two splice isoforms. The PDE3A has been identified in smooth muscle, platelets and cardiac tissues. The PDE3B is most abundant in adipocytes and liver cells. However, initial data from clinical trials with selective PDE3 inhibitors or a combination with PDE4 inhibitors have been somewhat disappointing and have tempered the expectations considerably since these drugs had limited efficacy and their use was clinically limited through side effects.

PDE7 was first isolated from a human glioblastoma. PDE7A codes for a cAMP-specific PDE that is insensitive to cGMP and inhibitors of PDE3 and PDE4 and has an amino acid sequence distinct from other cAMP PDEs. In humans two genes (PDE7A and PDE7B) have been characterized. The PDE7A gene codes for three isoenzymes (PDE7A1, PDE7A2, and PDE7A3) derived from the same gene by alternative mRNA splicing. In humans, PDE7A2 mRNA is expressed abundantly in skeletal muscle, heart, and kidney, whereas the testis, lung, and immune system (thymus, spleen, lymph node, blood leukocytes) are rich sources of PDE7A1. In addition, activated, but not naïve, human T lymphocytes express the splice variant PDE7A3. In contrast, PDE7B exists as a single isoenzyme in humans, it shares ~70% sequence similarity to PDE7A, but distinct kinetic properties. PDE7B is expressed predominantly in the brain and in a number of other tissues including liver, heart, thyroid glands, and skeletal muscle. Stimulation of human naïve T cells with anti-CD3 and anti-CD28 antibodies has been shown to promote IL-2 production and clonal amplification. These effects were attributed to PDE7A and down regulation of this enzyme prevents lymphocyte proliferation (Li L et al., Science, 1999, 283, 848-851).

The PDE4 family contains 4 different genes (PDE4 A-D). Due to alternative splicing of the genes, multiple splice variants are reported and classified into two main groups, the long and the short forms. PDE4A, B and D gene products are found in most immune and inflammatory cells. These are present either constitutively or after activation as described in Burnouf C. and Pruniaux M. P. Current Pharmaceutical Design 2002; 8:1255-1296. Inhibition of all or certain isotypes of PDE4 is associated with downregulation of several inflammatory mediators; however, an increase in certain pro-inflammatory cytokines (e.g. IL-6) has been described (Giembycz M. A. Expert Opin Invest Drugs 2001, 10:1361-1379).

It would therefore be desirable to inhibit all three PDE enzymes; however this approach may be plagued by the toxicity that has been described with administration of inhibitors of each of these enzymes. The topical application of antisense oligonucleotides could circumvent the systemic toxicity of enzyme inhibition but there appear to be too many isoenzymes of these PDE for this approach to be practical. Inhibition of one or several isotypes of PDE enzymes may not be as effective as full PDE inhibition since other isotypes would be present to have their pro-inflammatory effects.

It would therefore appear desirable to seek a way to downregulate pro-inflammatory mediators and their cells while affecting less anti-inflammatory mediators or inhibitory enzymes for the therapy of inflammatory respiratory diseases. The therapeutic application of a combination of antisense oligonucleotides directed against selected isotypes of PDE enzymes is therefore herein proposed as a therapy for inflammatory respiratory diseases or any disease where increased cyclic AMP plays a role.

SUMMARY OF THE INVENTION

The present invention provides antisense oligonucleotide compounds that are effective at down-regulating PDE isotype genes that they are directed against as well as selected antisense oligonucleotide compounds that are effective at downregulating not only the PDE isotype genes they are directed against but also other related genes including other PDE isotype genes, inflammatory and mitogenic genes.

In another aspect, the present invention provides a composition comprising at least 2 antisense oligonucleotide compounds, each antisense oligonucleotide compound being capable of downregulating a different gene. In some embodiments of this aspect, the combination of the at least 2 antisense oligonucleotide compounds leads to a significant downregulation of each the genes that is more than the additive ability of each antisense to downregulate each gene individually. In further embodiments, the present invention also provides a composition comprising at least 2 antisense oligonucleotide compounds, each antisense oligonucleotide compound being capable of downregulating a different gene, each antisense oligonucleotide compound being present at a concentration at which the antisense oligonucleotide compound is practically ineffective on its own to downregulate the gene it is directed against, the combination of the at least 2 antisense oligonucleotide compounds leading to a significant downregulation of each of the genes that the antisense oligonucleotide compounds are directed against and optionally other related genes. In still further embodiments of this aspect of the present invention, there is provided a composition comprising a combination of at least two antisense oligonucleotide compounds each directed against a different PDE target gene and each being effective to downregulate or inhibit a PDE target gene, each oligonucleotide compound being present in the combination at a concentration at which it exhibits less than 20% inhibition of its target gene, the combination of the oligonucleotide compounds exhibiting more than 20% inhibition and at least doubling the inhibition of at least one of the target genes.

The present invention further provides an antisense oligonucleotide effective in the compositions and methods of the present invention having a sequence selected from the group consisting of Seq. ID No. 1 to 92 and 113 to 126.

The present invention further provides pharmaceutical compositions comprising a pharmaceutically acceptable carrier and an oligonucleotide of the present invention or a combination of at least two antisense oligonucleotides as described above. The present invention also provides for the use of such compositions in the treatment and/or prevention of inflammatory respiratory diseases and other inflammation-related diseases.

The combinations of the present invention appear to exert an inhibitory action by an approach that has been termed multiple gene knock down. Multiple gene knock down encompasses situations in which:

1) an antisense oligonucleotide downregulates not only the gene that it is directed against but also downregulates other related genes; and/or 2) a combination of at least 2 antisense oligonucleotides, each present at a concentration at which the antisense oligonucleotide is practically ineffective to downregulate the gene it is directed against on its own, the combination leading to significant downregulation of both genes that the antisense oligonucleotides are directed against and optionally other related genes.

The present invention uses the above approach to provide methods, compositions and kits for treating and/or preventing disease associated with reduced cAMP in a patient, including PDE-related disease, inflammatory disease including respiratory diseases and more particularly COPD and asthma, and other diseases in which inflammation plays an important role including cancer.

The invention also provides methods, reagents and compositions for reducing the expression and consequently the activity of cell cyclic-AMP phosphodiesterases and thereby maintaining the correct balance of intracellular c-AMP and cytokine/chemokine production.

The invention further provides methods and tools for identifying/screening in vitro, in vivo and ex vivo, combinations of novel antisense oligonucleotide compounds, drugs and vaccines that are capable of interfering with PDE expression and elevating the intracellular c-AMP level.

The present invention also provides gene-based therapy and transfection methods in which one or more antisense oligonucleotide compounds are used for cell transfection or delivered to humans and animals for interfering with PDE isotype gene expression.

The present invention further provides antisense oligonucleotides effective against PDE3 isotypes, such as PDE3A and PDE3B; PDE4 isotypes such as PDE4A, PDE4B and PDE4D and PDE7 isotypes such as PDE7A, among other PDEs.

According to another broad aspect of the invention, a method is provided for increasing at least one of nuclease stability and target gene inhibition activity of an antisense oligonucleotide comprising replacing at least one nucleotide of the oligonucleotide with an arabinose modified nucleotide, preferably 2'-deoxy-2'-fluoroarabinonucleotide (FANA).

Other objects and advantages of the present invention will be apparent upon reading the following non-restrictive description of several preferred embodiments made with reference to the accompanying drawings.

BRIEF DESCRIPTION OF THE DRAWINGS

The present invention will now be described in greater detail having regard to the appended drawings in which:

FIG. 4 shows the potency of 2' F-ANA-containing AON at inhibiting target gene expression. A549 cells transfected for 24 h with PDE4D-specific AON composed of PS-DNA or composed with PS-FANA modification or corresponding mismatch sequences using Lipofectamine™ 2000 (Invitrogen, 1 ug AON: 1 uL Lipofectamine™ 2000) at indicated doses (A). PDE4D mRNA expression level of target genes was quantified using Quantigene® assay (Panomics) and was normalized to β2M gene expression. Data expressed as specific % inhibition relative to expression level in cells treated with the sense control sequence. A549 cells transfected with for 24 h with PDE4D-specific AON composed of PS-DNA or composed with PS-FANA modifications or corresponding mismatch sequences using Lipofectamine™ 2000 (Invitrogen, 1 ug AON: 1 uL Lipofectamine™ 2000) with a single dose for different time points (8, 24, or 48 h) (B). PDE4D mRNA expression level of target genes was quantified using the Quantigene® assay (Panomics) and was normalized to β2M gene expression. Data expressed as specific % inhibition relative to expression level in cells treated with the sense control sequence. Legend below figure demonstrates FANA modifications in the TOP 1497 (PDE4-specific) AON. Sequences TOP1497, TOP1497-F1, TOP1497-F2, and TOP1497-F6 correspond to SEQ ID NO:90, SEQ ID NO:72, SEQ ID NO:76, and SEQ ID NO:77, respectively.

FIG. 9 shows the efficacy of TOP1572-F2 and TOP1545 at reducing (A) PDE4D mRNA expression and (B) MCP-1 protein secretion in normal human bronchial epithelial cells (NHBE). Cells were transfected for 24 h with 250 nM of AON or corresponding control complexed to Lipofectamine™ 2000 at ratio 1 ug oligo:1 uL lipid in antibiotic free media. Cells were stimulated for 4 h with cytomix (500 U/mL TNF-α+10 ng/mL IL1-β+10 ng/mL IFNγ) at the end of the transfection period. MCP-1 protein secretion was measured in supernatant by ELISA, with normalization to the cell viability as measured by AlamarBlue assay. PDE4D, mRNA expression level was measured by RT-PCR with relative quantification to the expression of B2M control gene. Percentage of inhibition was determined relative to cells treated with the corresponding control. Statistical analysis was performed using t test, *p<0.05, ***p<0.001.

FIG. 13 compares the efficacy of TOP1572 (PS-DNA) to the efficacy of TOP1572-F1, TOP1572-F2 and TOP1572-F3 (PS-FANA versions) at reducing (A) PDE4D and (B) PDE4B mRNA expression in the 293 cell line. Cells were transfected for 24 h, 48 h or 72 h with 250 nM of AON or corresponding control complexed to Lipofectamine™ 2000 at ratio 1 ug oligo:1 uL lipid in antibiotic free media. PDE4D and PDE4B mRNA expression levels were measured by RT-PCR with relative quantification to the expression of PPIB control gene. Percentage of specific PDE mRNA inhibition was determined relative to the gene level in cells transfected with the corresponding control.

BRIEF DESCRIPTION OF THE TABLES

Figure 1B:
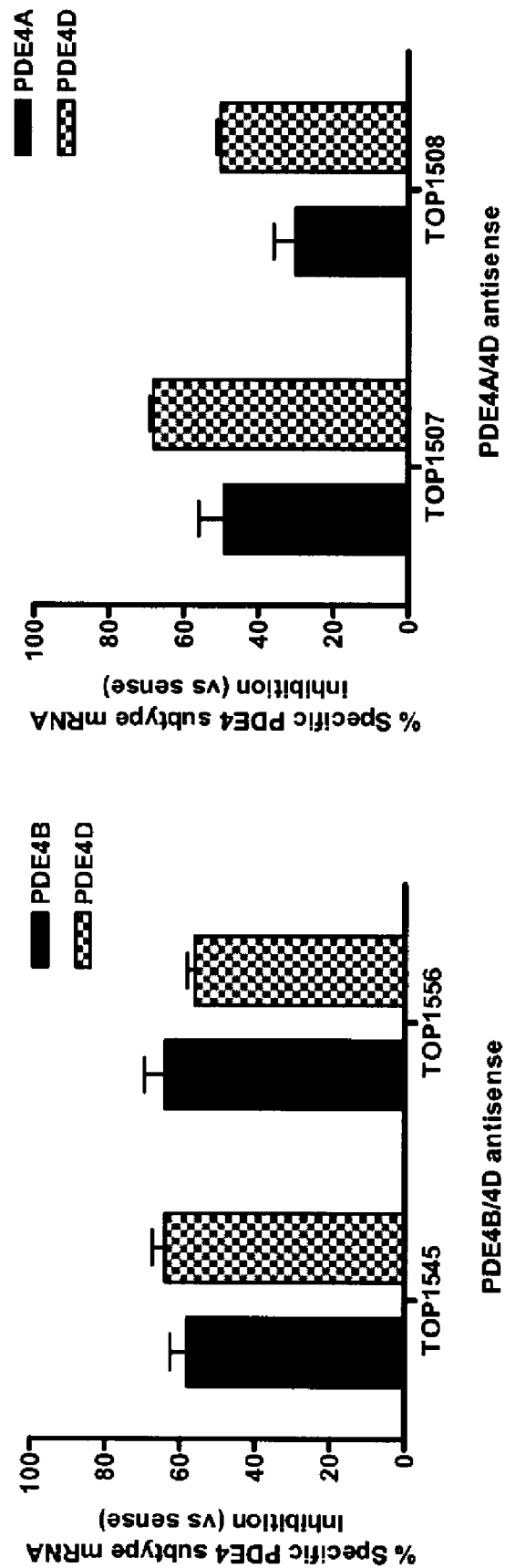
FIG. 1 shows the efficacy of different AON at inhibiting their specific target knockdown. (A) A549 cells were transfected with specific AON targeting PDE3A, PDE3B, PDE7A, PDE4A, PDE4B or PDE4D for 24 h using Lipofectamine™ 2000 (Invitrogen, ratio 1 ug oligonucleotide:1 uL Lipofectamine™ 2000) and 200 ng to 400 ng of AON (AS) or the corresponding mismatch sequence (Mi/Sense). PDE3B, PDE4A and PDE4B mRNA expression levels were quantified using the Quantigene® assay (Panomics). Real-time PCR was used to quantify PDE3A, PDE7A and PDE4D expression. PDE expression was normalized to the expression of a control gene (β2M, Ppib or HPRT). Data expressed as mean % inhibition relative to expression level in untreated cells. ($p<0.01$, *$p<0.001$, n=3). (B) 293 cells transfected overnight with AON that targets more than one PDE4 isoform. PDE4 isoform mRNA expression level was quantified using real-time PCR and normalized to the expression of the control gene β2M. Data expressed as mean % inhibition relative to expression level of cells transfected with relevant sense or mismatch AON.

Table 1a identifies human PDE7A antisense oligonucleotides in accordance with the present invention.

Table 1b identifies human PDE3A antisense oligonucleotides in accordance with the present invention.

Table 1c identifies antisense oligonucleotides with dual specificity against more than one PDE4 isoform (either PDE4A/4D or PDE4B/4D) in accordance with the present invention. Base pair mismatches between PDE4 isoforms in AON sequences are indicated in underline. Replacement of base pairs with inosine in AON indicated by letter I.

Table 1d identifies antisense oligonucleotides with specificity against PDE 3B, PDE4D and PDE7A and dual specificity against PDE4A and 4B.

Table 2a identifies human PDE7A antisense oligonucleotides containing FANA bases in accordance with the present invention. FANA modified bases indicated by bold lettering.

Table 2b identifies human PDE3A antisense oligonucleotides containing FANA bases in accordance with the present invention. FANA modified bases indicated by bold lettering.

Table 2c identifies human PDE3B antisense oligonucleotides containing FANA bases in accordance with the present invention. FANA modified bases indicated by bold lettering.

Table 2d identifies human PDE4A antisense oligonucleotides containing FANA bases in accordance with the present invention. FANA modified bases indicated by bold lettering.

Table 2e identifies human PDE4D antisense oligonucleotides containing FANA bases in accordance with the present invention. FANA modified bases indicated by bold lettering.

Table 2f identifies human PDE4B antisense oligonucleotides containing FANA bases in accordance with the present invention. FANA modified bases indicated by bold lettering.

Table 2g identifies human antisense oligonucleotides with dual specificity against more than one PDE4 isoform and containing FANA bases in accordance with the present invention. FANA modified bases indicated by bold lettering.

Table 3 shows human oligonucleotide primers used in real-time PCR.

DETAILED DESCRIPTION

The invention herein relates to antisense oligonucleotide-based compounds, therapeutic compositions and methods for the treatment of disease associated with reduced cellular cAMP and/or disease associated with elevated levels of at least one PDE. The invention is aimed at increasing the level of cAMP in cells, while decreasing the level of pro-inflammatory mediators as well as enzymes that are released by inflammatory cells.

To obtain these effects, the present invention utilizes, in one of its aspects, what is herein referred to as "multiple gene knock down". Multiple gene knock down refers to the inhibition or downregulation of multiple genes by either a single antisense oligonucleotide compound in accordance with the present invention which downregulates not only the isoenzyme gene that it is directed against but also a related gene(s), or by a combination of at least two antisense oligonucleotide compounds which each downregulate a different isoenzyme gene.

Diseases associated with reduced levels of cellular cAMP include diseases in which there is increased levels of at least one cAMP-specific PDE (i.e. a PDE-related disease).

The term "downregulate" is used herein to refer to at least partial inhibition of the expression of a gene. In accordance with the invention, an antisense oligonucleotide compound downregulates or inhibits a gene that it is directed against, i.e. a gene to which the antisense oligonucleotide compound exhibits sequence complementarity sufficient to cause inhibition.

The term "related genes" refers to other genes that may also play a role in the pathophysiology of disease associated with reduced cellular cAMP and/or increased levels of at least one PDE but to which the oligonucleotide antisense compound is not complementary, either completely or partially. Such genes include, but are not limited to, genes that encode PDE enzymes or isotypes, mediators, for example, cytokines and chemokines and genes that encode enzymes. Examples of mediators include IL-2, IL-6, IL-7, IL-8, IL-15 and TNF-alpha. Examples of appropriate enzymes include, but are not limited to, matrix metalloproteinases (MMPs), such as MMP-1, MMP-2, MMP-3, MMP-9 and MMP-12.

In accordance with the present invention, antisense oligonucleotide (AON) compounds are herein defined as oligonucleotides, naturally occurring or modified, preferably nuclease resistant, that exhibit a complementarity to DNA or mRNA coding for a particular target protein such that they are capable of interfering with the transcription or translation of the mRNA and/or induce RNase or RNase-like activity and thereby function to reduce expression of the target protein. Expression of the target protein is reduced when the oligonucleotide compound hybridizes to the target DNA or mRNA, thereby interfering/preventing its transcription/translation. The present oligonucleotide compounds, thus, must be sufficiently complementary to the nucleic acid to which it is directed in order to hybridize thereto. Thus, although in a most preferred embodiment, the oligonucleotide compounds are 100% complementary to the nucleic to which they are directed, 100% complementarity is not necessary for hybridization to occur between an oligonucleotide compound and the nucleic acid to which it is directed, as one of skill will appreciate. As such, in some embodiments the oligonucleotide compounds may be about 95%, 90%, 85%, 80%, 75%, 70%, 60% and 50% complementary to the nucleic to which they are directed.

The terms "nucleic acid" and "nucleic acid molecule" as used interchangeably herein, refer to a molecule comprised of nucleotides, i.e., ribonucleotides, deoxyribonucleotides, or both. The term includes monomers and polymers of ribonucleotides and deoxyribonucleotides, with the ribonucleotide and/or deoxyribonucleotides being connected together, in the case of the polymers, via 5' to 3' linkages. However, linkages may include any of the linkages known in the nucleic acid synthesis art including, for example, nucleic acids comprising 5' to 2' linkages. The nucleotides used in the nucleic acid molecule may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, and the like.

The invention herein also relates to modifications to an antisense oligonucleotide(s) that do not significantly adversely effect their activity to reduce or inhibit expression of a target protein, but which may enhance this activity.

The present antisense oligonucleotide compounds may also be modified by insertion or deletion of 1 or more bases without significant adverse effect to their activity. In particular, the addition or deletion of bases at the terminal ends of the oligonucleotides that exhibit 100% complementation to the gene they are directed against can generally be made without significant loss of inhibitory activity. Such modifications may be made in order to increase activity or to provide enhanced stability of the oligonucleotide. In addition, substitution of 1 or more bases in the present antisense oligonucleotide compounds may also be made without adverse effect to activity, for example, substitution of purine with another purine (adenine, guanine) and pyrimidine with pyrimidine (cytosine, thymine, uracil).

Antisense oligonucleotide compounds in accordance with the present invention also include siRNAs (small interfering RNAs) and the RISCs (RNA-induced silencing complexes) containing them that result from the RNAi (RNA interference) approach. The RNA interference (RNAi) approach, which has been described recently, is considered as a new tool for the inhibition of target gene expression. As already known some years ago, RNAi is based on an ancient anti-viral defense mechanism in lower eukaryotes. It is induced by double-stranded RNA and its processing to 21-23 nt small interfering RNAs (siRNAs), which cause the degradation of homologous endogenous mRNA after hybridizing to the target mRNA in a single stranded fashion with the assistance of the RISC complex. The way RNAi works is still to be fully elucidated, but it already serves as a first-choice approach to generate loss-of-function phenotypes among a broad variety of eukaryotic species, such as nematodes, flies, plants, fungi and mammals.

Antisense oligonucleotide compounds in accordance with the present invention also include ribozymes and short nucleotide sequences, single or double stranded, RNA or DNA, which may incorporate chemical modifications as described above, capable of inhibiting gene transcription and/or translation in vitro and/or in vivo.

The compositions and methods of the present invention, in one aspect, while not to be bound by a particular mode of action, appear to act by a mechanism that has been termed "multiple gene knock down". Multiple gene knock down in the context of the present invention refers to:

1) an antisense oligonucleotide compound that downregulates not only the gene that it is directed against but also downregulates other related genes; and 2) a combination of at least 2 antisense oligonucleotide compounds each capable of downregulating a gene, each being present at a concentration at which the antisense oligonucleotide compound is practically ineffective on its own to downregulate a gene it is directed against, the combination leading to significant downregulation of both genes that the antisense oligonucleotides are directed against and may also downregulate other related genes. This effect was initially disclosed in applicant's PCT Published Application No: WO05/030787.

In one aspect, the present invention provides a composition comprising at least 2 antisense oligonucleotide compounds, each antisense oligonucleotide compound being capable of downregulating a different gene. In some embodiments of this aspect, the combination of the at least 2 antisense oligonucleotide compounds leads to a significant downregulation of each the genes that is more than the additive ability of each antisense to downregulate each gene individually.

In one aspect, the present invention provides a pharmaceutical composition for treating and/or preventing disease associated with reduced cellular cAMP and/or elevated levels of at least one PDE, said composition comprising a pharmaceutically acceptable carrier and at least two antisense oligonucleotide compounds, each oligonucleotide compound being directed against at least a portion of a different target PDE-encoding gene, each oligonucleotide compound being capable of downregulating the target gene it is directed against, each oligonucleotide compound being present at a concentration at which it exhibits less than 20% inhibition of its target PDE gene, the combination exhibiting greater than 20% inhibition and at least doubling the inhibition of at least one of the target genes and optionally other related genes.

As one of skill in the art will appreciate, the combination of oligonucleotide compounds in accordance with the present invention at very low concentrations, for example, concentrations with exhibit less than 1% inhibition of a target PDE gene, may not combine to exhibit an inhibition of at least 20%. The lowest concentration at which each oligonucleotide compound can be used to form a combination in accordance with the present invention will vary, and this concentration may be that at which 0.5% inhibition is achieved, or that concentration at which 1% to 5% inhibition is achieved. The present invention provides a pharmaceutical composition for treating and/or preventing a disease associated with reduced cellular cAMP and/or elevated levels of at least one PDE, said composition comprising a pharmaceutically acceptable carrier and at least two antisense oligonucleotides that are each capable of downregulating a different target gene, at least one of the oligonucleotides being present at a concentration at which it is practically ineffective on its own, e.g. a concentration exhibiting less than 20% inhibition of the target gene, the combination of the oligonucleotides exhibiting more than 20% inhibition and at least doubling the inhibition of at least one of the target genes. and optionally other related genes.

The present invention further provides the use of a combination of at least two antisense oligonucleotide compounds for treating and/or preventing disease associated with reduced cellular cAMP, such as respiratory inflammatory disease, each oligonucleotide compound being directed against a gene coding for a different PDE isotype, each oligonucleotide compound being capable of downregulating the gene it is directed against, the oligonucleotide compounds being present at a concentration at which each oligonucleotide is practically ineffective on its own to downregulate the gene it is directed against, the combination of the at least two oligonucleotide compounds being effective to downregulate at least one of the genes the oligonucleotide compounds are directed against and optionally other related genes.

The present invention further provides a method of treating and/or preventing disease associated with reduced cellular cAMP, such as inflammatory respiratory disease, the method comprising administering to a subject at least two antisense oligonucleotide compounds each being capable of downregulating a different target PDE gene, the oligonucleotide compounds being administered at a concentration at which each oligonucleotide compound is practically ineffective on its own to downregulate its target gene, for example, a concentration exhibiting less than 20% inhibition of the target gene, the combination of the oligonucleotide compounds being effective to downregulate at least one of the genes the oligonucleotide compounds are directed against and optionally other related genes.

The present invention further provides the use of a pharmaceutical composition as described above for the manufacture of a medicament for the treatment and/or prevention of a disease associated with reduced cellular cAMP or increased cAMP-specific PDE levels (PDE-related disease) such as inflammatory disease and cancer. Inflammatory disease to which the present methods and compositions are directed is generally defined as diseases in which inflammatory cells and/or mediators are present. Examples of inflammatory diseases include, but are not limited to, multiple sclerosis, contact dermatitis, allergic and non-allergic eye diseases, rheumatoid arthritis, septic shock, osteoporosis and cognitive disorders. Inflammatory respiratory disease to which the present methods and compositions are directed is generally defined as diseases of the respiratory tract and lungs in which inflammatory cells and mediators are present. Examples of inflammatory respiratory disease include, but are not limited to, COPD, asthma, eosinophilic cough, bronchitis, acute and chronic rejection of lung allograft, sarcoidosis, pulmonary fibrosis, rhinitis and sinusitis.

The present invention further provides the use of a pharmaceutical composition as described above for the manufacture of a medicament for the treatment and/or prevention of a disease where decreased cyclic AMP is involved in the physiopathology.

The present invention further provides methods for modifying antisense oligonucleotides so that it may reach the target nucleotide and/or be more effective against the target gene for the treatment and/or prevention of inflammatory respiratory diseases.

The present invention further provides a formulation, including the composition described above, the formulation being systemic and/or topical.

The present invention further provides an in vivo method of delivering a pharmaceutical composition to a target polynucleotide, comprising administering to a subject the composition as described above in combination with a surfactant that permits the composition to reach the target gene(s).

Preferably, the subjects or patients that may be treated using the antisense oligonucleotide compounds of the present invention include, but are not limited to, invertebrates, vertebrates, birds, mammals such as pigs, goats, sheep, cows, dogs, cats, and particularly humans. Oligonucleotide compounds in accordance with the present invention are designed to be appropriate to the particular animal to be treated. In particular, the sequence of the antisense oligonucleotide compounds will vary with the subject being treated given interspecies genome differences.

The present invention further provides antisense oligonucleotides effective against, e.g. capable of inhibiting the expression of, the PDE family of enzymes, including, but not limited to, PDE3, PDE4 and PDE7. As will be appreciated by one of skill in the art, each PDE subtype may also includes isotypes. For example, PDE3 subtype include the PDE3A and PDE3B isotypes; the PDE4 subtype includes isotypes PDE4A, PDE4B, PDE4C and PDE4D; and the PDE7 subtype includes isotypes PDE7A1, PDE7A2, PDE7A3 and PDE7B.

When used herein the term "concentration at which the antisense oligonucleotide compound is practically ineffective" refers to the use of each oligonucleotide compound, when taken alone, at a concentration at which practically no downregulation is observed for the gene against which the oligonucleotide compound is directed (at a concentration at which less than 20% inhibition of the target gene is exhibited). This is in contrast to the effect of the combination of at least two oligonucleotide compounds in accordance with the present invention, each present at a concentration at which they are ineffective alone to downregulate the gene they are directed against (at a concentration at which less than 20% inhibition is exhibited), this combination exhibiting greater than 20% inhibition and being effective to at least double the inhibition of at least one of the genes against which the oligonucleotide compounds are directed.

The term "oligonucleotide" as used herein refers to a nucleic acid molecule comprising from about 1 to about 100 nucleotides, more preferably from 1 to 80 nucleotides, and even more preferably from about 4 to about 35 nucleotides. The term "oligonucleotide" also includes modified oligonucleotides and oligonucleotide compounds as set out above.

The terms "modified oligonucleotide" and "modified nucleic acid molecule" as used herein refer to nucleic acids, including oligonucleotides, with one or more chemical modifications at the molecular level of the natural molecular structures of all or any of the nucleic acid bases, sugar moieties, internucleoside phosphate linkages, as well as molecules having added substituents, such as diamines, cholesteryl or other lipophilic groups, or a combination of modifications at these sites. The internucleoside phosphate linkages can be phosphodiester, phosphotriester, phosphoramidate, siloxane, carbonate, carboxymethylester, acetamidate, carbamate, thioether, bridged phosphoranidate, bridged methylene phosphonate, phosphorothioate, methylphosphonate, phosphorodithioate, bridged phosphorothioate and/or sulfone internucleotide linkages, or 3'-3', 2'-5' or 5'-5' linkages, and combinations of such similar linkages (to produce mixed backbone modified oligonucleotides). The modifications can be internal (single or repeated) or at the end(s) of the oligonucleotide molecule and can include additions to the molecule of the internucleoside phosphate linkages, such as cholesteryl, diamine compounds with varying numbers of carbon residues between amino groups and terminal ribose, deoxyribose and phosphate modifications which cleave or cross-link to the opposite chains or to associated enzymes or other proteins. Electrophilic groups such as ribose-dialdehyde may be covalently linked with an epsilon amino group of the lysyl-residue of such a protein. A nucleophilic group such as n-ethylmaleimide tethered to an oligomer could covalently attach to the 5' end of an mRNA or to another electrophilic site. The term modified oligonucleotides also includes oligonucleotides comprising modifications to the sugar moieties such as 2'-substituted ribonucleotides, or deoxyribonucleotide monomers, any of which are connected together via 5' to 3' linkages. Modified oligonucleotides may also be comprised of PNA or morpholino modified backbones where target specificity of the sequence is maintained.

Optionally, the presently described oligonucleotides may be formulated with a variety of physiological carrier molecules. The presently described oligonucleotides may also be complexed with molecules that enhance their ability to enter the target cells. Examples of such molecules include, but are not limited to, carbohydrates, polyamines, amino acids, peptides, lipids, and molecules vital to cell growth. For example, the oligonucleotides may be combined with a lipid, the resulting oligonucleotide/lipid emulsion, or liposomal suspension may, inter alia, effectively increase the in vivo half-life of the oligonucleotide.

Alternatively, oligonucleotides directed at PDE targets may also be protonated/acidified to function in a dual role as phosphodiesterase inhibitors and antibacterial agents. Accordingly, another embodiment of the presently described invention is the use of a PDE modulating therapeutic oligonucleotide that is additionally protonated/acidified to increase cellular uptake, improve encapsulation in liposomes, so it can also serve as an antibiotic. Additionally, the oligonucleotide may be complexed with a variety of well established compounds or structures that, for instance, further enhance the in vivo stability of the oligonucleotide, or otherwise enhance its pharmacological properties (e.g., increase in vivo half-life, reduce toxicity, etc.).

The term "nucleic acid backbone" as used herein refers to the structure of the chemical moiety linking nucleotides in a molecule. This may include structures formed from any and all means of chemically linking nucleotides. A modified backbone as used herein includes modifications to the chemical linkage between nucleotides, as well as other modifications that may be used to enhance stability and affinity, such as modifications to the sugar structure. For example an [alpha]-anomer of deoxyribose may be used, where the base is inverted with respect to the natural [beta]-anomer. In a preferred embodiment, the 2'-OH of the sugar group may be altered to 2'-O-alkyl or 2'-O-alkyl-n(O-alkyl), which provides resistance to degradation without comprising affinity.

The term "acidification" and "protonation/acidification" as used interchangeably herein refers to the process by which protons (or positive hydrogen ions) are added to proton acceptor sites on a nucleic acid. The proton acceptor sites include the amine groups on the base structures of the nucleic acid and the phosphate of the phosphodiester linkages. As the pH is decreased, the number of these acceptor sites which are protonated increases, resulting in a more highly protonated/acidified nucleic acid.

The term "protonated/acidified nucleic acid" refers to a nucleic acid that, when dissolved in water at a concentration of approximately 16 A260 per ml, has a pH lower than physiological pH, i.e., lower than approximately pH 7. Modified nucleic acids, nuclease-resistant nucleic acids, and antisense nucleic acids are meant to be encompassed by this definition. Generally, nucleic acids are protonated/acidified by adding protons to the reactive sites on a nucleic acid, although other modifications that will decrease the pH of the nucleic acid can also be used and are intended to be encompassed by this term.

The term "end-blocked" as used herein refers to a nucleic acid with a chemical modification at the molecular level that prevents the degradation of selected nucleotides, e.g., by nuclease action. This chemical modification is positioned such that it protects the integral portion of the nucleic acid, for example the coding region of an antisense oligonucleotide. An end block may be a 3' end block or a 5' end block. For example, a 3' end block may be at the 3'-most position of the molecule, or it may be internal to the 3' ends, provided it is 3' of the integral sequences of the nucleic acid.

The term "substantially nuclease resistant" refers to nucleic acids that are resistant to nuclease degradation, as compared to naturally occurring or unmodified nucleic acids. Modified nucleic acids of the invention are at least 1.25 times more resistant to nuclease degradation than their unmodified counterpart, more preferably at least 2 times more resistant, even more preferably at least 5 times more resistant, and most preferably at least 10 times more resistant than their unmodified counterpart. Such substantially nuclease resistant nucleic acids include, but are not limited to, nucleic acids with modified backbones such as phosphorothioates, methylphosphonates, ethylphosphotriesters, 2'-0-methylphosphorothioates, 2'-O-methyl-p-ethoxy ribonucleotides, 2'-O-alkyls, 2'-O-alkyl-n(O-alkyl), 3'-O-alkyls, 3'-O-alkyl-n(O-alkyl), 2'-fluoros, 2'-deoxy-erythropentofuranosyls, 2'-O-methyl ribonucleosides, methyl carbamates, methyl carbonates, inverted bases (e.g., inverted T's), or chimeric versions of these backbones.

The term "substantially acid resistant" as used herein refers to nucleic acids that are resistant to acid degradation as compared to unmodified nucleic acids. Typically, the relative acid resistance of a nucleic acid will be measured by comparing the percent degradation of a resistant nucleic acid with the percent degradation of its unmodified counterpart (i.e., a corresponding nucleic acid with "normal" backbone, bases, and phosphodiester linkages). A nucleic acid that is acid resistant is preferably at least 1.5 times more resistant to acid degradation, at least 2 times more resistant, even more preferably at least 5 times more resistant, and most preferably at least 10 times more resistant than their unmodified counterpart.

The terms "PDE3A, PDE3B, PDE4A, PDE4B, PDE4C, PDE4D, PDE7A, PDE7B oligonucleotide" as used herein each refer to an oligonucleotide that is targeted, respectively, to sequences that affect PDE3A, PDE3B, PDE4A, PDE4B, PDE4C, PDE4D, PDE7A, PDE7B expression or activity. These include, but are not limited to, PDE3A, PDE3B, PDE4A, PDE4B, PDE4C, PDE4D, PDE7A, PDE7B DNA coding sequences, PDE3A, PDE3B, PDE4A, PDE4B, PDE4C, PDE4D, PDE7A, PDE7B DNA promoter sequences, PDE3A, PDE3B, PDE4A, PDE4B, PDE4C, PDE4D, PDE7A, PDE7B DNA enhancer sequences, mRNA encoding PDE3A, PDE3B, PDE4A, PDE4B, PDE4C, PDE4D, PDE7A, PDE7B, and the like.

As discussed above, one embodiment of the present invention provides antisense oligonucleotides targeted to sequences that affect PDE3A, PDE3B, PDE4A, PDE4B, PDE4D, PDE7A, expression or activity. In one embodiment the antisense oligonucleotides may have one of the sequences identified in Tables 1a-d or Tables 2a-g. In another embodiment, the antisense oligonucleotide may comprise fragments or variants of these sequences, as will be understood by a person skilled in the art, that may alter the oligonucleotide make-up and/or length, but which maintains or increases the activity of the oligonucleotide to downregulate gene expression. In another embodiment the present invention provides for combinations of at least two antisense oligonucleotides having the sequences identified in Tables 1a-d or Tables 2a-g.

Figure 5:
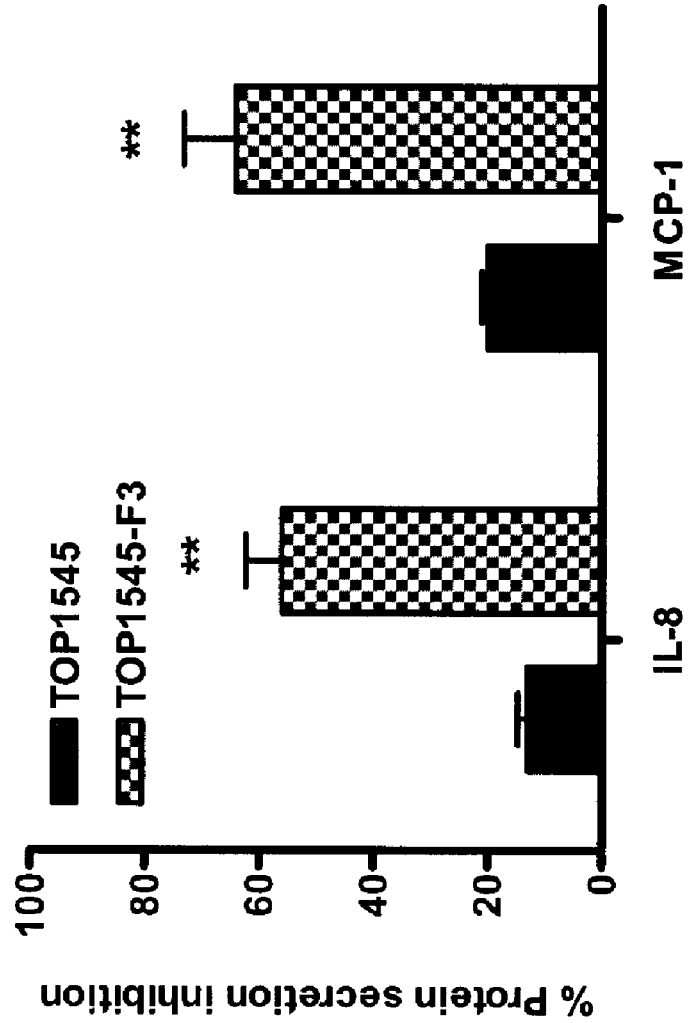
FIG. 5 shows the effect of 2'F-ANA-containing AON on biological effects of lung epithelial cells. A549 cells transfected with PDE4B/4D-dual specific AON composed of PS-DNA (TOP 1545, SEQ ID NO:14) or modified with FANA (PS-FANA, TOP 1545-F3, SEQ ID NO:85) overnight and were then stimulated with IL-1β (10 ng/mL) for 4 h. Supernatants were analyzed for IL-8 and MCP-1 secretion by ELISA (BD Biosciences) with levels normalized to cell viability determined by the AlamarBlue™ assay. Data expressed as mena % inhibition relative to expression level in cells treated with corresponding sense control sequence (**p<0.01, n=3).

The comparison of effectiveness of a single oligonucleotide is illustrated in, but not limited to, FIG. 1a, FIG. 1b and FIG. 5. For example in FIG. 1a TOP 1512 (Seq ID No 91) is directed against human PDE4A and PDE4B inhibits both of these targets in vitro. Similarly FIG. 1b shows TOP 1545 (Seq ID No 14) and TOP 1556 (Seq ID No 24) which recognize sequences shared by PDE4B and PDE4D, demonstrate inhibition of both target sequences. TOP 1507 (Seq ID No 10) and TOP 1508 (Seq ID No 11) which recognize sequences shared by PDE4A and PDE4D function to inhibit both target genes.

Figure 6:
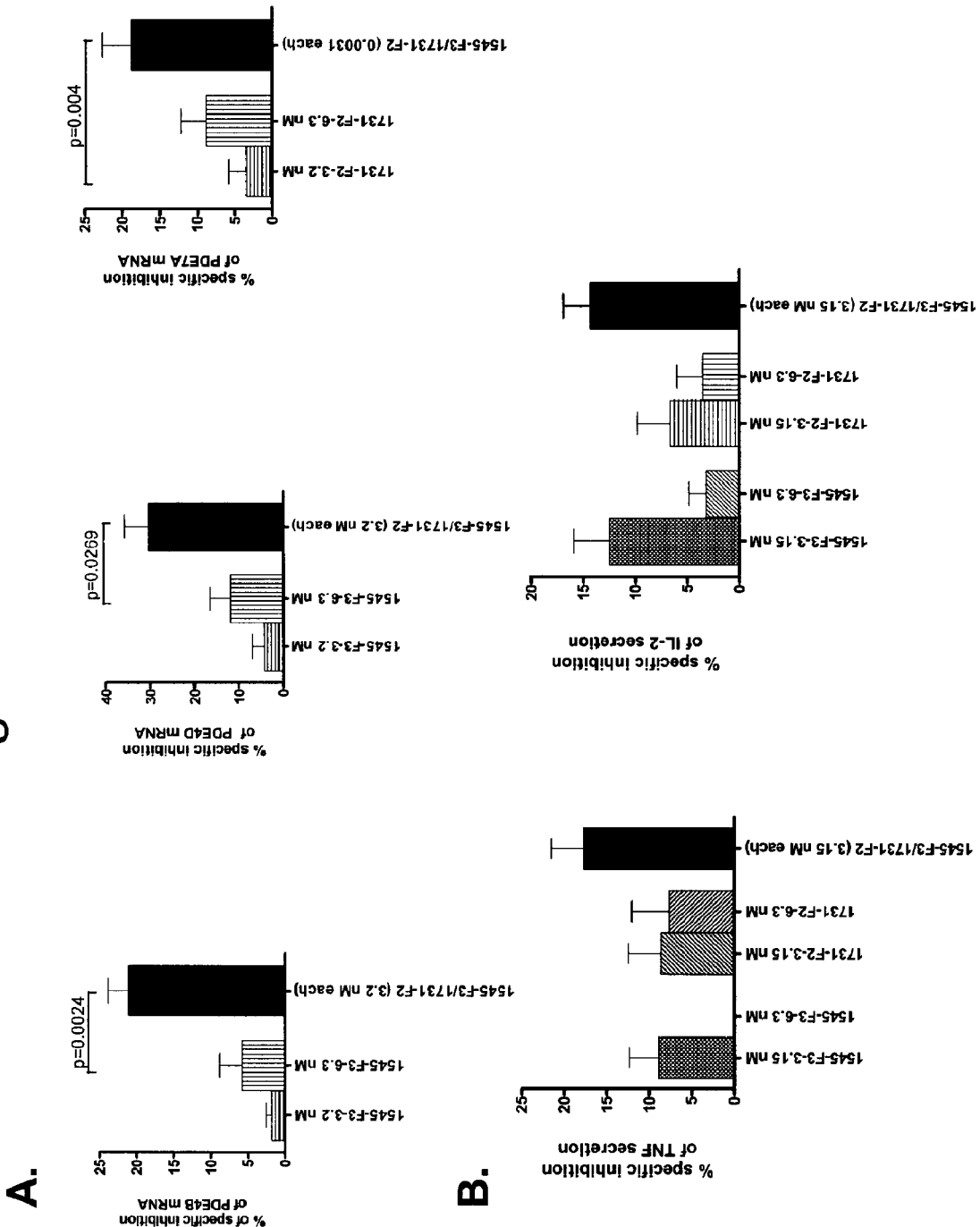
FIG. 6 shows the effect of 2'-F-ANA-containing AON in immune cells. (A) Human PBMCs transfected with FANA modified dual specific PDE4B/4D AON (TOP 1545) or FANA modified PDE7A specific AON (TOP 1731) or both for 20 h and were then stimulated with PHA (10 ug/mL) for 6 hrs. mRNA expression of target genes were assessed using Quantigene® assay (Panomics) with all PDE gene expression levels normalized to β2M gene expression. Data expressed as % specific inhibition of mRNA expression for PDE4B (n=8), PDE4D (n=6) and PDE7A (n=8) relative to levels in cells transfected with sense AON. P values determined for unpaired t-test comparing indicated columns. (B) Cell supernatants were harvested and levels of cytokines TNF-α and IL-2 secreted by PBMCs in response to PHA were assessed using ELISA (Medicorp). Decrease of cytokine was compared to levels in PHA stimulated cells in the absence of AON delivery. Data expressed as the % inhibition of AON relative to the levels of inhibition observed with same dose of mismatch or sense control oligonucleotide. Data expressed as mean % change±SE of between 8 donors.
Figure 7:
FIG. 7 shows the inhibition of thymidylate synthase (TYMS) gene expression in 293 cells transfected with PDE4B/4D specific AON (TOP-1545-F3) or TYMS specific AON (TOP-1549) using Lipofectamine™ 2000 (Invitrogen, ratio 1 ug oligonucleotide:1 uL Lipofectamine™ 2000) and 200 ng, 400 ng and 800 ng of either TOP-1545-F3 or TOP-1549 AON. Real-time PCR was used to quantify TYMS expression which was normalized to the expression of a control gene (Ppib). Data expressed as mean % inhibition relative to expression level of cells transfected with relevant sense or mismatch AON.
Figure 12:
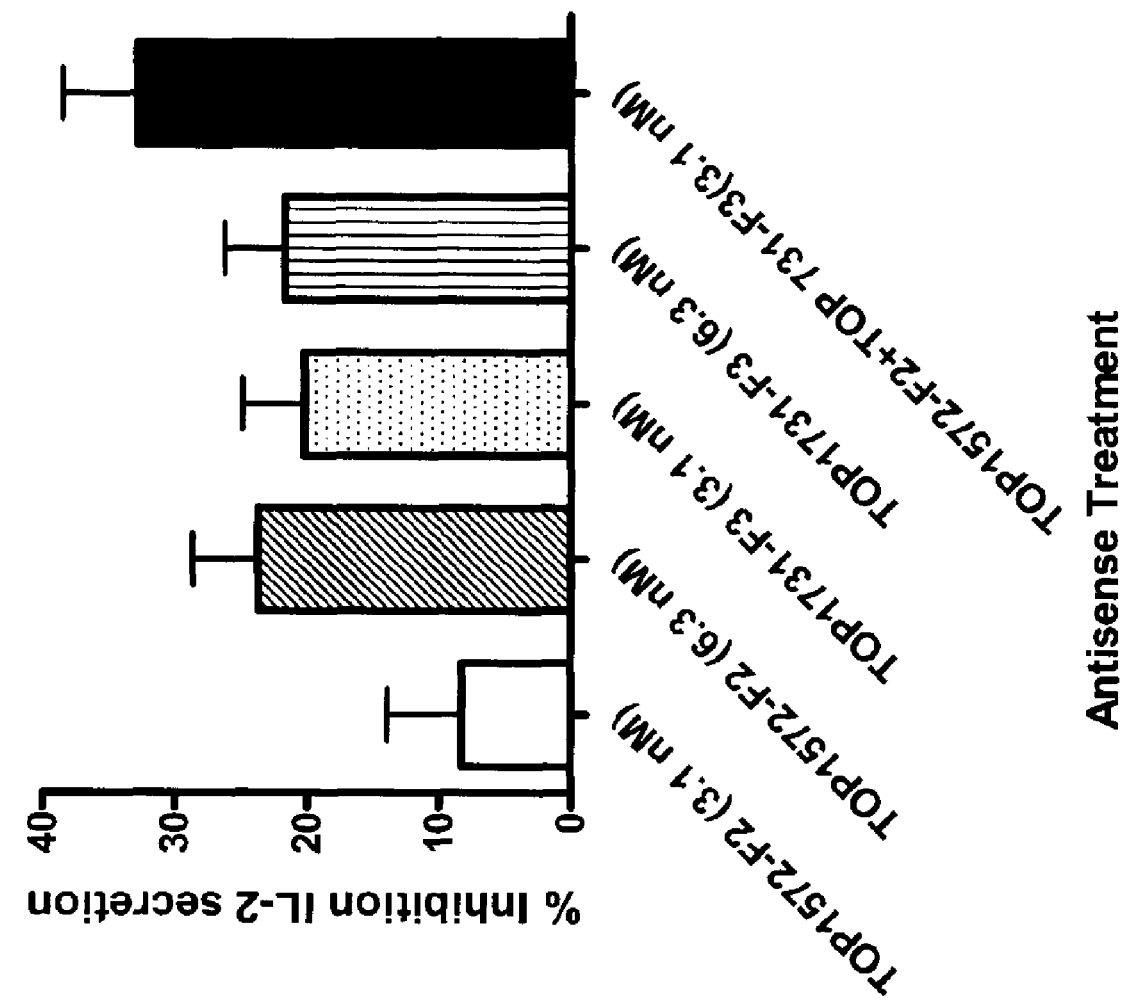
FIG. 12 shows the enhanced efficacy when F'ANA modified TOP 1572 and TOP 1731 are combined in reducing the cytokine secretion by PHA-stimulated PBMCs. Human PBMCs were transfected overnight with either TOP 1572-F2 (3.1 and 6.3 nM), TOP1731-F3 (3.1 and 6.3 nM) or both AON (3.1 nM each, total 6.3 nM). The following day PBMCs were stimulated with PHA (10 ug/ml) for 6 h and then levels of cytokine IL-2 in cell supernatants were quantified by ELISA. % inhibition of IL-2 secretion was determined compared to levels produced by untransfected cells following PHA stimulation. Values represent mean±S.E.

The comparison of effectiveness of combinations of at least 2 oligonucleotide compounds is illustrated in, but not limited to, FIGS. 6a and 12. For example in FIG. 6 the combination of TOP 1545-F3 (Seq ID No. 85) and TOP-1731-F2 (Seq. ID No. 53) show a greater effect at decreasing expression of both PDE4B, PDE4D and PDE7A than either of the oligonucleotides had on their respective targets when used alone. In FIG. 6b the combination of TOP-1545-F3 (seq. ID No. 85) and TOP-1731-F2 (Seq. ID No. 53) show a greater effect at decreasing IL-2-release in human PBMC than either of the oligonucleotides had on IL-2 when used alone at a the same total dose (6.3 nM). Referring to FIG. 12, the combination of TOP 1572-F2 (Seq ID No. 122) and TOP 17314-F3 (Seq. ID No. 54) show a greater effect of inhibiting IL-2 secretion than when used alone.

Many combinations of antisense oligonucleotide compounds may be used in accordance with the present invention, the combinations leading to multiple gene knock down as described above. Examples of combinations of antisense oligonucleotides may include, but are not limited to, at least one oligonucleotide compound directed against PDE3 with at least one oligonucleotide compound directed against PDE7. An alternative example of a combination may include at least one oligonucleotide directed against PDE4 and at least one oligonucleotide directed against PDE7. An alternative example of a combination may include at least one oligonucleotide directed against PDE3, at least one oligonucleotide directed against PDE4 and at least one oligonucleotide directed against PDE7. Such antisense oligonucleotide compounds may be chosen from, but are not limited to, the oligonucleotides provided in Tables 1a-d and Tables 2a-2g.

The terms "treatment", "treating", "therapy" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or amelioration of an adverse effect attributable to the disease. "Treatment" as used herein covers any treatment of a disease in a subject as previously defined, particularly a human, and includes:

(a) preventing a disease from occurring in a subject which may be predisposed to the disease but has not yet been diagnosed as having it;

(b) inhibiting a disease, i.e., arresting its development; or (c) relieving a disease, i.e., causing regression of the disease.

The term "pharmaceutically acceptable" as it is used herein with respect to carriers, surfactants and compositions refers to substances which are acceptable for use in the treatment of a subject patient that are not toxic or otherwise unacceptable for administration by any of the routes herein described.

The invention is generally directed toward the treatment of subjects by the administration of therapeutically effective amounts of antisense oligonucleotide compounds in accordance with the present invention, including siRNA, ribozymes, short nucleotide sequences as single or double stranded including RNA and/or DNA that may be complementary to a target nucleic acid, or may optionally be modified as described above, an RNA oligonucleotide having at least a portion of said RNA oligonucleotide capable of hybridizing with RNA to form an oligonucleotide-RNA duplex, or a chimeric oligonucleotide, that will downregulate or inhibit the expression of an endogenous gene in vivo.

By "therapeutically effective" amount is meant a nontoxic but sufficient amount of an antisense oligonucleotide compound to provide the desired therapeutic effect. In the present case, that dose of antisense oligonucleotide compound effective to relieve, ameliorate, or prevent symptoms of the condition or disease being treated, e.g. disease associated with reduced cellular cAMP, PDE-related disease, inflammatory disease such as inflammatory respiratory disease.

The pharmaceutical compositions provided herein comprise antisense oligonucleotide compounds described above and one or more pharmaceutically acceptable surfactants. Suitable surfactants or surfactant components for enhancing the uptake of the antisense oligonucleotides of the invention have been previously described in U.S. Application Publication No. 2003/0087845, the contents of which are incorporated with respect to surfactants The application states that suitable surfactants " . . . include synthetic and natural as well as full and truncated forms of surfactant protein A, surfactant protein B, surfactant protein C, surfactant protein D and surfactant protein E, di-saturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine; phosphatidic acid, ubiquinones, lysophosphatidylethanolamine, lysophosphatidylcholine, palmitoyl-lysophosphatidylcholine, dehydroepiandrosterone, dolichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, choline phosphate; as well as natural and artificial lamellar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric and polymeric, poly (vinyl amine) with dextran and/or alkanoyl side chains, Brij 35, Triton X-100 and synthetic surfactants ALEC, Exosurf, Survan and Atovaquone, among others. These surfactants may be used either as single or part of a multiple component surfactant in a formulation, or as covalently bound additions to the 5' and/or 3' ends of the antisense oligonucleotides (oligos)."

The antisense component of the present compositions, which includes the combination of at least two antisense oligonucleotide compounds, may be contained in a pharmaceutical formulation within a lipid particle or vesicle, such as a liposome or microcrystal. As described in U.S. Pat. No. 6,025,339, the lipid particles may be of any suitable structure, such as unilamellar or plurilamellar, so long as the antisense oligonucleotide is contained therein. Positively charged lipids such as N-[1-(2,3-dioleoyloxi)propyl]-N,N,N-trimethyl-ammoniumethylsulfate, or "DOTAP," are particularly preferred for such particles and vesicles. The preparation of such lipid particles is well known. See, e.g., U.S. Pat. Nos. 4,880,635 to Janoff et al.; 4,906,477 to Kurono et al.; 4,911,928 to Wallach; 4,917,951 to Wallach; 4,920,016 to Allen et al.; 4,921,757 to Wheatley et al.; etc.

The composition of the invention may be administered by any means that transports the antisense oligonucleotide compound to the desired site, such as the lung. The antisense compounds disclosed herein may be administered to the lungs of a patient by any suitable means, but are preferably administered by inhalation of an aerosol comprised of respirable particles that comprise the antisense compound.

The composition of the present invention may be administered into the respiratory system as a formulation including particles of respirable size, e.g. particles of a size sufficiently small to pass through the nose, mouth and larynx upon inhalation and through the bronchi and alveoli of the lungs. In general, respirable particles range from about 0.5 to 10 microns in size. Particles of non-respirable size that are included in the aerosol tend to deposit in the throat and be swallowed, and the quantity of non-respirable particles in the aerosol is preferably thus minimized. For nasal administration, a particle size in the range of 10-500 μM (micro-meter)) is preferred to ensure retention in the nasal cavity.

Liquid pharmaceutical compositions of active compound (the antisense oligonucleotide compound(s)) for producing an aerosol may be prepared by combining the antisense compound with a suitable vehicle, such as sterile pyrogen free water or phosphate buffered saline.

A solid particulate composition comprising the antisense compound may optionally contain a dispersant that serves to facilitate the formation of an aerosol as well as other therapeutic compounds. A suitable dispersant is lactose, which may be blended with the antisense compound in any suitable ratio, e.g., a 1 to 1 ratio by weight.

The antisense compositions may be administered in an anti-bronchoconstriction, anti-allergy(ies) and/or anti-inflammatory effective amount, which amount depends upon the degree of disease being treated, the condition of the subject patient, the particular formulation, the route of administration, the timing of administration to a subject, etc. In general, intracellular concentrations of the oligonucleotide of from 0.05 to 50 µM, or more particularly 0.2 to 5 µM, are desirable. For administration to a mammalian patient such as a human, a dosage of about 0.001, 0.01, 0.1, or 1 mg/Kg up to about 50, or 100 mg/Kg or more is typically employed. However, other doses are also contemplated. Depending on the solubility of the active compound in any particular formulation, the daily dose may be divided among one or several unit dose administrations.

The aerosols of liquid particles comprising the antisense compound may be produced by any suitable means, such as with a nebulizer. Nebulizers are commercially available devices that transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers comprise the active antisense oligonucleotide ingredient in a liquid carrier in an amount of up to 40% w/w preferably less than 20% w/w of the formulation. The carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, anti-oxidants, anti-bacterials, flavorings, volatile oils, buffering agents and emulsifiers and other formulation surfactants.

The aerosols of solid particles comprising the active oligonucleotide compound(s) and a pharmaceutically acceptable surfactant may likewise be produced with any solid particulate medicament aerosol generator. Aerosol generators for administering solid particulate medicaments to a subject produce particles that are respirable, as explained above, and generate a volume of aerosol containing a predetermined metered dose of a medicament at a rate suitable for human administration. The active oligonucleotide ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 .mu.l, to produce a fine particle spray containing the active ingredient. Suitable propellants include certain chlorofluorocarbon compounds, for example, dichlorodifluoromethane, trichlorofluoromethane, dichlorotetrafluoroethane or hydrofluoroalkanes and mixtures thereof. The formulation may additionally contain one or more co-solvents, for example, ethanol, emulsifiers and other formulation surfactants, such as oleic acid or sorbitan trioleate, anti-oxidants and suitable flavoring agents. The aerosol, whether formed from solid or liquid particles, may be produced by the aerosol generator at a rate of from about 1 to 150 liters per minute.

The formulations of the present invention may be oral, intrabuccal, intrapulmonary, rectal, intrauterine, intratumor, intracranial, nasal, intramuscular, subcutaneous, intravascular, intrathecal, inhalable, transdermal, intradermal, intracavitary, implantable, iontophoretic, ocular, vaginal, intraarticular, otical, intravenous, intramuscular, intraglandular, intraorgan, intralymphatic, implantable, slow release or enteric coating formulations. The carriers used in the formulations may be, for example, solid and/or liquid carriers.

Reference may be made to "Remington's Pharmaceutical Sciences", 17th Ed., Mack Publishing Company, Easton, Pa., 1985, for other carriers that would be suitable for combination with the present oligonucleotide compounds to render compositions/formulations suitable for administration to treat respiratory disease.

In a further aspect of the present invention, an article of manufacture is provided which includes packaging material contained within which is a pharmaceutically acceptable antisense oligonucleotide composition that is therapeutically effective to treat conditions associated with reduced cellular cAMP, or elevated levels of PDE, including inflammatory disease. In one embodiment, the composition comprises an antisense oligonucleotide compound that is effective to inhibit a PDE gene, said oligonucleotide compound being at least 50% complementary to the gene. In another aspect, the composition comprises at least 2 antisense oligonucleotide compounds, each antisense oligonucleotide compound being capable of downregulating a different PDE gene, each antisense oligonucleotide compound being present at a concentration at which the antisense oligonucleotide compound is practically ineffective on its own to downregulate the gene it is directed against, the combination of the antisense oligonucleotide compounds being effective to downregulate at least one of the genes that the antisense oligonucleotides are directed against.

In one embodiment, the packaging material of the article comprises a label which indicates that the composition can be used to treat inflammatory disease and may additionally include an indication that the disease is one of multiple sclerosis, contact dermatitis, allergic and non-allergic eye diseases, rheumatoid arthritis, septic shock, osteoporosis and cognitive disorders.

In another embodiment, the packaging material of the article comprises a label which indicates that the composition can be used to treat inflammatory respiratory disease, and may additionally include an indication that the disease is one of COPD, asthma, eosinophilic cough, bronchitis, acute and chronic rejection of lung allograft, sarcoidosis, pulmonary fibrosis, rhinitis or sinusitis.

For the purposes of the present invention, the packaging material may be any suitable material for packaging a nucleotide-containing composition in accordance with the present invention, including a bottle or other container (either plastic or glass), a carton, a tube, or other protective wrapping. As will be appreciated, the packaging may vary with the nature of the oligonucleotide composition, for example, a liquid formulation may be packaged differently than an aerosol formulation.

The present invention is illustrated in further detail by the following non-limiting examples.

EXAMPLES

Materials and Reagents

AIM-V media (Invitrogen, Cat#31035-025); Opti MEM I (Invitrogen, cat#31985-07, lot#1244206); FBS (Fetal Bovine Serum, Wisent, cat# 80150); Penicillin, Streptomycin (GIBCO, cat# 15140-122); HEPES (Wisent, cat# 26060CI) and L-glutamine (Gibco, cat# 25030-081); DMEM/F12 (Wisent, cat# 10090CV); Sodium Pyruvate (Wisent, cat#

25000-Ci); PBS Sterile (GIBCO, cat# 25030-081); Trypsin 0.25% and EDTA 0.01% (Wisent, cat# 25-052-Ci); HBSS (Hank's balanced salt solution, Wisent, Cat# 21-022CV); PHA (Phytohemaglutinin, Sigma, cat#L-9132, lot#: 015K88913); Ficoll paque (Amersham, Cat# 17-1440-03); Trizol (Invitrogen, cat#15596-018); Dnase I (Fermentas, cat#EN0521); Superscript First-Strand Synthesis System for RT-PCR kit (Invitrogen, cat#11904-018); dNTPs (Invitrogen, cat# 10297-018); oligo (dT)$_{12-18}$; (Invitrogen, cat#11904-018); Qiagen RNAeasy Mini Kit (Qiagen, Cat#74106); Qia-Vac 24 Manifold (Qiagen, Cat#19403); Disposable Vacconnectors (Qiagen, Cat#19407); RiboGreen Quantification Reagent (Invitrogen-Molecular probes, Cat # R-11490); Light-Cycler Instrument version 1.5 (Roche, Cat# 3531414); LC Capillaries for 20 ml reactions (Roche, cat# 1909339); LC FastStart DNA Master SYBR Green 1 PLUS (100 ml) (Roche, Cat# 03752186001); K3EDTA tubes (Greiner Bio-one, cat#: 455036B110306); Cyclic AMP EIA Kit (Cayman, cat.# 581001) Human TNF-α ELISA kit, (BioSource Cat#CHC-1754, lot# 041703); Human IL-8/CXCL8 ELISA kit (Biosource, cat# CHC1303); Human MCP-1/CCL2 ELISA kit (Biosource, cat# KHC1012); cAMP EIA kit (Cayman, cat# 581001); Human GMCSF ELISA (Medicorp, cat#CHC0904); Human IL-2 ELISA (BD Biosciences, cat#555190); ELISA plate reader (filter 450 nm, reference filter 650 nm, Biorad, model 680); Escort IV transfection agent (Sigma-Aldrich, cat#3287, lot#094K0565); hIL-1β (Peprotech, cat. #11195D195); Forskolin (Sigma-Aldrich cat#F3917); Rolipram (Sigma-Aldrich Cat # R6520, lot # 022K4604); Alamar Blue, (Biosource cat#DAL1100); 12-well plate high binding (Costar, cat #665 102); TMB chromogen reagent for ELISA (MediCorp, cat # SB01); Lipofectamine™2000 transfection reagent (Invitrogen, cat#11668-019); Quantigene® Screen Kit (Panomics, cat# QG-000-050); 20×SSC (3M NaCl, 0.3 M sodium citrate dihydrate, pH 7.0); Lithium dodecyl sulfate 10% w/v (Sigma, cat# L9781); Incubator set at 53° C., 0% $CO_2$; MW96 Plate Washer (Beckman Coulter); Thermo Luminoskan (Lab-System); EMEM (HyClone, cat#SH30024.01); non-essential amino acids (HyClone, cat#30238.01); BEBM (Clonetics, cat#CC-3171); BEBM kit (Clonetics, cat#3170); Human TNF-α (Peprotech, cat.#300-01A); Human IFNγ (Peprotech, cat#315-05).

Cell Culture 293 cells (human transformed embryonic kidney cell line; ATCC cat#: CRL-1573) were cultivated in DMEM containing 2 mM L-glutamine, 0.1 mM non-essential amino acids, 1.5 g/l sodium bicarbonate, 1 mM sodium pyruvate, 10% FBS, penicillin 100 U/mL and streptomycin 100 microg/mL. A549 (Human lung carcinoma cell lines; ATCC) were cultivated in Ham's F12 media containing 2 mM L-glutamine; 1.5 g/L sodium bicarbonate; 10% FBS, Penicillin 100 U/mL, Streptomycin 100 microg/mL. Human peripheral blood mononuclear cells (PBMC) (peripheral blood mononuclear cells) were obtained from healthy volunteers. PBMC were isolated by Ficoll-Hypaque density gradient centrifugation of EDTA K3 blood from normal donors. PBMC were plated at $2 \times 10^6$ cells/mL/well in 12 well plates in AIM-V culture media supplemented with Penicillin 100 U/mL, Streptomycin 100 microg/mL. CYNOM-K1 cells were cultivated in EMEM containing 2 mM L-glutamine, 1% non-essential amino acids, 10% FBS, penicillin 100 U/mL and streptomycin 100 microg/mL. NHBE cells were cultivated in BEBM (500 mL supplemented with BPE, 2 ml; Hydrocortisone, 0.5 ml; hEGF, 0.5 ml; Epinephrine, 0.5 ml; Transferrin, 0.5 ml; Insulin, 0.5 ml; Retinoic Acid, 0.5 ml; Triiodothyronine, 0.05 ml).

Cell Viability

Cell viability was systematically assayed using Alamar Blue test following the manufacturer's guidelines.

Preparation of Antisense

Phosphorothioate-DNA antisenses (Sigma Genosys) and phosphothiorate-FANA antisenses (Topigen, Montreal or UCDN, Calgary) were resuspended in sterile water and diluted in Opti-MEM for transfection. References to DNA (non-FANA) oligonucleotides in the examples are phosphorothioate-DNA oligonucleotides.

Antisense Treatment of Cells:

A549 Cell Line:

Cells were trypsinized and re-suspended in HAM-F12 medium ($0.5 \times 10^5$ cells/well in 48 well plates) supplemented with 10% serum in antibiotic starvation conditions then incubated overnight at 37° C. The next day, adherent cells were transfected with antisense/Lipofectamine complexes (ratio of 1 ug oligonucleotide:1 uL Lipofectamine) at concentrations indicated in figure descriptions, and incubated at 37° C. for a determined period of time.

293 Cell Line:

Cells were trypsinized and resuspended ($1 \times 10^5$ cells/well in 48 well-plates) in DMEM medium supplemented with 10% serum in antibiotic deprivation conditions then incubated overnight at 37° C. The next day, adherent cells were transfected with antisense/Lipofectamine complexes (ratio of 1 ug oligonucleotide:1 uL Lipofectamine) at concentrations indicated in figure legends and incubated at 37° C. for a determined period of time.

PBMC

The day of isolation PBMCs were plated ($2.0 \times 10^6$/ml in 12 well plates) in AIM-V media. Antisenses were complexed with Escort IV reagent (Sigma) (ratio of 1 ug oligonucleotide: 0.5 uL Escort IV) and were added at concentrations indicated in figures. Cells were cultured for 18-24 hours at 37° C., 5% $CO_2$, humidity.

CYNOM-K1 Cell Line:

Cells were trypsinized and resuspended in EMEM medium supplemented with 10% serum in antibiotic starvation conditions ($0.5 \times 10^5$ cells/well in 200 uL in 48 well plates) then incubated overnight at 37° C. The next day, adherent cells were transfected with antisense/Lipofectamine 2000 complexes (ratio of 1 ug oligonucleotide:2 uL Lipofectamine) at concentrations indicated in figure descriptions, and incubated at 37° for a determined period of time.

NHBE Cells:

Cells were trypsinized and resuspended in BEBM complete medium in antibiotic starvation conditions ($1 \times 10^5$ cells/well in 200 uL in 48 well plates) then incubated overnight at 37° C. The next day, adherent cells were transfected with antisense/Lipofectamine 2000 complexes (ratio of 1 ug oligonucleotide:1 uL Lipofectamine) at concentrations indicated in figure descriptions, and incubated at 37° for a determined period of time.

RNA Extraction

RNA was extracted from cell pellets according to RNAeasy mini kit protocol using the QiaVac 24 manifold from Qiagen and treated with DNase-I according to Fermentas procedure. RNA was quantified using the RiboGreen reagent according to the manufacturer protocol (Invitrogen-Molecular probes).

Reverse Transcription (RT)

Preparation of first-strand cDNA was performed using the Superscript First-Strand Synthesis System for RT-PCR kit, in a total reaction volume of 20 μL. 1 μg of RNA was first denatured at 65° C. for 5 minutes, with 0.5 mM of each dNTPs, 0.5 μg of oligo (dT)$_{12-18}$ and chilled on ice for at least 1 min. The mixture was incubated at 42° C. for 2 minutes and a second pre-mix containing 1× First-Strand Buffer, 10 mM DTT, and 40 units of SuperScript II RT was added. Reactions were incubated at 42° C. for 10 minutes, at 50° C. for 1 hour and inactivated by heating at 70° C. for 15 minutes.

Real-Time PCR

PCR reaction mixtures were performed with 3 µL of cDNA reaction in a total volume of 20 µL in presence of 0.4 mM of each PCR primer and 4 µL of LC FastStart DNA Master SYBR Green 1 PLUS. Step 1 (Denaturation): 95° C., 10 min (slope 20° C./sec); Step 2 (Cycles×40): 95° C., (slope 20° C./sec); 57° C. or 59° C., 5 sec. (slope 20° C./sec) 72° C., 10 sec. (slope 20° C./sec); Step 3 (Melting curve):95° C., (slope 20° C./sec); 70° C., 30 sec. (slope 20° C./sec); 95° C., 0 sec. (slope 0.1° C./sec); Step 4 (Cool): 40° C., 30 sec (slope 20° C./sec) PCR primer sequences used for each gene are described in Table 3. Quantification of PCR products was performed using the RelQuant program (Roche).

Quantigene Assay

Cells were harvested and lysed for 30 minutes at 53° C. in 1× lysis mixture from the Quantigene® kit. Cell lysates were hybridized overnight at 53° C. in Quantigene® capture plates in the presence of specific probe sets and mRNA expression was linearly quantified by luminescence signal using Luminoskan.

Cellular Assays: (ELISAs, EIA)

A549 Cells

At the end of the transfection period, A549 cells were incubated for 4 h with IL-1β (10 ng/ml). Supernatants were harvested and analysed using ELISA for human IL-8, human MCP-1 and human GM-CSF.

PBMCs

After overnight transfection, PHA (10 µg/mL) was added to cells for 6 hrs. Some cells received treatment with Rolipram (10 µg/mL) or Forskolin (2 µM) for 30 minutes prior to cell harvesting. Supernatant were collected and frozen until time to perform IL-2 and TNF-α ELISA following manufacturer's guidelines. Determination of intracellular cAMP levels was performed on cell pellets that were lysed and lysates was frozen until time to perform cAMP EIA according to manufacturer's protocols.

NHBE Cells:

NHBE cells were stimulated for 4 h with cytomix (500 U/mL TNF-α+10 ng/mL IL1-β+10 ng/mL IFNγ) at the end of the transfection period. MCP-1 protein secretion was measured in supernatant by ELISA, with normalization to the cell viability as measured by AlamarBlue assay.

Example 1

Composition of Antisense and Potency In Vitro

The sequence and composition of the antisense oligonucleotides prepared in this study are shown in Tables 1a, 1b, 1c and 1d. All oligonucleotides were purified by anion exchange HPLC or gel electrophoresis and desalted via a size-exclusion chromatography using Sephadex G-25 beads. The potency of some selected sequences listed in Tables 1a-1d are demonstrated in FIGS. 1a and 1b which show the reduction in gene expression of specific PDE isoforms in cells following transfection with indicated AON. FIG. 1A shows cell lines, either A549 for PDE3A, PDE3B and PDE7A or 293 cells for PDE4A, PDE4B and PDE4D had decreased levels of target isoforms following overnight transfection with specific AON. PDE mRNA expression level was quantified using the Quantigene® assay (Panomics) for PDE3A/B, PDE4D and PDE7A and real-time PCR was used to quantify expression of PDE4A/4B. PDE isoform levels were normalized to the expression of a control gene (β2M, Ppib or HPRT) and these levels were compared to expression levels of untreated cells.

Although the majority of antisense oligonucleotides designed were specific for PDE isoforms, some AON, in particular for PDE4 isoforms, demonstrated dual specificity for target knockdown of more than one PDE4 isoform. Sequences listed in Table 1c describe AON which have demonstrated more than one target gene knockdown with the single AON. FIG. 1b demonstrates the efficacy of these AON that were designed for dual target specificity. AON TOP 1545 (Seq ID No 14) and TOP 1556 (Seq ID No 24) each recognize gene sequences shared between PDE4B isoform and PDE4D isoform (Table 1c), and demonstrate target gene knockdown for PDE4B and PDE4D while AON. TOP 1507 (Seq ID No 10) and 1508 (Seq ID No 11) are effective in decreasing mRNA levels of PDE4A and PDE4D in transfected cells and both AON recognize sequences shared between PDE4A and PDE4D isoforms (Table 1c). Data is expressed as % specific inhibition determined by comparing the levels of inhibition obtained with the control mismatch or sense AON sequences with the % inhibition obtained with their respective PDE-specific AON sequences.

Example 2

Effect of AON Delivery on Biological Functions of Cells

Figure 2:
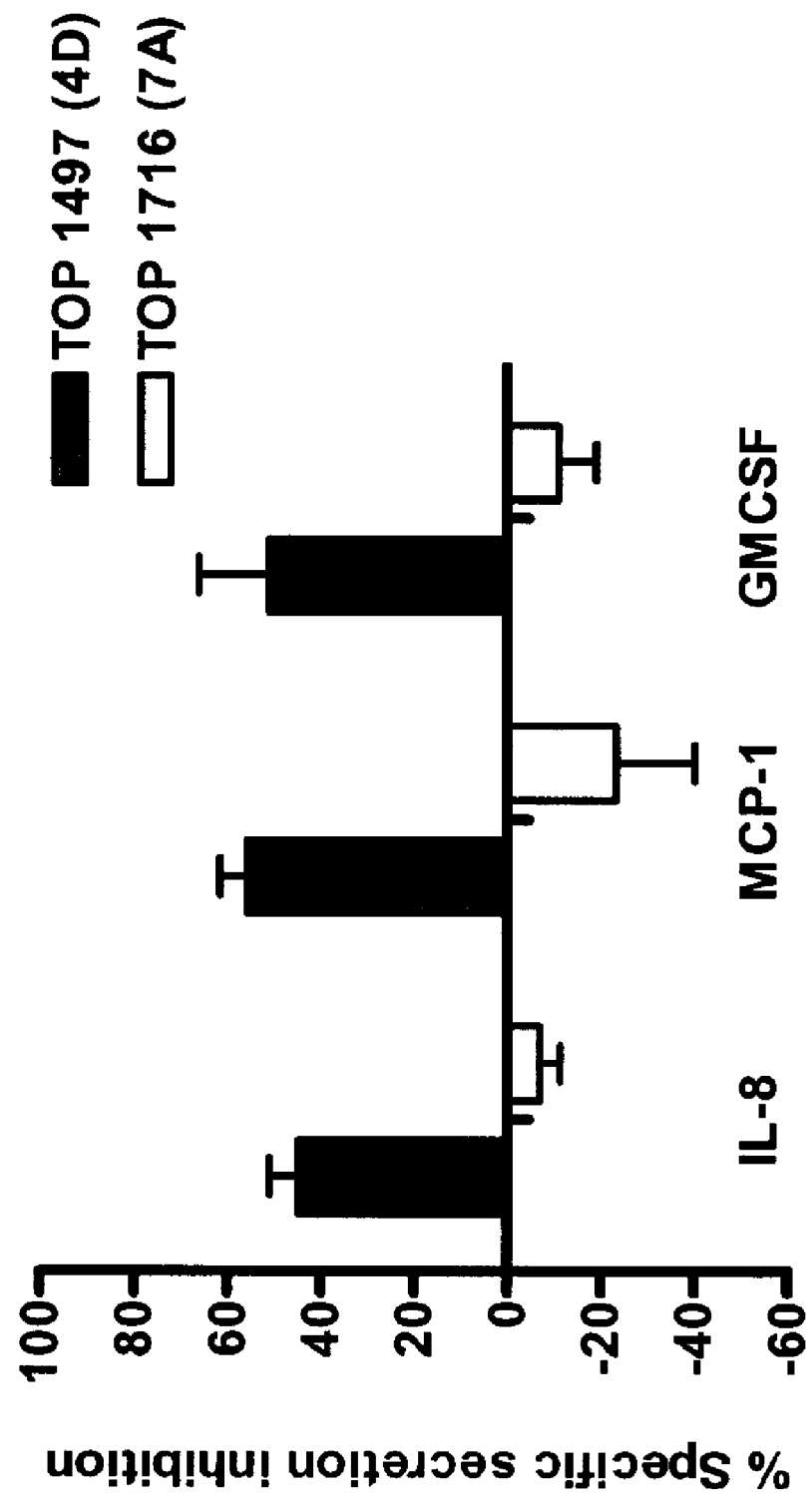
FIG. 2 shows the biological effect on AON on lung epithelial cells. A549 cells transfected overnight with AON as described above were stimulated with IL-1β (10 ng/mL) for 4 h to induce secretion of chemokines (IL-8, MCP-1) and cytokine (GM-SCF). Cell supernatants were harvested and levels of chemokines/cytokines determined using ELISA. Data expressed mean % inhibition of specific secretion which compares levels of secretion between PDE-AON targeted cells with mismatch/sense AON targeted cells.

This example relates to efficacy of AON on the biological function of different cell types, specifically the secretion of cytokines and chemokines. Cytokines and chemokines are important mediators of cell activation and recruitment. Lung epithelial cells can play a role in the pathophysiology of inflammatory respiratory diseases through the secretion of chemokines that lead to the recruitment of immune cells, such as neutrophils and monocytes/macrophages. Interleukin-8 (IL-8/CXCL8) and monocyte chemoattractant protein-1 (MCP-1/CCL2) levels are increased in COPD patients (Szilasi M et al. Pathology Oncology Research. 2006 12:52-60). The levels of IL-8 and MCP-1 may be involved in neutrophil and macrophage recruitment respectively. Both IL-8 and MCP-1 are secreted by the lung epithelial cell line, A549 in response to stimulation with IL-1β. Stimulated A549 cells also secrete granulocyte-macrophage cell stimulating factor (GM-CSF), a cytokine known to activate neutrophils and macrophages for enhanced function. FIG. 2 demonstrates the efficacy of AON TOP 1497 (Seq ID No 90) which is specific for PDE4D isoform, to limit the secretion of chemokines IL-8/CXCL-8 and MCP-1/CCL2 and cytokine GM-CSF in A549 cells following overnight transfection of AON then stimulated with IL-1β for 4 h. The use of this assay allows the verification of PDE isoforms involved in the release of inflammatory mediators by lung epithelial cells. In FIG. 2, the contribution of PDE4D, through its inhibition by TOP 1497 (Seq ID No 90), in the A549 cells is clearly demonstrated whereas there is no contribution of PDE7A in these cells for the release of chemokines and cytokines although transfection with AON TOP 1716 (Seq ID No 92) was successful in reducing mRNA levels of this gene. FIG. 2 demonstrates functional changes, specifically the reduction of inflammatory potential through the decrease in secretion of inflammatory mediators that can occur in lung epithelial cells following transfection with AON.

Figure 3:
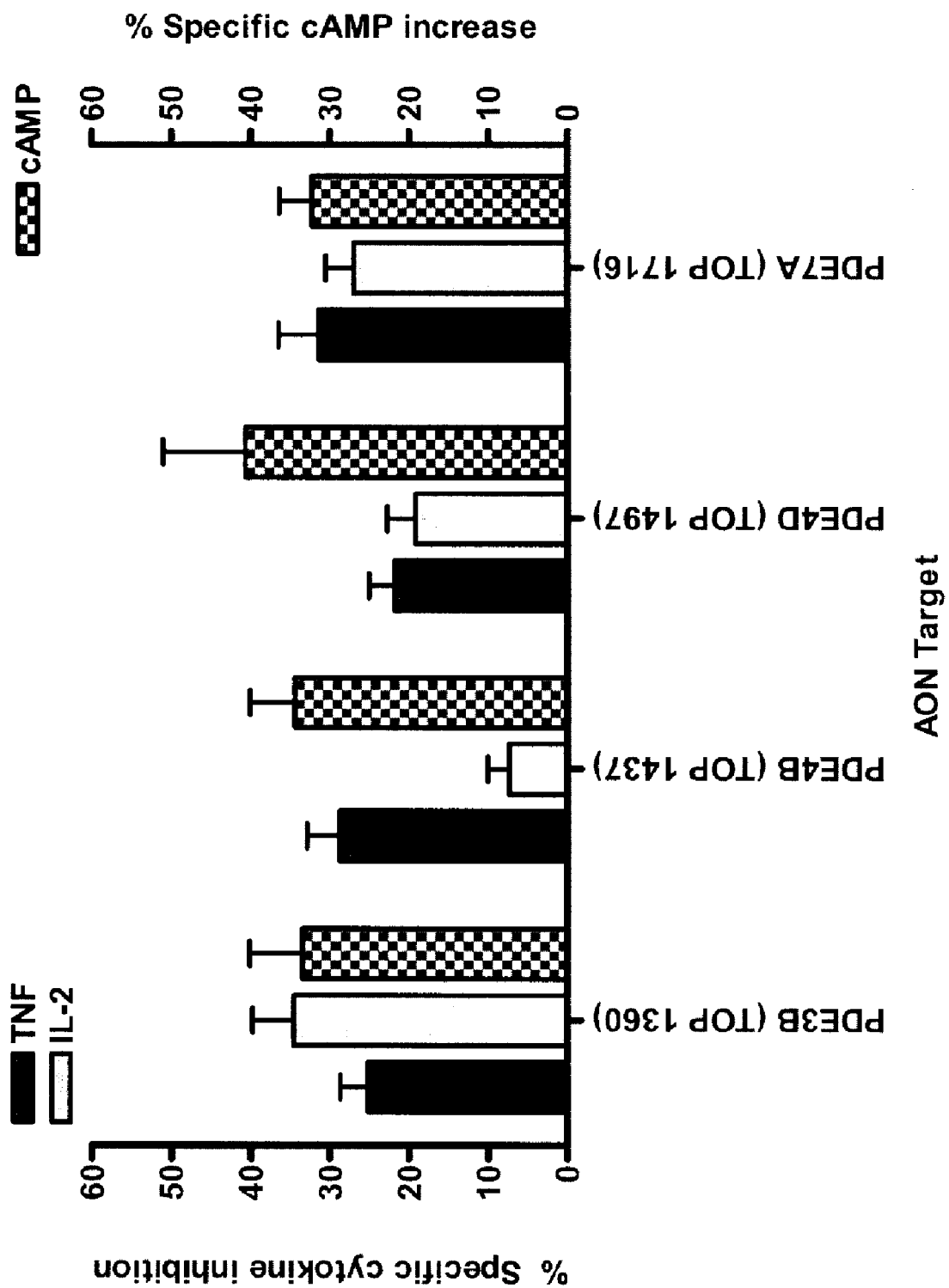
FIG. 3 shows the biological effect of AON on immune cells. Human PBMCs transfected with AON for 20 h using lipidic reagent Escort IV (1 ug AON:0.5 uL Lipid) were then stimulated with PHA (10 ug/mL) for 6 hrs. Cell supernatants were harvested and levels of cytokines TNF-α and IL-2 secreted by PBMCs in response to PHA were assessed using ELISA (BD Biosciences). Decrease of cytokine was compared to levels in PHA stimulated cells in the absence of AON delivery. Data expressed as the % inhibition of AON relative to the levels of specific cytokine inhibition observed with mismatch or sense control sequence AON (left hand axis). Cell lysates were harvested for cAMP determination using cAMP EIA (Cayman Chemical) as a measure of PDE activity. Increase in cAMP compared levels in PHA stimulated cells in the absence of AON delivery. Data expressed as % specific increase of cAMP relative to levels achieved with mismatch or sense control sequence AON (right hand axis). Data expressed as mean % change± SE of between 9-15 donors.

FIG. 3 demonstrates the efficacy of AON to limit biologic function of different cell types, specifically human peripheral blood mononuclear cells (PBMCs) PBMCs refer to a mixed population of immune cells that secrete cytokines, specifically TNFα which is known to activate macrophages and IL-2 which is known to activate and stimulate T cells and NK cells. Human PBMCs transfected overnight with AON targeting PDE isoforms then stimulated the following day with phytohemagglutin (PHA) secreted less TNFα and IL-2 than PBMCs transfected with mismatched or sense AON sequences (FIG. 3). Transfection of PBMC with the described AON led to a decrease in the inflammatory potential of these cell types. In COPD release of proinflammatory mediators and chemoattractants by inflammatory cells and activated epithelial cells contribute to further increased levels of inflammation (Szilasi M et al. Pathology Oncology Research. 2006 12:52-60).

It is expected that inhibition of PDE gene expression, would lead to reduced PDE activity, that would in turn result in a build up of cAMP inside cells. FIG. 3 demonstrates that transfection with AON targeting specific PDE isoforms led to increased intracellular cAMP levels in the PBMCs (right hand axis). Data represent the changes in levels of either cytokine or cAMP in PBMCs following transfection with PDE-specific AON compared to levels following transfection with mismatch or sense sequences.

Cytokines play a critical role in the orchestration of chronic inflammation in all diseases, including asthma and COPD. TNF-α is one of the most important pro-inflammatory cytokines that is expressed in several inflammatory diseases. TNFα levels are markedly increased in induced sputum of patients with COPD (Keatings et al., Am. J. Respir. Crit. Care Med. 1996; 153; 530-534.). Furthermore, there is evidence that COPD patients with weight loss show increased release of TNFα from circulating cells and that TNFα may induce apoptosis of skeletal muscle cells, resulting in the characteristic muscle wasting and cachexia seen in some patients with severe COPD (De Godoy et al., Am. J. Respir. Crit. Care Med. 1996, 153, 633-637.). TNF-α induces the gene expression of many pro-inflammatory cytokines including itself and IL-8. Cytokines, specifically TNFα are amongst the mediators that have been shown to be increased and/or play a role in the pathophysiology of inflammatory respiratory diseases and involved in tissue destruction.

PDE4 inhibitors caused a decrease in the release of cytokines and chemokines from inflammatory cells via an increase in intracellular cyclic AMP (Torphy, Am. J. Respir. Crit. Care Med. 1998, 157, 351-370). In contrast to corticosteroids, PDE4 inhibitors have a potent inhibitory effect on neutrophils (Au et al., Br. J. Pharmacol. 1998, 123, 1260-1266.) indicating that they may be useful anti-inflammatory treatments for COPD. There is preliminary evidence that a PDE4 inhibitor Cilomilast improves lung function and symptoms in patients with COPD and this may be due to cytokine inhibition (Compton et al., Lancet. 2001, 358, 265-270).

As TNFα, is considered as a common denominator in inflammatory and chronic respiratory diseases, this invention provides a broad therapeutic application for treating several inflammatory diseases.

Example 3

AON Modified with 2'F-ANA Chemistry Demonstrate Increased Efficacy and Prolonged Action for Target Gene Knockdown This example relates to the enhanced efficacy of PDE-specific AON when FANA modifications are made into the chemistry of the AON. Tables 2a-2g describe the compositions of AON modified with F-ANA residues. In FIG. 4, A549 cells were transfected for 24 h with PDE4D-specific AON TOP 1497 (Seq. ID No. 90) either in phosphothiorate composition (PS-DNA) or containing FANA base modifications (PS-FANA; TOP 1497-F1 (Seq ID No. 72), TOP-1497-F5 (Seq ID No.76), TOP 1497-F6 (Seq ID No. 77)) as indicated in the legend provided in FIG. 4. PDE4D mRNA knockdown was determined using the Quantigen® assay (Panomics) with PDE levels normalized to β2M gene expression. Modification of TOP 1497 sequence with FANA monomers, (TOP 1497-F1 (Seq ID No. 72)) enhanced the efficacy of the AON to inhibit target gene expression at doses between 100-400 ng, clearly showing an advantage of this modification for AON activity (FIG. 4a). 2'-F-ANA modifications are expected to enhance the stability of the AON, rendering it more resistant to nucleosidase digestion, which would prolong its activity. In FIG. 4b, comparison of different formulations of PDE4D-specific AON TOP 1497 at a single dose over time clearly shows the 2'-F-ANA containing AON have sustained inhibitory activity up to 48 hp compared to PS-DNA AON. At 48 h after transfection, no inhibition is observed with the PS-DNA formulation of AON, however, even by modifying only 5 of the 19 bases AON TOP 1497-F6 (Seq ID No 77) with 2'-F-ANA, was sufficient to sustain an inhibitory effect for this time point. The sustained inhibition was increased by incorporating more 2'-F-ANA residues into the original sequence as shown following transfection with TOP 1497-F5 (Seq ID No 76) and TOP 1497-F1 (Seq ID No 72). The greater amount of 2'-F-ANA composition in AON yielded the most prolonged effect, although by overnight transfection (24 h), PS-FANA containing 7 residues yielded a similar level of inhibition as PS-FANA containing 11 residues.

Example 4

AON Modified with 2' F-ANA Chemistry Retains Biological Function in Cells

This example refers to the tolerance of 2'-F-ANA chemistry modification of PDE-specific AON in reducing the inflammatory responses of cells. In FIG. 2, the efficacy of PDE-specific AON to reduce chemokine secretion by lung epithelial cells was demonstrated. In FIG. 5 the effect of 2'-F-ANA containing AON on biological function of A549 was studied. A549 cells transfected with PDE4B/4D dual specific AON TOP 1545 (Seq ID No 14) as PS-DNA or with 2'-F-ANA modified TOP 1545-F3 (Seq ID No 85) demonstrate higher levels of inhibition of chemokine secretion when 2'-F-ANA containing AON were transfected in the A549 cells compared to the unmodified AON.

This retention of biological efficacy of 2'-F-ANA containing AON was demonstrated in primary cells, specifically human PBMCs. Combination of PDE4B/4D specific AON TOP 1545-F3 (Seq ID No 85) with PDE7A specific AON TOP 1731-F2 (Seq ID No 53) increased inhibition of their respective gene targets when the second antisense was present, although the antisense sequence has no homology with the other target gene (FIG. 6a). In FIG. 6a the solid bars represent the % specific inhibition of target gene mRNA of either PDE4B, PDE4D or PDE7A when both AON are used in combination with each at a low dose (3.2 nM) compared to the AON used alone, at low and high doses (6.3 nM), demonstrating that 2-F-ANA containing AON retain the function of target gene knockdown in primary immune cells. For biological function transfection of PBMCs with combination of PDE4B/4D dual specific TOP 1545-F3 (Seq ID No 85) with PDE7A specific AON TOP 1731-F2 (Seq ID No 53) led to inhibition of both TNF-α and IL-2 secretion. 2'-F-ANA containing AON retain their functionality to reduce the inflammatory potential of immune cells.

The results in FIG. 6a also show the enhanced effect that occurs when combinations of AON specific for two different target genes are administered to cells at the same time. Although AON were administered at a concentration that had little to no effect on their target genes when employed alone, when combined, the AON induced significant inhibition on the gene expression of their respective targets (PDE4B and PDE4D for TOP 1545-F3 (Seq ID No 85), and PDE7A for TOP 1731-F2 (Seq ID No. 53)).

Example 5

Effect of PDE4B/4D AON on Mitogenic Regulatory Genes

Table 1c describes the sequence of TOP 1545 AON which has dual specificity for both PDE4B and PDE4D. Sequence of TOP 1549 (Seq ID No 17) AON has 100% homology with thymidylate synthase (TYMS) gene sequence and 5 base pair mismatches with PDE4B and PDE4D. TOP 1549 (Seq ID No 17) AON inhibits its target gene expression (TYMS) in a dose response manner (200, 400 and 800 ng) following 6 h transfection. Despite having 5 base pair mismatches with the TYMS gene sequence, TOP 1545 (Seq ID No 14) AON containing 2'-F-ANA is also efficient to inhibit TYMS gene expression in 293 cells following 6 h transfection. TYMS is a key rate-limiting enzyme of DNA synthesis and is upregulated in some cancers. TOP 1545 (Seq ID No. 14) AON has the potential to not only inhibit PDE function through the decrease of PDE4B and PDE4D mRNA levels, but could also function to inhibit proliferation of cells through its effects on TYMS gene expression. This figure demonstrates that TOP1545 (Seq ID No 14) is a novel antisense molecule that has a dual specificity for phosphodiesterase 4 (PDE4) and thymidylate synthase (TS).

Inhibitors of PDE4 are also described in the literature as cAMP elevating agents; the inhibition of PDE4 blocks the breakdown of cAMP into AMP, resulting in an accumulation of cAMP. It is well known that high intracellular levels of cAMP can effectively kill cancer cells in vitro.

Thymidylate synthase (TYMS) is the source of thymidine monophosphate for most organisms, which is necessary for DNA synthesis and cell division, and is therefore an obvious anticancer target. TYMS is not structurally related to PDEs, except for a small stretch of 17 consecutive nucleotides in its coding region. TOP1545 (Seq ID No. 14) targets this region of homology between TYMS and PDE4B and PDE4D, making TOP1545 (Seq ID No 14) a unique anti-cancer compound.

Example 6

Potency of AON In Vitro

Figure 8:
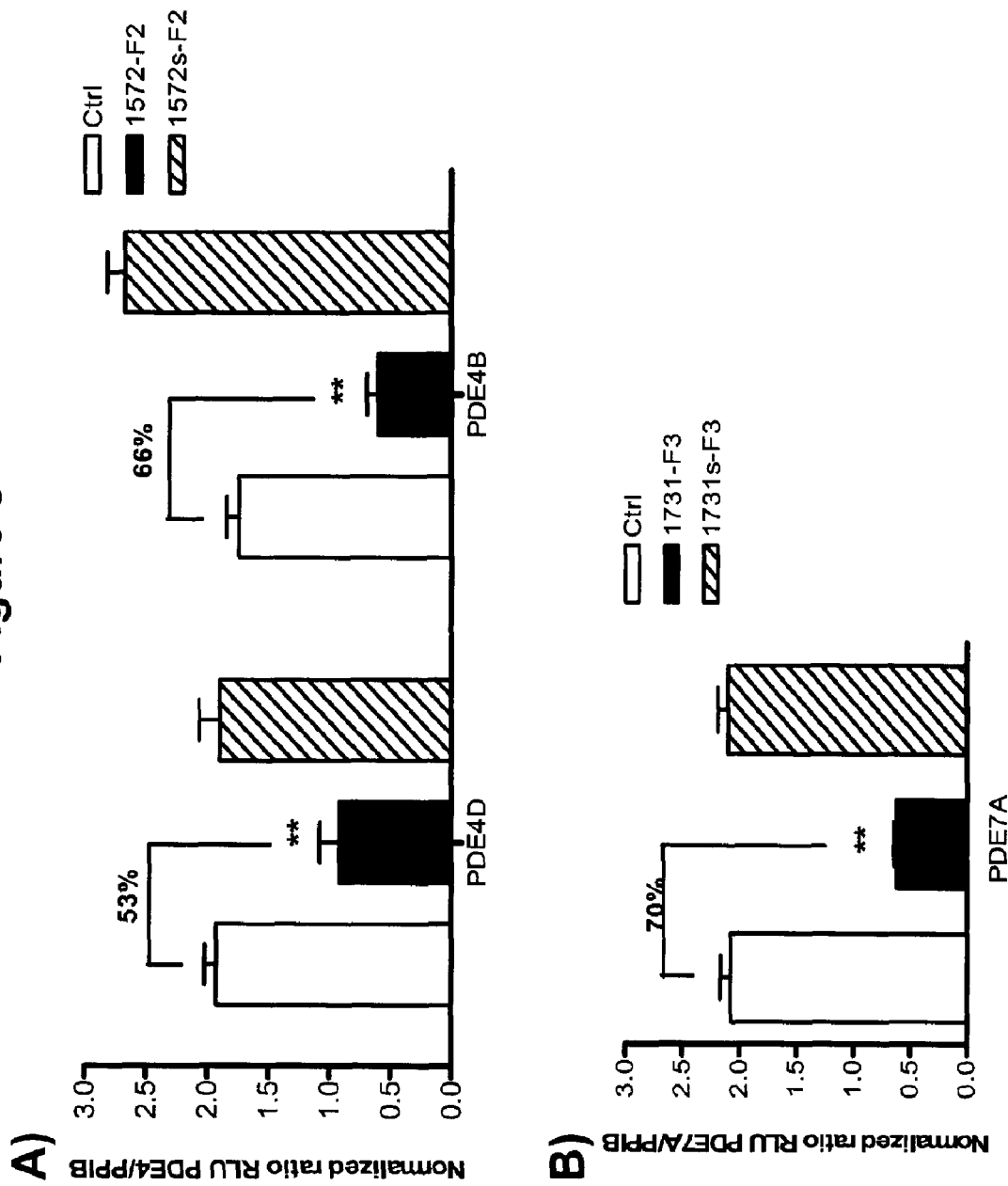
FIG. 8 shows the efficacy of (A) TOP1572-F2 at reducing PDE4D and PDE4B mRNA expression and (B) TOP1731-F3 at reducing PDE7A mRNA expression in the CYNOM-K1 monkey cell line. Cells were transfected for 24 h with 250 nM of AON or corresponding control complexed to Lipofectamine™ 2000 at ratio 1 ug oligo:2 uL lipid in antibiotic free media. PDE4D, PDE4B and PDE7A mRNA expression levels were measured by RT-PCR with relative quantification to the expression of PPIB control gene. Percentage of PDE mRNA inhibition was determined relative to the gene level in non-transfected cells. Statistical analysis was performed using one way Anova followed by Dunnett comparison, **p<0.01.

This example shows the reduction in gene expression in CYNOM-K1 monkey cells transfected with the PDE4D/4B specific AON TOP1572-F2 (Seq ID No. 122; FIG. 8 A) or the PDE7A specific AON TOP1731-F3 (Seq ID No. 54, FIG. 8 B). PDE4D and PDE4B mRNA levels were respectively reduced by 53% and 66% (FIG. 8 A) and PDE7A gene expression was reduced by 70% (FIG. 8 B) as compared to non transfected cells.

Example 7

Effect of AON Delivery on Biological Functions of Cells

This example relates the efficacy of the PDE4D/4B specific AON TOP1572-F2 (Seq ID No. 122) and TOP1545 (Seq ID No. 14) at reducing the PDE4D mRNA expression level (FIG. 9 A) and the secretion of MCP-1 cytokine stimulated in NHBE cells in response to a 4 hours stimulation with a cytomix (500 U/mL TNF-α+10 ng/mL IL1-β+10 ng/mL IFNγ) (FIG. 9 B). TOP1572-F2 (Seq ID No. 122) reduces the PDE4D mRNA expression level by 71% correlated with 34% inhibition of MCP-1 secretion. Similarly, TOP1545 (Seq ID No. 14) reduces the PDE4D mRNA expression levels by 36% correlated with 46% inhibition of MCP-1 secretion relative to cells transfected with corresponding controls.

Example 8

Effect of AON Delivery on Biological Effect in Cells

Figure 10:
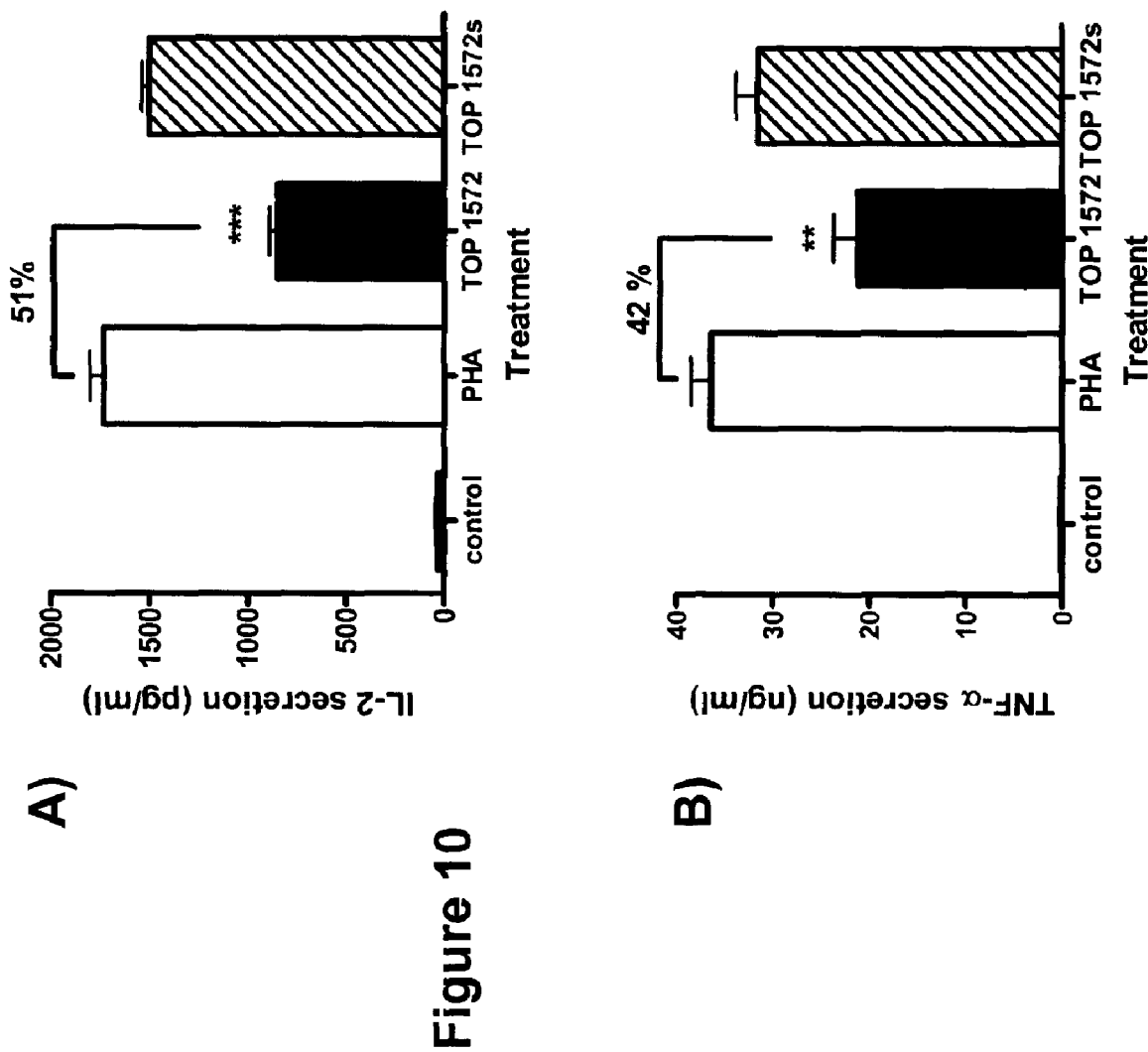
FIG. 10 shows the efficacy of the antisense oligonucleotide (AON) TOP 1572 at inhibiting cytokine secretion by PHA-stimulated human PBMCs. PBMCs were transfected with either TOP 1572 (6.2 nM) or a relevant control AON (TOP 1572 s, 6.3 nM) overnight and then stimulated the next day with the mitogen PHA (10 ug/ml) for 6 h. Levels of cytokines, IL-2 (A) and TNF-α (B) in cell supernatants were quantified using ELISA. Data represent mean values of triplicate wells± SE of IL-2 (pg/ml) or TNF-α (ng/ml). Statistical analysis was performed using one way ANOVA followed by a Bonferroni Multiple comparison test comparing cytokine levels following AON transfection to PHA-stimulated cells, or to relevant control AON treated cells, p<0.01 and *p<0.001. % inhibition of cytokine secretion is relative to levels obtained in response to PHA.
Figure 11:
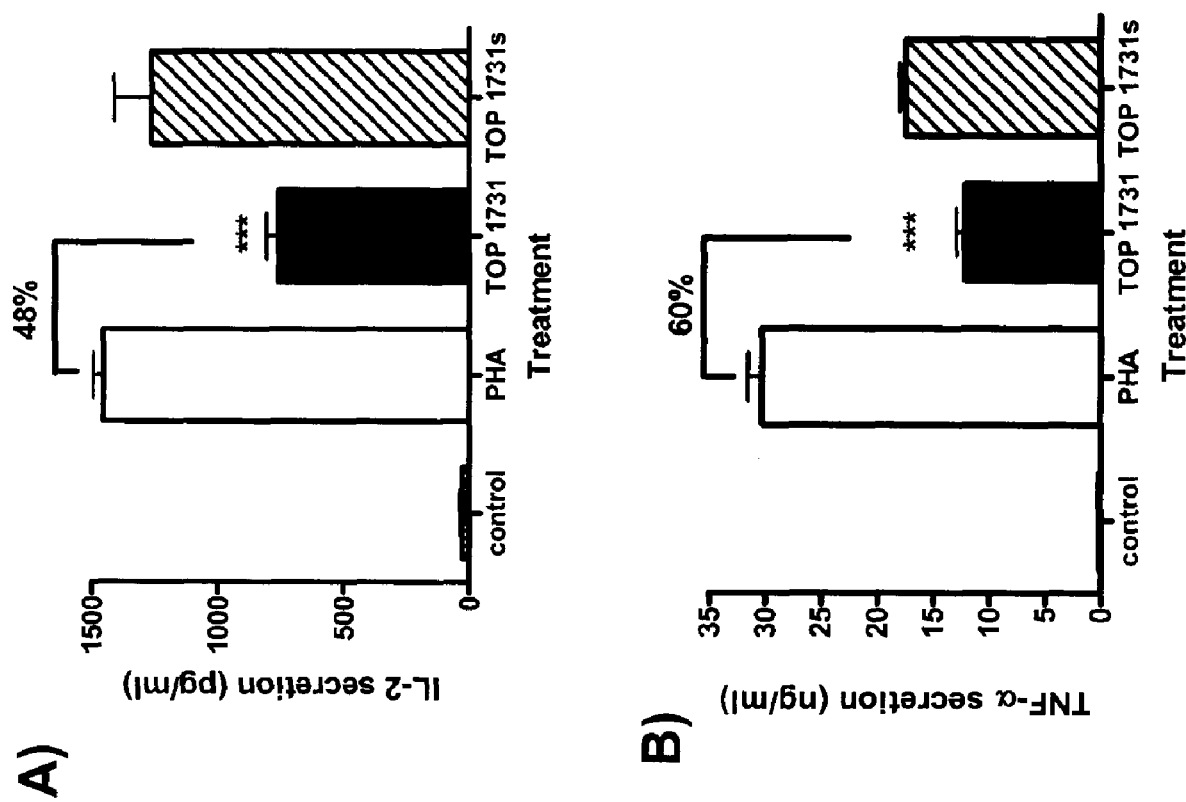
FIG. 11 shows the efficacy of the AON TOP 1731 at inhibiting cytokine secretion by mitogen-stimulated human PBMCs. PBMCs were transfected with either TOP1731 (3.1 nM) or relevant control AON (TOP 1731 s, 3.1 nM) complexed with Escort IV overnight and then stimulated the following day with mitogen PHA (10 ug/ml) for 6 h. Levels of cytokines IL-2 (A) and TNF-α (B) in cell supernatants were quantified by ELISA. Data represents mean values of triplicate wells± SE of IL-2 (pg/ml) or TNF-α (ng/ml). Statistical analysis was performed using one way ANOVA followed by a Bonferroni multiple comparison test comparing cytokine levels following AON-treatment to PHA-stimulated cells or to relevant control AON treated cells, ***p<0.001. % inhibition of cytokine secretion is relative to levels obtained in response to PHA.

This example refers to the efficacy of PDE-specific AON to inhibit the secretion of pro-inflammatory cytokines by PHA-stimulated human peripheral blood mononuclear cells (PBMCs). PBMCs are a mixed population of leukocytes including T lymphocytes, B lymphocytes and monocytes/macrophages, all of which can be stimulated to release pro-inflammatory cytokines. Human PBMCs transfected overnight with the PDE4B/4D specific TOP 1572 (FIG. 10) and then stimulated the following day with the mitogen phytohemagglutin (PHA, 10 ug/ml) for 6 h, secreted 51% less pro-inflammatory cytokine IL-2 (FIG. 10 A) and 42% less TNF-α (FIG. 10 B) as compared to those cells stimulated with PHA but not transfected. Similarly, PBMCs transfected with the PDE7A specific AON TOP 1731 (FIG. 11) secreted 48% less IL-2 and 60% less TNF-α than those PBMCs which were not transfected but stimulated with PHA.

Example 9

Enhanced Efficacy in Inhibiting Immune Responses when TOP 1572 and TOP 1731 are Combined This example refers to the effect in reducing IL-2 secretion by PHA-stimulated PBMCs when AON are combined. PBMCs transfected with 3.1 nM each of TOP 1572-F2 (Seq ID No. 122) and TOP 1731-F3 (Seq ID No. 54) resulted in a level of IL-2 inhibition (33%) which was greater than the inhibition levels observed following transfection with each AON alone at either 3.1 nM or 6.3 nM doses (FIG. 12). In this example, a low dose of TOP 1572-F2 yielded less than 10% inhibition of IL-2 whereas a higher dose (6.3 nM) yielded 24% inhibition of IL-2 (FIG. 12). With regard to TOP 1731-F3, a low dose (3.1 nM) yielded 20% inhibition of IL-2 and this level was not statistically increased when the dose was increased to 6.3 nM (22% inhibition) (FIG. 12). The combination of both TOP 1572-F2 with TOP 1731-F3 to result in a 33% inhibition of IL-2 secretion may have been due to targeting the different PDE isoforms of PDE4B, PDE4D and PDE7A simultaneously (FIG. 12).

Example 10

Comparison of PS-DNA and PS-FANA Chemistries in Cell Lines

Figure 14:
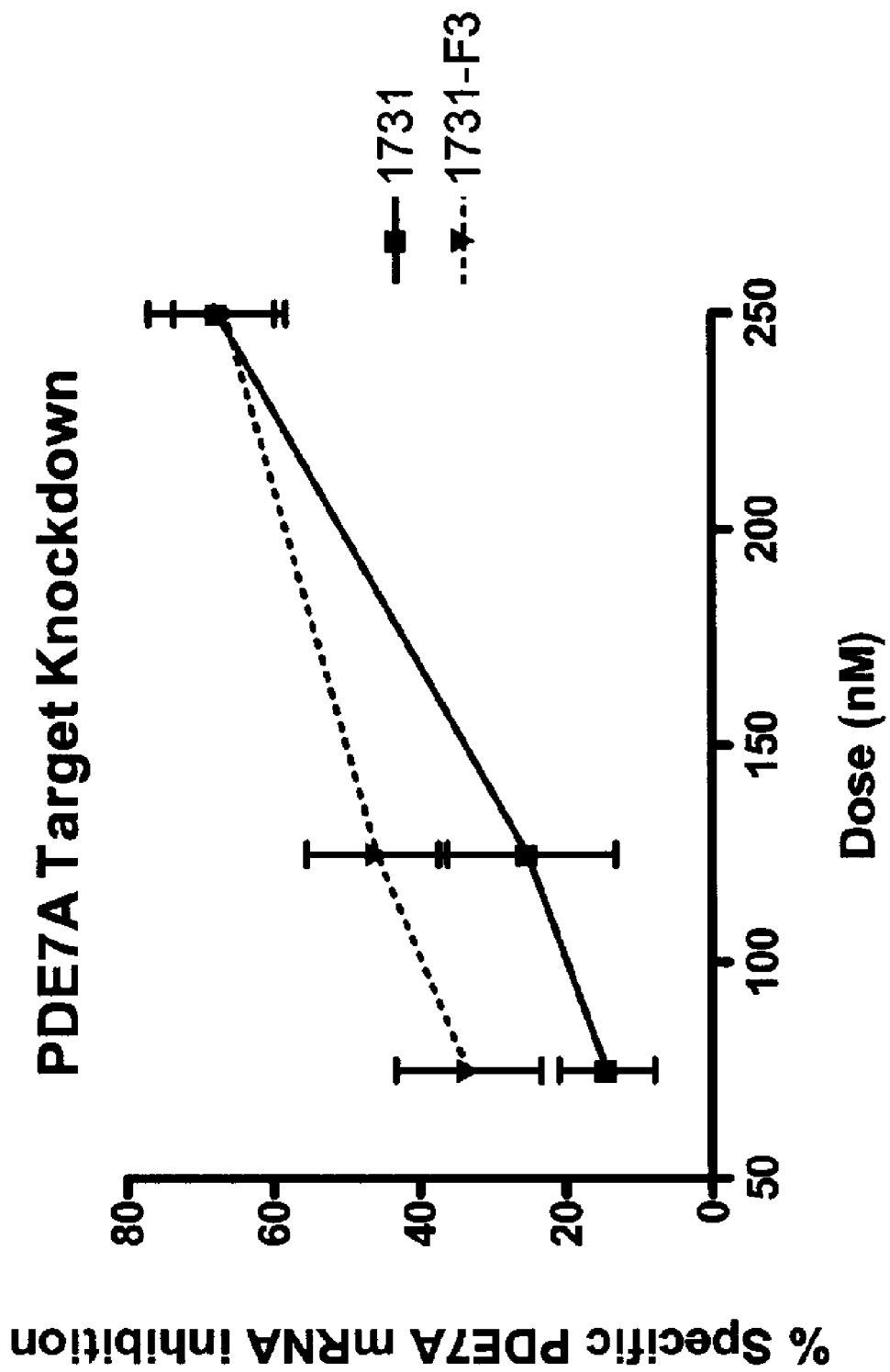
FIG. 14 compares the efficacy of TOP1731 (PS-DNA) to the efficacy of TOP1731-F3, (PS-FANA) at reducing PDE7A mRNA expression in the A549 cell line. Cells were transfected for 48 h with 250 nM, 125 nM or 75 nM of AON or corresponding control oligo complexed to Lipofectamine™ 2000 at ratio 0.8 ug oligo:1 uL lipid in antibiotic free media. PDE7A mRNA expression level was measured by Quantigene® assay with relative quantification to the expression of B2M control gene. Percentage of specific PDE mRNA inhibition was determined relative to the gene level in cells transfected with the corresponding control.

This example compares the efficacy of PS-DNA AON to the efficacy of PS-FANA AON at reducing target mRNA expression. TOP1572-F2 version (Seq ID No. 122) presents a longer duration of action than the standard PS-DNA version TOP1572 (Seq ID No. 40) at reducing the mRNA expression of both PDE4D (FIG. 13A) and PDE4B (FIG. 13B). After 72 h transfection in 293 cells, TOP1572-F3 still decreases 72% of PDE4B and 55% of PDE4D mRNA expression whereas TOP1572 efficacy is reduced at 18% for PDE4B and 29% for PDE4D. Increase of FANA AON activity is also observed at lower doses. TOP1731-F3 FANA version (Seq ID No. 54) is better than the PS-DNA version TOP1731 (Seq ID No. 2) at blocking the PDE7A mRNA expression in A549 cells transfected for 48 h at 125 nM and 75 nM doses (FIG. 14).

Although preferred embodiments of the invention have been described herein, it will be understood by those skilled in the art that variations may be made thereto without departing from the spirit of the invention or the scope of the appended claims. All documents cited in this specification are hereby incorporated by reference.

TABLE 1a

| Target gene | Accession number | Antisense ID | Antisense sequence (5'-3') | Seq ID No. |
|---|---|---|---|---|
| PDE7A | NM_002603 | TOP1730 | TCATGAGTGGCAGCTGCAA | 1 |
| | | TOP1731 | TCATGAGTGGCAGCTGCAATT | 2 |
| | | TOP1732 | CATGAGTGGCAGCTGCAATTAA | 3 |
| | | TOP1733 | GAGTGGCAGCTGCAATTAAGC | 4 |
| | | TOP1734 | ATGAGTGGCAGCTGCAATTAA | 5 |
| | | TOP1735 | AGATCATGAGTGGCAGCTGCA | 6 |
| | | TOP1736 | GAGTGGCAGCTGCAATTAA | 7 |
| | | TOP1737 | GATCATGAGTGGCAGCTGCAA | 8 |

TABLE 1b

| Target gene | Accession number | Antisense ID | Antisense sequence (5'-3') | Seq ID No. |
|---|---|---|---|---|
| PDE3A | NM_000921 | TOP1313 | CCTCAGCACCAGCCATGTCG | 9 |

TABLE 1c

| Target genes | Accession numbers | Antisense ID | Antisense sequence (5'-3') | Seq ID No. |
|---|---|---|---|---|
| PDE4A + 4D | NM_006202 | TOP1507 | GTGCTTGTCACACATGG | 10 |
| | NM_006203 | TOP1508 | GTCCTCCAAAGTGTCC | 11 |
| PDE4B + 4D | NM_002600 | TOP1511 | GGTCTCTAGCTGGTC | 12 |
| | NM_006203 | TOP1544 | ATGGTAATGGTCTTC | 13 |
| | | TOP1545 | TCTGCCCATGTCTCCCA | 14 |
| | | TOP1546 | AAGACCCCATTTGTTCA | 15 |
| | | TOP1547 | TCTGCCCAGGTCTCCCA | 16 |
| | | TOP1549 | GAGGCCCATGTCTCCCG | 17 |
| | | TOP1550 | TCTGCCCATGTCTCCCAGA | 18 |
| | | TOP1551 | TCTGCCCATGTCTCCCACA | 19 |
| | | TOP1552 | TCTGCCCATGTCTCCCAGAG | 20 |
| | | TOP1553 | TCTGCGCATGTCTCCCACAA | 21 |
| | | TOP1554 | GGTTGCTCAGGTCTGCACAGT | 22 |
| | | TOP1555 | GGTTGCTCAGATCTGCACAGT | 23 |
| | | TOP1556 | GGTTGCTCAGITCTGCACAGT | 24 |
| | | TOP1557 | TCAGCATGGTAATGGTCTT | 25 |
| | | TOP1558 | GCCACITCAGCATGGTAAT | 26 |
| | | TOP1559 | TACATCAAIGCAAGTTC | 27 |
| | | TOP1560 | ATGTCACAGTITTCTTC | 28 |
| | | TOP1561 | TGTCAATIACCATTTTCCT | 29 |
| | | TOP1562 | GTTTCIACCATIGTCTTCA | 30 |
| | | TOP1563 | CTTTCTTAGTTTCIACCAT | 31 |
| | | TOP1564 | TCTGCACAGTGCACGAT | 32 |
| | | TOP1565 | GTCTGTAIGGTCTCTAGCT | 33 |
| | | TOP1566 | TGTAIGGTCTCTAGCTGGT | 34 |
| | | TOP1567 | TTCTTGACTCCACTIATCT | 35 |
| | | TOP1568 | AATCAAGTCATCICCGTGT | 36 |
| | | TOP1569 | GTTGTGATAIGCCACITCA | 37 |
| | | TOP1570 | ATTITACATCAAIGCAAGT | 38 |
| | | TOP1571 | TGTTTIGACATATCIGTT | 39 |
| | | TOP1572 | GGTTGCTCAGITCTGCACA | 40 |
| | | TOP1573 | GGTTGCTCAGATCTGCACA | 113 |
| | | TOP1574 | TTGCTCAGATCTGCA | 114 |

TABLE 1d

| Target genes | Accession numbers | Antisense ID | Antisense sequence (5'-3') | Seq ID No. |
|---|---|---|---|---|
| PDE3B | NM_006203 | TOP1360 | TCAGCAGCGTCCGCAGCCAG | 89 |
| PDE4D | NM_006202 | TOP1497 | CTGCCTCCTCTTCAACCTG | 90 |
| PDE4A + 4B | NM_002600 | TOP1512 | CCATGATGCGGTCTGTCCA | 91 |
| PDE7A | NM_002603 | TOP1716 | TCATGAGTGGCAGCTGC | 92 |

TABLE 2a

| Target gene | Antisense ID | FANA-Antisense ID | Antisense sequence (5'-3') | Seq ID NO |
|---|---|---|---|---|
| PDE7A | TOP1716 | TOP1716-F1 | PS-TCA TGA gtg gca GCT GC | 41 |
| | | TOP1716-F2 | PS-TCA tgA GTg gCA gcT GC | 42 |
| | | TOP1716-F3 | PS-tCa TgA gTg GcA gct gC | 43 |
| | | TOP1716-F4 | PS-TCA tGA gtg gca GCT GC | 44 |
| | | TOP1716-F5 | PS-TCA tga gtg gca GCT GC | 45 |
| | TOP1714 | TOP1714-F1 | PS-GCT TAg gtt cct TTA AGT | 46 |
| | TOP1729 | TOP1729-F1 | PS-CAG ATc atg agt ccC AGC TG | 47 |
| | TOP1730 | TOP1730-F1 | PS-TCA TGa gtg gca gCT GCA A | 48 |
| | | TOP1730-F2 | PS-TCA Tga gtg gca gct GCA A | 49 |
| | | TOP1730-F3 | PS-TCa tga gtg gca gct GCA A | 50 |
| | | TOP1730-F4 | PS-TCa tga gtg gcA GCT GCA A | 51 |
| | TOIP1731 | TOP1731-F1 | PS-TCA TGa gtg gca gct GCA ATT | 52 |
| | | TOP1731-F2 | PS-TCA Tga gtg gca gct gcA ATT | 53 |
| | | TOP1731-F3 | PS-TCa tga gtg gca gct gcA ATT | 54 |
| | | TOP1731-F4 | PS-TCa tga gtg gcA GCT GCA ATT | 55 |
| | | TOP1731-F5 | PS-TCA Tga gtg GCa gct gcA ATT | 115 |
| | | TOP1731-F6 | PS-TCa tGA gtg GCA gct gcA ATT | 116 |
| | TOP1733 | TOP1733-F1 | PS-GAG TGg cag ctg caa TTA AGC | 56 |
| | TOP1734 | TOP1734-F1 | PS-ATG AGt ggc agc tgc AAT TAA | 57 |
| | TOP1736 | TOP1736-F1 | PS-GAG TGg cag ctg cAA TTA A | 58 |
| | TOP1737 | TOP1737-F1 | PS-GAT CAt gag tgg cag CTG CAA | 59 |

TABLE 2b

| Target gene | Antisense ID | FANA-Antisense ID | Antisense sequence 5'-3' | Seq ID No. |
|---|---|---|---|---|
| PDE3A | TOP1311 | TOP1311-F1 | PS-CGG CCA AGC agc tga gCA CC | 60 |
| | | TOP1311-F2 | PS-CGG CCA Agc agc tgA GCA CC | 61 |
| | | TOP1311-F3 | PS-CGG CCA agc agc TGA GCA CC | 62 |

TABLE 2c

| Target gene | Antisense ID | FANA-Antisense ID | Antisense sequence 5'-3' | Seq ID No. |
|---|---|---|---|---|
| PDE3B | TOP1360 | TOP1360-F1 | PS-TCA GCA Gcg tcc gCA GCC AG | 63 |
| | | TOP1360-F2 | PS-TCA gca gCG Tcc gCA gcc AG | 64 |
| | | TOP1360-F3 | PS-TCA gCa gCg TCC gCa gCC ag | 65 |

TABLE 2d

| Target gene | Antisense ID | FANA-Antisense ID | Antisense sequence (5'-3') | Seq ID No. |
|---|---|---|---|---|
| PDE4A | TOP1413 | TOP1413-F1 | PS-GCC ACG ctc gcg CTC TC | 66 |
| | | TOP1413-F2 | PS-GCC acg CTC gcg ctC TC | 67 |
| | | TOP1413-F3 | PS-gcc ACG ctc GCG CTc tc | 68 |

TABLE 2e

| Target gene | Antisense ID | FANA-Antisense ID | Antisense sequence 5'-3' | Seq ID No. |
|---|---|---|---|---|
| PDE4D | TOP1498 | TOP1498-F1 | PS-CTT CAg gct ggC TTT CCT C | 69 |
| | | TOP1498-F2 | PS-ctT Cag gCT ggC Ttt CCt c | 70 |
| | | TOP1498-F3 | PS-ctt cag gct gGC TTT CCT C | 71 |
| | TOP1497 | TOP1497-F1 | PS-CTG CCT cct ctt caA CCT G | 72 |
| | | TOP1497-F2 | PS-ctg cCT CCt ctT CAA cct g | 73 |
| | | TOP1497-F3 | PS-ctg cCT CCt BtT CAA cct g | 74 |
| | | TOP1497-F4 | PS-CTg cCT cct ctt caA CCT G | 75 |
| | | TOP1497-F5 | PS-CTg cct cct ctt caA CCT G | 76 |
| | | TOP1497-F6 | PS-ctg cct cct ctt caA CCT G | 77 |

TABLE 2f

| Target gene | Antisense ID | FANA-Antisense ID | Antisense sequence 5'-3' | Seq ID No. |
|---|---|---|---|---|
| PDE4B | TOP1432 | TOP1432-F1 | PS-GAC CGG Tag gtc tgT ATG GT | 78 |
| | | TOP1432-F2 | PS-GAC CGG Tag gtc tgT BTG GT | 79 |
| | | TOP1432-F3 | PS-GAC Cgg tag gtC TGT BTG GT | 80 |

TABLE 2g

| Target gene | Antisense ID | FANA-Antisense ID | Antisense sequence (5'-3') | Seq ID No. |
|---|---|---|---|---|
| PDE4A + 4D | TOP1505 | TOP1505-F1 | PS-GTC CAC tgg cgG TAC AG | 81 |
| PDE4A + 4B | TOP1512 | TOP1512-F1 | PS-CCA TGA tgc ggt cTG TCC A | 82 |
| PDE4B + 4D | | TOP1545-F1 | PS-TCT GCc cat gtC TCC CA | 83 |
| | | TOP1545-F2 | PS-TCt gcc cat gtC TCC CA | 84 |
| | TOP1545 | TOP1545-F3 | PS-TCt gcc cat gtc tCC CA | 85 |
| | | TOP1545-F4 | PS-TCt gcc cat gTC tcC CA | 86 |
| | | TOP1545-F5 | PS-TCt gCc CaT gTc TcC CA | 87 |
| | | TOP1545-F6 | PS-TCt gcc CAT gtc tCC CA | 88 |
| | TOP1556 | TOP1556-F1 | PS-GGT TGc tca git ctg CAC AGT | 117 |
| | | TOP1556-F2 | PS-GGt tgc tca git ctg cAC AGT | 118 |
| | TOP1570 | TOP1570-F1 | PS-ATt ita cat caa igC AAG T | 119 |
| | | TOP1570-F2 | PS-ATt ita CAT caa igC AAG T | 120 |
| | TOP1572 | TOP1572-F1 | PS-GGT TGc tca git cTG CAC A | 121 |
| | | TOP1572-F2 | PS-GGt tgc tca git ctG CAC A | 122 |
| | | TOP1572-F3 | PS-GGt tgc TCA git ctG CAC A | 123 |
| | | TOP1572-F4 | PS-GGt tgc tca git Ctg CAC A | 124 |
| | TOP1573 | TOP1573-F2 | PS-GGt tgc tca gat ctg CAC A | 125 |
| | TOP1574 | TOP1574-F2 | PS-TTG ctc aga tct GCA | 126 |

TABLE 3

| Target gene | Sense primer (5'-3') | SEQ ID No. | Product size (bp) |
|---|---|---|---|
| PDE7A | TCAGGCCATGCACTGTTACT | 93 | 229 |
| PDE3A | CAACAGTGACAGCAGTGACATT | 95 | 166 |
| PDE3B | GATTCTTTGGGATTGGGACT | 97 | 212 |
| PDE4A | ATCAACACCAATTCGGAGCT | 99 | 199 |
| PDE4B | TGGCAGACCTGAAGACAATG | 101 | 181 |
| PDE4D | CAGAATATGGTGCACTGTGC | 103 | 192 |
| HPRT | ATCAGACTGAAGAGCTTTGTAATGACCA | 105 | 230 |
| B2M | CAAGGACTGGTCTTTCTATCTCTTGT | 107 | 338 |
| PPIB | AGAGCATCTACGGTGAGCG | 109 | 196 |
| TYMS | AAGAATCATCATGTGCGCTT | 111 | 226 |
| | Antisense primer (5'-3') | | |
| PDE7A | CCTGATTCTCTCAATAAGCCC | 94 | 229 |
| PDE3A | TTGAGTCCAGGTTATCCATGAC | 96 | 166 |
| PDE3B | ATCTTTGGCCTACAGGAACC | 98 | 212 |
| PDE4A | CCAGCACCATGTCGATGAC | 100 | 199 |
| PDE4B | AAATTCCTCCATGATGCGG | 102 | 181 |
| PDE4D | AGTCTATGAAGCCCACCTGTG | 104 | 192 |

TABLE 3-continued

| Target gene | | SEQ ID No. | Product size (bp) |
|---|---|---|---|
| HPRT | TGGCTTATATCCAACACTTCGTG | 106 | 230 |
| B2M | GTGGAGCAACCTGCTCAGATAC | 108 | 338 |
| PPIB | CTTCCGCACCACCTCCA | 110 | 196 |
| TYMS | GTGTGTATAAAGTCACCTGGCTT | 112 | 226 |

We claim:

1. An oligonucleotide having a base sequence selected from the group consisting of (i) SEQ ID NOS. 2, 40, 52-55, 115-116 and 121-124 and (ii) SEQ ID NOS. 2, 40, 52-55, 115-116 and 121-124 containing a one base insertion, deletion or substitution.

2. The oligonucleotide of claim 1 having a base sequence selected from the group consisting of SEQ ID NOS. 2, 40, 52-55, 115-116 and 121-124.

3. The oligonucleotide of claim 1 having a phosphodiester backbone.

4. The oligonucleotide of claim 1 having a phosphorothioate backbone.

5. The oligonucleotide of claim 4 wherein at least one nucleotide of the oligonucleotide is a 2'-deoxy-2'-fluoroarabinonucleotide.

6. The oligonucleotide of claim 5 selected from the group consisting of SEQ ID NOS. 52-55, 115-116 and 121-124.

7. A pharmaceutical composition comprising the oligonucleotide of claim 1 in combination with a pharmaceutically acceptable carrier.

8. A pharmaceutical composition comprising at least two oligonucleotides of claim 1 in combination with a pharmaceutically acceptable carrier.

9. A pharmaceutical composition comprising SEQ ID NO. 2 and SEQ ID NO. 14 in combination with a pharmaceutically acceptable carrier.

10. A pharmaceutical composition comprising SEQ ID NO. 2 and SEQ ID NO. 24 in combination with a pharmaceutically acceptable carrier.

11. A pharmaceutical composition comprising SEQ ID NO. 2 and SEQ ID NO. 37 in combination with a pharmaceutically acceptable carrier.

12. A pharmaceutical composition comprising SEQ ID NO. 2 and SEQ ID NO. 40 in combination with a pharmaceutically acceptable carrier.

13. A pharmaceutical composition comprising SEQ ID NO. 2 and SEQ ID NO. 85 in combination with a pharmaceutically acceptable carrier.

14. A pharmaceutical composition comprising SEQ ID NO. 2 and SEQ ID NO. 122 in combination with a pharmaceutically acceptable carrier.

15. A pharmaceutical composition comprising SEQ ID NO. 53 and SEQ ID NO. 14 in combination with a pharmaceutically acceptable carrier.

16. A pharmaceutical composition comprising SEQ ID NO. 53 and SEQ ID NO. 24 in combination with a pharmaceutically acceptable carrier.

17. A pharmaceutical composition comprising SEQ ID NO. 53 and SEQ ID NO. 37 in combination with a pharmaceutically acceptable carrier.

18. A pharmaceutical composition comprising SEQ ID NO. 53 and SEQ ID NO. 40 in combination with a pharmaceutically acceptable carrier.

19. A pharmaceutical composition comprising SEQ ID NO. 53 and SEQ ID NO. 85 in combination with a pharmaceutically acceptable carrier.

20. A pharmaceutical composition comprising SEQ ID NO. 53 and SEQ ID NO. 122 in combination with a pharmaceutically acceptable carrier.

21. A pharmaceutical composition comprising SEQ ID NO. 54 and SEQ ID NO. 14 in combination with a pharmaceutically acceptable carrier.

22. A pharmaceutical composition comprising SEQ ID NO. 54 and SEQ ID NO. 24 in combination with a pharmaceutically acceptable carrier.

23. A pharmaceutical composition comprising SEQ ID NO. 54 and SEQ ID NO. 37 in combination with a pharmaceutically acceptable carrier.

24. A pharmaceutical composition comprising SEQ ID NO. 54 and SEQ ID NO. 40 in combination with a pharmaceutically acceptable carrier.

25. A pharmaceutical composition comprising SEQ ID NO. 54 and SEQ ID NO. 85 in combination with a pharmaceutically acceptable carrier.

26. A method for treating a subject having a disease associated with reduced cAMP comprising administering a pharmaceutical composition of claim 7.

27. A method for treating respiratory inflammation in a subject comprising administering the pharmaceutical composition of claim 7.

28. The method of claim 27, wherein the respiratory inflammation is caused by any one of chronic obstructive pulmonary disease, asthma, eosinophilic cough, bronchitis, acute and chronic rejection of lung allograft, sarcoidosis, pulmonary fibrosis, rhinitis, sinusitis, viral infection or a neoplastic disease.

29. The method of claim 28 wherein the disease is chronic obstructive pulmonary disease.

30. A pharmaceutical composition comprising at least two oligonucleotides having SEQ ID NO. 54 and SEQ ID NO. 122 in combination with a pharmaceutically acceptable carrier.

31. The oligonucleotide of claim 1 consisting of SEQ ID NO:2.

32. The oligonucleotide of claim 1 consisting of SEQ ID NO:40.

* * * * *